(12) United States Patent
Dieterle et al.

(10) Patent No.: US 7,592,483 B2
(45) Date of Patent: Sep. 22, 2009

(54) PREPARATION OF ACROLEIN OR ACRYLIC ACID OR A MIXTURE THEREOF BY HETEROGENEOUSLY CATALYZED PARTIAL GAS PHASE OXIDATION OF PROPYLENE

(75) Inventors: Martin Dieterle, Mannheim (DE);
Armin Diefenbacher, Germersheim (DE); Goetz-Peter Schindler, Mannheim (DE); Catharina Klanner, Mannheim (DE); Klaus Joachim Mueller-Engel, Stutensee (DE); Christoph Adami, Weinheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 516 days.

(21) Appl. No.: 11/131,261

(22) Filed: May 18, 2005

(65) Prior Publication Data
US 2006/0004227 A1    Jan. 5, 2006

Related U.S. Application Data

(60) Provisional application No. 60/678,774, filed on May 9, 2005, provisional application No. 60/662,804, filed on Mar. 18, 2005, provisional application No. 60/657,374, filed on Mar. 2, 2005, provisional application No. 60/657,407, filed on Mar. 2, 2005, provisional application No. 60/656,874, filed on Mar. 1, 2005, provisional application No. 60/656,875, filed on Mar. 1, 2005, provisional application No. 60/584,469, filed on Jul. 1, 2004.

(30) Foreign Application Priority Data

| Jul. 1, 2004 | (DE) | 10 2004 032 129 |
| Mar. 1, 2005 | (DE) | 10 2005 009 885 |
| Mar. 1, 2005 | (DE) | 10 2005 009 891 |
| Mar. 2, 2005 | (DE) | 10 2005 010 111 |
| Mar. 18, 2005 | (DE) | 10 2005 013 039 |

(51) Int. Cl.
*C07C 229/00* (2006.01)
*C07C 53/00* (2006.01)
*C07C 45/00* (2006.01)

(52) U.S. Cl. .................... 562/546; 562/512.2; 568/479

(58) Field of Classification Search .................. None
See application file for complete search history.

(56) References Cited

U.S. PATENT DOCUMENTS

| 3,161,670 A | 12/1964 | Adams et al. |
| 4,317,926 A | 3/1982 | Sato et al. |
| 4,413,147 A | 11/1983 | Khoobiar |
| 4,532,365 A | 7/1985 | Khoobiar |
| 4,535,188 A | 8/1985 | Khoobiar |
| RE32,082 E | 2/1986 | Khoobiar |
| 5,198,578 A | 3/1993 | Etzkorn et al. |
| 5,426,221 A | 6/1995 | Willersinn |
| 5,637,222 A | 6/1997 | Herbst et al. |
| 5,705,684 A | 1/1998 | Hefner et al. |
| 5,780,679 A | 7/1998 | Egly et al. |
| 5,831,124 A | 11/1998 | Machhammer et al. |
| 5,897,749 A | 4/1999 | Kroker et al. |
| 6,207,022 B1 | 3/2001 | Dockner et al. |
| 6,348,638 B1 | 2/2002 | Schliephake et al. |
| 6,350,906 B2 | 2/2002 | Machhammer et al. |
| 6,395,936 B1 | 5/2002 | Arnold et al. |
| 6,403,829 B1 | 6/2002 | Unverricht et al. |
| 6,413,379 B1 | 7/2002 | Machhammer et al. |
| 6,423,875 B1 | 7/2002 | Machhammer et al. |
| 6,426,433 B1 | 7/2002 | Machhammer et al. |
| 6,448,439 B1 | 9/2002 | Eck et al. |
| 6,498,272 B1 | 12/2002 | Schroeder et al. |
| 6,525,217 B1 | 2/2003 | Unverricht et al. |
| 6,555,707 B1 | 4/2003 | Nestler et al. |
| 6,596,901 B1 | 7/2003 | Eck et al. |
| 6,646,161 B1 | 11/2003 | Eck et al. |
| 6,679,939 B1 | 1/2004 | Thiel et al. |
| 6,727,383 B1 | 4/2004 | Nestler et al. |
| 6,781,017 B2 | 8/2004 | Machhammer et al. |
| 6,888,024 B2 | 5/2005 | Dieterle et al. |
| 6,939,991 B2 | 9/2005 | Thiel et al. |
| 2001/0007043 A1 | 7/2001 | Machhammer et al. |
| 2003/0060661 A1 | 3/2003 | Eck et al. |
| 2003/0175159 A1 | 9/2003 | Heilek et al. |
| 2003/0187299 A1 | 10/2003 | Machhammer et al. |
| 2004/0063988 A1 | 4/2004 | Hechler et al. |
| 2004/0063989 A1 | 4/2004 | Hechler et al. |
| 2004/0097756 A1 | 5/2004 | Thiel et al. |
| 2004/0116736 A1 | 6/2004 | Machhammer et al. |
| 2004/0116741 A1 | 6/2004 | Nordhoff et al. |
| 2004/0138501 A1 | 7/2004 | Thiel et al. |
| 2004/0181083 A1 | 9/2004 | Proll et al. |
| 2004/0191953 A1 | 9/2004 | Dieterle et al. |
| 2004/0192963 A1 | 9/2004 | Dieterle et al. |
| 2004/0192964 A1 | 9/2004 | Petzoldt et al. |
| 2004/0192965 A1 | 9/2004 | Petzoldt et al. |
| 2004/0199001 A1 | 10/2004 | Schindler et al. |

(Continued)

FOREIGN PATENT DOCUMENTS

DE    10 53 086    3/1959

(Continued)

*Primary Examiner*—Paul A Zucker
(74) *Attorney, Agent, or Firm*—Oblon, Spivak, McClelland, Maier & Neustadt, P.C.

(57) ABSTRACT

A process for preparing acrolein or acrylic acid or a mixture thereof by heterogeneously catalyzed partial gas oxidation of propylene, in which the starting reaction gas mixture has the following contents:
from 6 to 9% by volume of propylene,
from 8 to 18% by volume of molecular oxygen,
from 6 to 30% by volume of propane and
from 32 to 72% by volume of molecular nitrogen.

45 Claims, 1 Drawing Sheet

U.S. PATENT DOCUMENTS

| | | |
|---|---|---|
| 2004/0225158 A1 | 11/2004 | Dieterle et al. |
| 2004/0242826 A1 | 12/2004 | Nishimura |
| 2004/0249196 A1 | 12/2004 | Dieterle et al. |
| 2004/0256319 A1 | 12/2004 | Hammon et al. |
| 2004/0260121 A1 | 12/2004 | Nestler et al. |
| 2005/0006299 A1 | 1/2005 | Heilek et al. |
| 2005/0090628 A1 | 4/2005 | Eck et al. |
| 2005/0101803 A1 | 5/2005 | Dieterle et al. |
| 2005/0119515 A1 | 6/2005 | Machhammer et al. |

FOREIGN PATENT DOCUMENTS

| | | |
|---|---|---|
| DE | 33 13573 A1 | 10/1983 |
| DE | 43 08 087 A1 | 9/1994 |
| DE | 43 35 172 A1 | 4/1995 |
| DE | 44 36 243 A1 | 4/1996 |
| DE | 195 01 325 A1 | 7/1996 |
| DE | 195 08 558 A1 | 9/1996 |
| DE | 196 06 877 A1 | 8/1997 |
| DE | 196 27 847 A1 | 1/1998 |
| DE | 197 40 252 A1 | 3/1999 |
| DE | 197 40 253 A1 | 3/1999 |
| DE | 198 37 517 A1 | 2/2000 |
| DE | 198 37 519 A1 | 2/2000 |
| DE | 198 37 520 A1 | 2/2000 |
| DE | 199 24 533 A1 | 11/2000 |
| DE | 199 24532 A1 | 11/2000 |
| DE | 199 48 248 A1 | 4/2001 |
| DE | 101 15 277 A1 | 6/2002 |
| DE | 101 31 297 A1 | 1/2003 |
| DE | 102 35 847 A1 | 8/2003 |
| DE | 102 11 275 A1 | 9/2003 |
| DE | 102 23 058 A1 | 12/2003 |
| DE | 103 13 209 A1 | 3/2004 |
| DE | 103 36 386 A1 | 3/2004 |
| DE | 102 43 625 A1 | 4/2004 |
| DE | 102 45 585 A1 | 4/2004 |
| DE | 102 46 119 A1 | 4/2004 |
| DE | 102 47 240 A1 | 4/2004 |
| DE | 103 32 758 A1 | 5/2004 |
| DE | 103 16 039 A1 | 10/2004 |
| DE | 10 2004 025 445 A1 | 2/2005 |
| DE | 10 2004 032 129 A1 | 3/2005 |
| DE | 10 2004 021 763 A1 | 5/2005 |
| DE | 10 2004 021 764 A1 | 6/2005 |
| DE | 103 51 269 A1 | 6/2005 |
| EP | 0 117 146 A1 | 8/1984 |
| EP | 0 274 681 A1 | 7/1988 |
| EP | 0 293 224 A1 | 11/1988 |
| EP | 0 695 736 A1 | 2/1996 |
| EP | 0 792 867 A2 | 9/1997 |
| EP | 0 854 129 A1 | 7/1998 |
| EP | 0 920 408 B1 | 6/1999 |
| EP | 0 925 272 B1 | 6/1999 |
| EP | 0 982 287 A1 | 3/2000 |
| EP | 0 982 288 A2 | 3/2000 |
| EP | 0 982 289 A2 | 3/2000 |
| EP | 0 990 636 A1 | 4/2000 |
| EP | 1 015 410 B1 | 7/2000 |
| EP | 1 015 411 B1 | 7/2000 |
| EP | 1 041 062 A2 | 10/2000 |
| EP | 1 066 239 B1 | 1/2001 |
| EP | 1 066 240 B1 | 1/2001 |
| EP | 1 068 174 B1 | 1/2001 |
| EP | 1 070 700 A2 | 1/2001 |
| EP | 1 106 598 A2 | 6/2001 |
| EP | 1 180 508 A1 | 2/2002 |
| EP | 1 388 532 A1 | 2/2004 |
| EP | 1 388 533 A1 | 2/2004 |
| EP | 1 484 303 A2 | 12/2004 |
| EP | 1 484 308 A1 | 12/2004 |
| EP | 1 484 309 A1 | 12/2004 |
| WO | WO 97/36849 | 10/1997 |
| WO | WO 97/48669 | 12/1997 |
| WO | WO 98/01415 | 1/1998 |
| WO | WO 99/14181 | 3/1999 |
| WO | WO 99/14182 | 3/1999 |
| WO | WO 99/50219 | 10/1999 |
| WO | WO 99/50220 | 10/1999 |
| WO | WO 99/50222 | 10/1999 |
| WO | WO 00/53556 | 9/2000 |
| WO | WO 00/53557 | 9/2000 |
| WO | WO 00/53558 | 9/2000 |
| WO | WO 00/53559 | 9/2000 |
| WO | WO 00/53560 | 9/2000 |
| WO | WO 00/53561 | 9/2000 |
| WO | WO 01/77056 A1 | 10/2001 |
| WO | WO 01/96270 A2 | 12/2001 |
| WO | WO 01/96271 A2 | 12/2001 |
| WO | WO 02/09839 A1 | 2/2002 |
| WO | WO 02/055469 A1 | 7/2002 |
| WO | WO 03/011804 A2 | 2/2003 |
| WO | WO 03/029177 A1 | 4/2003 |
| WO | WO 03/041832 A1 | 5/2003 |
| WO | WO 03/041833 A1 | 5/2003 |
| WO | WO 03/076370 A1 | 9/2003 |
| WO | WO 03/078378 A1 | 9/2003 |
| WO | WO 2004/031106 A1 | 4/2004 |
| WO | WO 2004/035514 A1 | 4/2004 |
| WO | WO 2004/063138 A1 | 7/2004 |
| WO | WO 2004/085362 A1 | 10/2004 |
| WO | WO 2004/085363 A1 | 10/2004 |
| WO | WO 2004/085365 A2 | 10/2004 |
| WO | WO 2004/085367 A1 | 10/2004 |
| WO | WO 2004/085369 A1 | 10/2004 |
| WO | WO 2004/085370 A1 | 10/2004 |

PREPARATION OF ACROLEIN OR ACRYLIC ACID OR A MIXTURE THEREOF BY HETEROGENEOUSLY CATALYZED PARTIAL GAS PHASE OXIDATION OF PROPYLENE

BACKGROUND OF THE INVENTION

1 Field of the Invention

The present invention relates to a process for preparing acrolein or acrylic acid or a mixture thereof by heterogeneously catalyzed partial gas phase oxidation of propene, in which a starting reaction gas mixture which comprises the propylene and molecular oxygen reactants and the inert molecular nitrogen and propane diluent gases and comprises the molecular oxygen and the propylene in a molar $O_2:C_3H_6$ ratio of $\geq 1$ is conducted at elevated temperature through a fixed catalyst bed whose active composition is at least one multimetal oxide comprising the elements, Mo, Fe and Bi.

2 Description of the Background

Acrolein is a reactive monomer which is especially significant as an intermediate, for example in the preparation of acrylic acid by two-stage heterogeneously catalyzed partial gas phase oxidation of propene. Acrylic acid is suitable as such or in the form of its alkyl esters, for example for preparing polymers which may find use as adhesives or water-absorbent materials among other uses.

The preparation of acrolein by the process, described in the preamble of this document, for the heterogeneously catalyzed partial gas phase oxidation is known (cf., for example, EP-A 11 06 598, WO 97/36849, EP-A 293 224, WO 01/96271, DE-A 198 37 517, EP-A 274 681, DE-A 198 37 519, DE-A 198 37 520, EP-A 117 146, WO 03/11804, U.S. Pat. No. 3,161,670, WO 01/96270, DE-A 195 08 558, DE-A 33 13 573, DE-A 102 45 585, WO 03/076370, DE-A 103 16 039, WO 04/031106, and the German application DE-A 10 2004 032 129 and the prior art cited in these documents). Typically, it forms the first stage of a two-stage heterogeneously catalyzed gas phase partial oxidation of propene to acrylic acid. In the first reaction stage, the propene is substantially partially oxidized to acrolein and, in the second reaction stage, the acrolein formed in the first reaction stage is substantially partially oxidized to acrylic acid. It is significant in this context that the industrial embodiment is normally configured in such a way that the acrolein formed in the first reaction stage is not removed, but rather conducted into the second reaction stage as a constituent of the product gas mixture leaving the first reaction stage, if appropriate supplemented by molecular oxygen and inert gas, and if appropriate cooled by direct and/or indirect cooling.

The target product or the heterogeneously catalyzed gas phase partial oxidation of propene to acrolein is acrolein.

A problem in all heterogeneously catalyzed gas phase partial oxidations in a fixed catalyst bed is that the reaction gas mixture, as it flows through the fixed catalyst bed, passes through a maximum value, known as the hotspot value. This hotspot value is composed of the external heating of the fixed catalyst bed and of the heat of reaction.

For reasons of convenience, the temperature of the fixed catalyst bed and the effective temperature of the fixed catalyst bed are therefore distinguished from one another. The temperature of the fixed catalyst bed refers to the temperature of the fixed catalyst bed when the partial oxidation process is being performed, but in the theoretical absence of a chemical reaction (i.e. without the influence of the heat of reaction). In contrast, the effective temperature of the fixed catalyst bed refers to the actual temperature of the fixed catalyst bed including the heat of reaction of the partial oxidation. When the temperature of the fixed catalyst bed is not constant along the fixed catalyst bed (for example in the case of a plurality of temperature zones), the term temperature of the fixed catalyst bed means the (numerical) average of the temperature along the fixed catalyst bed. The temperature of the fixed catalyst bed over its length may of course also be configured in such a way that the temperature is constant over a certain length, then changes abruptly and maintains this new value over a further length, etc. In that case, reference is made to a fixed catalyst bed (fixed bed catalyst charge) having more than one temperature zone (or else reaction zone), or disposed in more than one temperature zone (or else reaction zone). Catalyst-charged reactors which implement such temperature zones (or else reaction zones) are correspondingly referred to as one-zone or multizone reactors (cf., for example, WO 04/085369). In common with the temperature of the reaction gas mixtures, the effective temperature of the fixed catalyst bed likewise passes through the hotspot value in flow direction of the reaction gas mixture.

One aim of the heterogeneously catalyzed partial gas phase oxidations of propylene to acrolein is thus to configure the hotspot temperature and with it its sensitivity toward an increase in the temperature of the fixed catalyst bed in a very favorable manner. Thus, excessively high hotspot temperatures generally reduce the lifetime of the fixed catalyst bed and the selectivity of target product formation (here: acrolein). Lower hotspot temperatures are normally accompanied by a reduction in the sensitivity thereof toward an increase in the temperature of the fixed catalyst bed. For example, when the partial oxidation is carried out in tube bundle reactors, this is found to be favorable when the individual catalyst tubes, as a consequence of temperature gradients existing over the reactor cross section, cause different temperatures of the catalyst bed disposed in the particular catalyst tube. A presence of propane in the reaction gas mixture results in lower hotspot temperatures as a consequence of the comparatively increased specific heat of the propane (cf., for example, EP-A 293 224).

In addition, a presence of propane, owing to its combustibility, promotes the explosion behavior of the reaction gas mixture (for example DE-A 195 08 558).

On the other hand, it is known that a presence of propane in the reaction gas mixture promotes the undesired formation of propionaldehyde and/or propionic acid in an undesired manner (cf., for example, WO 01/96270). WO 01/96270 therefore recommends the dilution of the reaction gas mixture with molecular nitrogen and the use of air, for example, as the oxygen source. One advantage of this procedure will simultaneously be the use of a comparatively economic oxygen source. A further objective of the processes in the prior art is to be able to use, as the propene source, a heterogeneously catalyzed oxydehydrogenation and/or dehydrogenation of propane to propylene and at the same time to dispense with a subsequent removal of the propylene formed from the unconverted propane in order thus to have available an economically viable propylene source (cf., for example, WO 03/011804, DE-A 198 37 517, DE-A 198 37 519, DE-A 198 37 520, WO 01/96370, DE-A 102 45 585 and WO 03/76370).

For this purpose, WO 01/96270 recommends a heterogeneously catalyzed propane dehydrogenation with comparatively low propane conversions.

On the other hand, for example, both EP-A 990 636 and EP-A 10 70 700 require maximum propene contents in the starting reaction gas mixture of a propene partial oxidation to acrolein in order to achieve maximum space-time yields of target product.

High propane conversions do indeed promote the possibility of establishing increased propylene contents in the starting reaction gas mixture of the propylene partial oxidation. However, they are disadvantageous in that firstly the remaining propane fraction is reduced, which has an unfavorable effect on the hotspot formation and the explosion behavior, and the secondary component formation (for example $H_2$ or $H_2O$) accompanying the dehydrogenation or oxydehydrogenation simultaneously increases with high propane conversions. When the resulting dehydrogenation and/or oxydehydrogenation mixture is used in this case as such for the generation of the starting reaction gas mixture of the subsequent propylene partial oxidation, as recommended, for example, by EP-A 117 146, DE-A 33 13 573 and U.S. Pat. No. 3,161,670, the result is a comparatively voluminous starting reaction gas mixture. From the point of view of maximum economic viability of the conveying of the reaction gas streams, however, small volumes are advantageous. This is especially true where high hourly space velocities on the catalyst charge according to the principle laid down in the documents WO 04/85365, WO 04/85367, WO 04/85369, WO 04/85370, WO 04/85363, WO 00/53559, WO 04/85362, WO 00/53557 and DE-A 199 48 248 are to be realized.

On the other hand, high dehydrogenation or oxydehydrogenation conversions are favorable for the purposes of very economically viable propylene generation. Conversely, an increased propene content in the starting reaction gas mixture entails an increased molar ratio of molecular oxygen to propylene therein in order to allow the activity of the catalyst charge to be developed optimally.

At the same time, too high a residual oxygen content in the product gas mixture of partial oxidation is found to be disadvantageous in that, in the case of an advantageous recycling of the residual gas which comprises unconverted propane and remains after removal of the target product from this product gas mixture into the heterogeneously catalyzed propane dehydrogenation employed for propylene generation, it undesirably attacks the propane to be dehydrogenated and lowers the selectivity of propene formation. Generally, preference is given to a heterogeneously catalyzed propane dehydrogenation over a heterogeneously catalyzed propane oxydehydrogenation.

In contrast to the exothermic heterogeneously catalyzed oxydehydrogenation which is forced by the presence of oxygen and in which free hydrogen is neither formed as an intermediate (the hydrogen pulled from the propane is pulled out directly as water ($H_2O$)) nor is detectable, a heterogeneously catalyzed dehydrogenation refers to a ("conventional") dehydrogenation whose thermal character, in contrast the oxydehydrogenation, is endothermic (an exothermic hydrogen combustion may be included in the heterogeneously catalyzed dehydrogenation as a subsequent step) and in which free molecular hydrogen is formed at least as an intermediate. This generally requires different reaction conditions and different catalysts from the oxydehydrogenation.

In this document, fresh propane refers to propane which has not yet taken part in any chemical reaction. In general, it will be crude propane (which preferably fulfills the specification according to DE-A 102 46 119 and DE-A 102 45 585) which also comprises small amounts of components other than propane.

In this document, the starting reaction gas mixture for the propene partial oxidation to acrolein appropriately likewise fulfills the specifications recommended in DE-A 102 46 119 and DE-A 102 45 585.

The hourly space velocity on a catalyst bed, catalyzing a reaction step, of (starting) reaction gas mixture refers in this document to the amount of (starting) reaction mixture in standard liters (=l (STP); the volume in liters that the appropriate amount of (starting) reaction gas mixture would take up under standard conditions (° C., 1 bar)) which is conducted per hour through one liter of fixed catalyst bed.

The hourly space velocity may also be based only one constituent of the (starting) reaction gas mixture. In that case, it is the amount of this constituent in l (STP)/l·h which is conducted through one liter of fixed catalyst bed per hour (pure inert material charges are not included in the fixed catalyst bed).

In this document, an inert gas refers to a reaction gas constituent which behaves substantially inertly under the conditions of the appropriate reaction and, each inert reaction gas constituent viewed alone, remains chemically unchanged to an extent of more than 95 mol %, preferably to an extent of more than 99 mol %.

A disadvantage of the recommendations, compiled above, of the prior art for a heterogeneously catalyzed partial oxidation of propene to acrolein is that they each highlight only individual aspects. It is therefore an object of the present invention to provide an improved process for the heterogeneously catalyzed partial oxidation of propene to acrolein, which takes into account the different individual aspects detailed in the prior art in their entirety in an optimizing manner.

SUMMARY OF THE INVENTION

Figure 1:
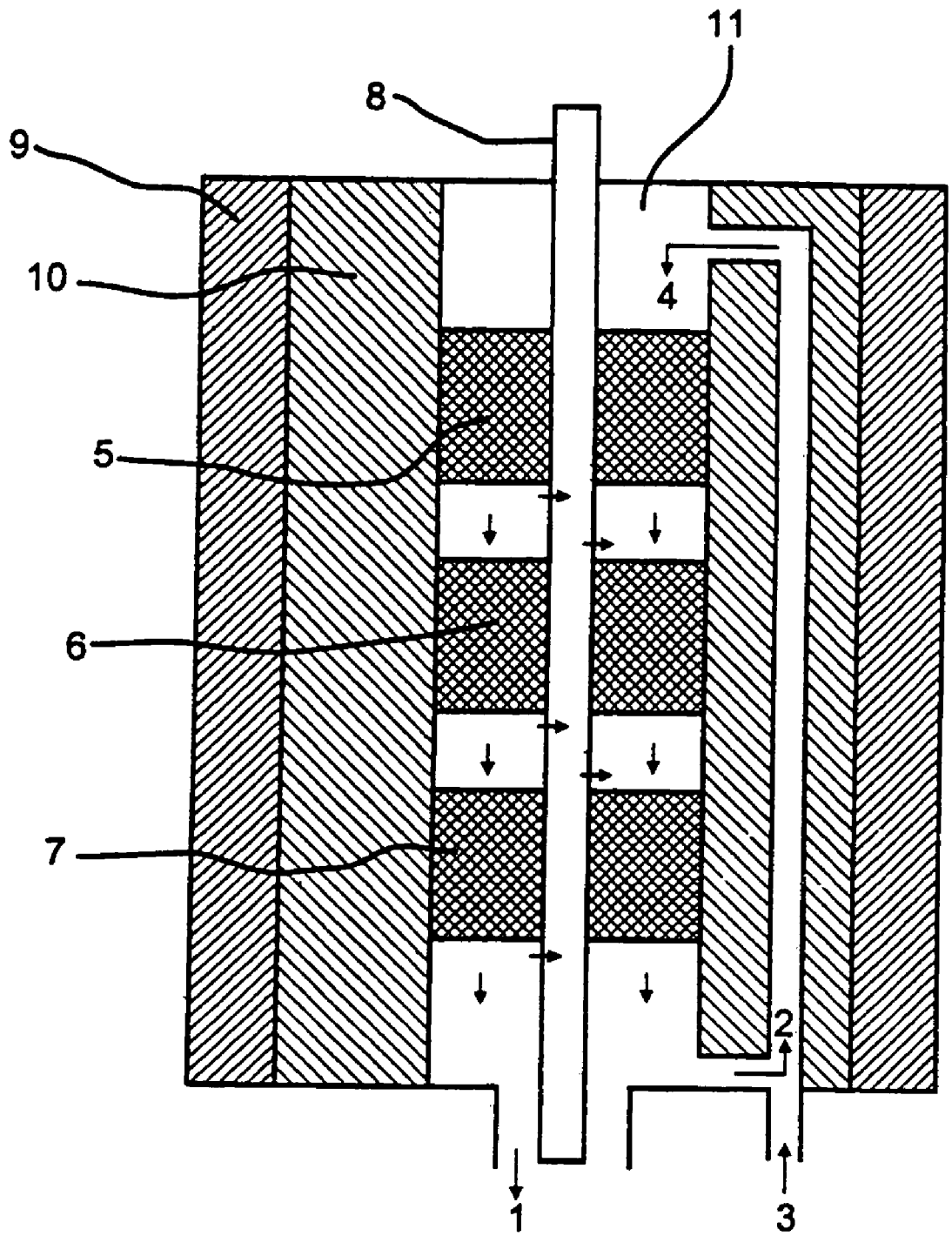
FIG. 1 shows a tray loop reactor in which the present invention can be carried out.

Accordingly, a process has been found for preparing acrolein or acrylic acid or a mixture thereof by heterogeneously catalyzed partial gas phase oxidation of propene, in which a starting reaction gas mixture 2 which comprises the propylene and molecular oxygen reactants and the inert molecular nitrogen and propane diluent gases and comprises the molecular oxygen and the propylene in a molar $O_2:C_3H_6$ ratio of $\geq 1$ is conducted at elevated temperature through a fixed catalyst bed whose active composition is at least one multimetal oxide comprising the elements Mo, Fe and Bi, wherein starting reaction gas mixture 2, based on its total volume, has the following contents:

| | |
|---|---|
| from 6 to 9% by volume of | propylene, |
| from 8 to 18% by volume of | molecular oxygen, |
| from 6 to 30% by volume of | propane and |
| from 32 to 72% by volume of | molecular nitrogen, | with the proviso that the molar ratio $V_1$, of propane present in starting reaction gas mixture 2 to propylene present in starting reaction gas mixture 2 is from 1 to 4, the molar ratio $V_2$ of molecular nitrogen present in starting reaction gas mixture 2 to molecular oxygen present in starting reaction gas mixture 2 is from 2 to 6 and the molar ratio of molecular oxygen present in starting reaction gas mixture 2 to propylene present in starting reaction gas mixture 2 is from 1.3 to 2.4.

The process according to the invention differs from the processes of the prior art in particular by the requirement that $V_1$=from 1 to 4. In all working examples of the prior art, $V_1$ is $\geq 4.5$. The latter has a disadvantageous effect on the selectivity of by-product formation of propionaldehyde and propionic acid and restricts the possible conversion of a heterogeneously catalyzed propane dehydrogenation as the propylene source without being indispensable with a view to the explosion behavior.

DESCRIPTION OF THE PREFERRED EMBODIMENTS

Preferably in accordance with the invention, the contents of starting reaction gas mixture 2 are

| | |
|---|---|
| from 7 to 9% by volume of | propylene, |
| from 9.8 to 16% by volume of | molecular oxygen, |
| from 9 to 25% by volume of | propane and |
| from 35 to 65% by volume of | molecular nitrogen, | with the proviso that
$V_1$=from 1 to 3.5
$V_2$=from 3 to 4.5 and
$V_3$=from 1.4 to 2.2.

More preferably in accordance with the invention, the contents of starting reaction gas mixture 2 are

| | |
|---|---|
| from 7 to 9% by volume of | propylene, |
| from 9.8 to 15% by volume of | molecular oxygen, |
| from 10.5 to 20% by volume of | propane and |
| from 40 to 60% by volume of | molecular nitrogen, | with the proviso that
$V_1$=from 1.5 to 2.5
$V_2$=from 3.5 to 4.5 (preferably from 3.5 to 4)
$V_3$=from 1.4 to 2.14 (preferably from 1.5 to 2.0).

Even more preferably in accordance with the invention, the contents of starting reaction gas mixture 2 are

| | |
|---|---|
| from 7 to 9% by volume of | propylene, |
| from 9.8 to 15.5% by volume of | molecular oxygen, |
| from 10.5 to 15.5% by volume of | propane and |
| from 40 to 60% by volume of | molecular nitrogen, | with the proviso that
$V_1$=from 1.5 to 2.2
$V_2$=from 3.5 to 4.5 (preferably from 3.5 to 4) and
$V_3$=from 1.4 to 2.14 (preferably from 1.5 to 2.0).

In the embodiments of the process according to the invention which is most preferred in accordance with the invention, the contents of starting reaction gas mixture 2 are

| | |
|---|---|
| from 7 to 8% by volume of | propylene, |
| from 11.9 to 15.5% by volume of | molecular oxygen, |
| from 11.9 to 15.5% by volume of | propane and |
| from 50 to 60% by volume of | molecular nitrogen, | with the proviso that
$V_1$=from 1.7 to 2.1
$V_2$=from 3.5 to 4.5 (preferably from 3.5 to 4)
$V_3$=from 1.7 to 2.1 (preferably from 1.8 to 2.0).

In an alternative embodiment of the process according to the invention, the contents of starting reaction gas mixture 2 are

| | |
|---|---|
| from 7 to 9% by volume of | propylene, |
| from 9.8 to 15% by volume of | molecular oxygen, |
| from 21 to 28% by volume of | propane and |
| from 40 to 60% by volume of | molecular nitrogen, | with the proviso that
$V_1$=from 3 to 4
$V_2$=from 3.5 to 4.5 (preferably from 3.5 to 4)
$V_3$=from 1.4 to 2.14 (preferably from 1.5 to 2.0)

Quite generally, it is favorable for all inventive starting reaction gas mixtures 2 mentioned when their total content of constituents other than propylene, molecular oxygen, propane and molecular nitrogen is ≦10% by volume. Of this up to 10% by volume of other constituents, up to 8% by volume may be ethane and/or methane (but even otherwise, this content of ethane and methane may be present). In general, the total content in inventive starting reaction gas mixtures 2 of ethane and/or methane is, however, ≦5% by volume, usually ≦3% by volume and in many cases ≦2% by volume. Such contents of ≧0.5% by volume, as a consequence of their substantially inert behavior, are, however, entirely possible in accordance with the invention and advantageous in accordance with the invention owing to the favorable thermal conductivity of methane and ethane. Advantageously in accordance with the invention, all inventive starting reaction gas mixtures 2 mentioned comprise ≦5% by volume of water and ≦5% by volume of carbon oxides ($CO_2$ and/or CO). Particularly advantageously, all inventive starting reaction gas mixtures 2 comprise ≦3% by volume of water and ≦3% by volume of carbon oxides. The same content limits apply preferably to molecular hydrogen, whose content is particularly advantageously vanishingly small. Very particular advantageously, all inventive starting reaction gas mixtures 2 comprise ≦2% by volume of water and ≦2% by volume of carbon oxides. Water contents of ≧0.5% by volume in starting reaction gas mixture 2 are generally favorable.

It is also favorable in accordance with the invention when the total content in all of the aforementioned inventive starting reaction gas mixtures 2 of constituents other than propylene, molecular oxygen, propane and molecular nitrogen is ≦5% by volume, particularly advantageously ≦3% by volume. Particularly favorably in accordance with the invention, $V_2$ for all of the aforementioned inventive starting reaction gas mixtures is substantially 3.73. The preferred ranges $V_2$ and $V_3$ specified for the inventive starting reaction gas mixtures mentioned apply independently of one another.

It is advantageous for the process according to the invention that a useful propene source is the propylene formed in the process for the continuous heterogeneously catalyzed partial dehydrogenation and/or oxydehydrogenation of propane in the gas phase, without the propane unconverted in the heterogeneously catalyzed partial dehydrogenation and/or oxydehydrogenation having to be removed from this propylene beforehand.

In principle, all known heterogeneously catalyzed partial dehydrogenations of propane are useful for this purpose, as known, for example, from the documents WO 03/076370, WO 01/96271, EP-A 117 146, WO 03/011804, U.S. Pat. No. 3,161,670, WO 01/96270, DE-A 33 13 573, DE-A 102 45 585, DE-A 103 16 039 and from the German application DE-A 10 2004 032 129.

All dehydrogenation catalysts known for this purpose in the prior art are likewise useful. Advantageously, dehydrogenation will be effected in a fixed catalyst bed.

The dehydrogenation catalysts can be divided roughly into two groups, into those which are of oxidic nature (for example chromium oxide and/or aluminum oxide) and into those which consist of at least one generally comparatively noble metal (for example platinum) deposited onto a generally oxidic support. Dehydrogenation catalysts which may be used include all of those which are recommended in DE-A 102 19 879, WO 01/96270, EP-A 731 077, DE-A 10211275, DE-A 10131297, WO 99/46039, U.S. Pat. No. 4,788,371, EP-A-0 705 136, WO 99/29420, U.S. Pat. No. 4,220,091, U.S. Pat. Nos. 5,430,220, 5,877,369, EP-A-0 117 146, DE-A 199 37 196, DE-A 199 37 105 and DE-A 199 37 107, and also the catalyst according to example 4 of DE-A 102 19 879. In particular, the catalyst according to example 1, example 2, example 3 and example 4 of DE-A 199 37 107, the catalyst according to example 4 of DE-A 102 19 879 and the catalysts of WO 02/51547, WO 02/51540 and DE-A 102005002127 may be used.

They are dehydrogenation catalysts which comprise from 10 to 99.9% by weight of zirconium dioxide, from 0 to 60% by weight of aluminum oxide, silicon dioxide and/or titanium dioxide, and from 0.1 to 10% by weight of at least one element of the first or second main group, of an element of the third transition group, of an element of the eighth transition group of the periodic table of the elements, lanthanum and/or tin, with the proviso that the sum of the percentages by weight is 100% by weight.

Also particularly suitable is the dehydrogenation catalyst used in the examples and comparative examples of this document.

Generally, the dehydrogenation catalysts are catalyst extrudates (diameter typically from 1 to 10 mm, preferably from 1.5 to 5 mm; length typically from 1 to 20 mm, preferably from 3 to 10 mm), tablets (preferably the same dimensions as for the extrudates) and/or catalyst rings (external diameter and length in each case typically from 2 to 30 mm or to 10 mm, wall thickness appropriately from 1 to 10 mm, or to 5 mm, or to 3 mm).

In general, the dehydrogenation catalysts (especially those used by way of example in this document and those recommended in DE-A 199 37 107 (especially the exemplary catalysts of this DE-A)) are such that they are capable of catalyzing both the dehydrogenation of propane and the combustion of molecular hydrogen. In the case of a competition situation over the catalysts, the hydrogen combustion proceeds very much more rapidly in comparison to the dehydrogenation of propane.

For the performance of the heterogeneously catalyzed propane dehydrogenation, in principle all reactor types and process variants known in the prior art are useful. Descriptions of such process variants are contained, for example, in all prior art documents cited with regard to the dehydrogenations and dehydrogenation catalysts.

It is characteristic of the partial heterogeneously catalyzed dehydrogenation of propane that it proceeds endothermically. This means that the heat (energy) required for the attainment of the required reaction temperature and for the reaction has to be supplied to starting reaction gas mixture 1 (the (starting) reaction gas mixture for the heterogeneously catalyzed propane dehydrogenation will also be referred to in this document as (starting) reaction gas mixture 1) either beforehand and/or in the course of the heterogeneously catalyzed dehydrogenation. In some cases, the reaction gas mixture 1 has to draw the heat of reaction required from itself.

In addition, it is typical of heterogeneously catalyzed dehydrogenations of propane, owing to the high reaction temperatures required, that small amounts of high molecular weight organic compounds having a high boiling point, up to and including carbon, are formed and are deposited on the catalyst surface, thus deactivating it. In order to minimize this disadvantageous accompanying phenomenon, the propane-containing reaction gas mixture which is to be passed at elevated temperature over the catalyst surface for the heterogeneously catalyzed dehydrogenation can be diluted with steam. Carbon which is deposited is partly or fully eliminated under the resulting conditions by the principle of coal gasification.

Another means of eliminated deposited carbon compounds is to allow a gas comprising oxygen (appropriately in the absence of hydrocarbons) to flow through the dehydrogenation catalyst at elevated temperature from time to time (if required daily) and thus to effectively burn off the deposited carbon. However, substantial suppression of the formation of carbon deposits is also possible by adding molecular hydrogen to the propane to be dehydrogenated under heterogeneous catalysis before it is conducted over the dehydrogenation catalyst at elevated temperature.

There is of course also the possibility of adding a mixture of steam and molecular hydrogen to the propane to be dehydrogenated under heterogeneous catalysis. An addition of molecular hydrogen to the heterogeneously catalyzed dehydrogenation of propane also reduces the undesired formation of allene (propadiene), propyne and acetylene as by-products. Partial oxidation of hydrogen added in this way is likewise capable of supplying heat of reaction required.

An essential feature of the invention is that useful propene sources are also heterogeneously catalyzed partial propane dehydrogenations in which the propane conversion is from 20 to 30 mol % (based on single pass of fresh propane through the dehydrogenation). However, particularly favorable heterogeneously catalyzed partial propane dehydrogenations as propene sources of the process according to the invention are those in which the aforementioned propane conversion is from 30 to 60 mol %, preferably from 35 to 55 mol % and more preferably from 35 to 45 mol %.

For the realization of the aforementioned propane conversions, it is favorable to carry out the heterogeneously catalyzed propane dehydrogenation at a working pressure of from 0.3 to 10 bar, or advantageously to 3 bar. It is also favorable to dilute the propane to be dehydrogenated under heterogeneous catalysis with steam. Thus, the heat capacity of the water firstly balances out a portion of the effect of the endothermicity of the dehydrogenation and the dilution with steam secondly reduces the partial reactant and product pressure, which has a favorable effect on the equilibrium position of the dehydrogenation. In addition, the use of steam, as already mentioned, has an advantageous effect on the onstream time of dehydrogenation catalysts comprising noble metal, especially in the case of desired high propane conversions. If required, molecular hydrogen may also be added as a further constituent. The molar ratio of molecular hydrogen to propane in starting reaction gas mixture 1 is generally $\leq 5$. The molar ratio of steam to propane in starting reaction gas mixture 1 is appropriately from $\geq 0.05$ to 2 or to 1.

Generally, minimum amounts of steam in starting reaction gas mixture 1 are preferred and pursued. In the case of propane conversions based on fresh propane in the range from 20 to 30 mol %, the amount of steam typically present in the oxidation cycle gas which is recycled if appropriate into starting reaction gas mixture 1 is typically sufficient as the steam supply for the heterogeneously catalyzed dehydrogenation. For higher propane conversions based on fresh propane, steam is normally added additionally, which may, for example, be separated process water. Oxidation cycle gas (cf., for example, EP-A 11 80 508 and the German application DE-A 10 2004 032 129) refers typically to the residual gas which remains after a one-stage or multistage heterogeneously catalyzed gas phase partial oxidation of at least one organic compound (here: propylene and/or acrolein) when the target product has been removed more or less selectively (for example by absorption into a suitable solvent or by fractional condensation) from the product mixture of the partial oxidation. In general, it consists predominantly of the inert diluent gases used for the partial oxidation and steam typically formed as a by-product in the partial oxidation (or added as diluent gas, which is less preferred in accordance with the invention) and carbon oxides formed by undesired full oxidation.

In addition, it typically still comprises residual amounts of oxygen unconsumed in the partial oxidation and of unconverted organic starting compounds (here: propylene and/or acrolein) and very small amounts of target product.

In the case of the inventive partial oxidation, the oxidation cycle gas comprises remaining propane and is therefore advantageously recycled into the heterogeneously catalyzed propane dehydrogenaion which appropriately serves as the propylene source.

In principle, a heterogeneously catalyzed partial propane dehydrogenation functioning as the propylene source may be carried out (quasi)adiabatically and at the same time endothermically. In this case, the starting reaction gas mixture is heated generally to a temperature of from 500 to 700° C. (or from 550 to 650° C.) (for example by direct firing of the surrounding wall). In the case of adiabatic pass through the at least one catalyst bed, the reaction gas mixture will then cool by from about 30° C. to 200° C. depending on conversion and dilution. Presence of steam as a heat carrier also becomes noticeably advantageous from the point of view of an adiabatic mode. Lower reaction temperatures enable longer onstream times of the catalyst bed used. Higher reaction temperatures support increased conversions.

Appropriately from an application point of view, a heterogeneously catalyzed propane dehydrogenation as the propylene source for the process according to the invention will be realized in the form of a tray reactor.

This appropriately comprises more than one catalyst bed catalyzing the dehydrogenation in spatial succession. The catalyst bed number may be from 1 to 20, appropriately from 2 to 8, or else from 3 to 6. Increased propane conversions can be achieved increasingly readily with increasing number of trays. The catalyst beds are preferably arranged in radial or axial succession. From an application point of view, it is appropriate to use the catalyst bed in the form of a fixed bed in such a tray reactor.

In the simplest case, the fixed catalyst beds in a shaft furnace reactor are arranged axially or in the annular gaps of concentric cylindrical grids. However, it is also possible to arrange the annular gaps in segments one above another and to conduct the gas after it has passed radially through one segment into the next segment above it or below it.

Appropriately, reaction gas mixture 1 is subjected to intermediate heating in the tray reactor on its path from one catalyst bed to the next catalyst bed, for example by passing it over heat exchanger surfaces (e.g. ribs) heated by hot gases or by passing it through pipes heated by hot combustion gases.

When the tray reactor is otherwise operated adiabatically, it is sufficient for propane conversions based of fresh propane of $\leq 30$ mol %, in particular when using the catalysts described in DE-A 199 37 107, especially those of the exemplary embodiments, to conduct reaction gas mixture 1 into the dehydrogenation reactor preheated to a temperature of from 450 to 550° C. and to keep it within this temperature range inside the tray reactor. This means that the entire propane dehydrogenation can thus be realized at very low temperatures, which is found to be particularly favorable for the onstream time of the fixed catalyst beds between two regenerations. For higher propane conversions, reaction gas mixture 1 is appropriately conducted into the dehydrogenation reactor preheated to higher temperatures (these may be up to 700° C.) and kept within this elevated temperature range inside the tray reactor.

It is even more elegant to carry out the above-outlined intermediate heating in a direct way (autothermal method). To this end, a limited amount of molecular oxygen is added to reaction gas mixture 1 either before it flows through the first catalyst bed (in that case starting reaction gas mixture 1 should comprise added molecular hydrogen) and/or between the downstream catalyst beds. It is thus possible (generally catalyzed by the dehydrogenation catalysts themselves) to bring about a limited combustion of molecular hydrogen which is present in reaction gas mixture 1, has been formed in the course of the heterogeneously catalyzed propane dehydrogenation and/or has been added to reaction gas mixture 1 (in some cases accompanied to a minor extent by propane combustion) (it may also be appropriate from an application point of view to insert catalyst beds in the tray reactor which are charged with catalyst which particularly specifically (selectively) catalyzes the combustion of hydrogen (examples of useful catalysts include those of the documents U.S. Pat. Nos. 4,788,371, 4,886,928, 5,430,209, 5,530,171, 5,527,979 and 5,563,314; for example, such catalyst beds may be accommodated in the tray reactor in alternation to the beds comprising dehydrogenation catalyst). The heat of reaction released thus allows virtually isothermal operation of the heterogeneously catalyzed propane dehydrogenation in a quasi-autothermal manner (the gross exothermicity is essentially zero). As the selected residence time of the reaction gas in the catalyst bed is increased, propane dehydrogenation is thus possible at decreasing or substantially constant temperature, which enables particularly long onstream times between two regenerations (in the extreme case, to ensure autothermicity, it is also possible to only combust propane).

In general, oxygen feeding as described above should be undertaken in accordance with the invention in such a way that the oxygen content of reaction gas mixture 1, based on the amount of molecular hydrogen contained therein, is from 0.5 to 50 or to 30% by volume, preferably from 10 to 25% by volume. Useful oxygen sources include both pure molecular oxygen and oxygen diluted with inert gas, for example CO, $CO_2$, $N_2$ and/or noble gases, but especially also air (apart from oxidation cycle gas, preference is given to using exclusively air as the oxygen source). The resulting combustion gases generally have an additional diluting effect and thus promote heterogeneously catalyzed propane dehydrogenation. This is especially true of steam formed in the course of combustion.

The isothermicity of the heterogeneously catalyzed propane dehydrogenation which functions appropriately as the propylene source for the process according to the invention can be further improved by incorporating closed (for example tubular) internals which have favorably, but not necessarily, been evacuated before filling in the spaces between the catalyst beds in the tray reactor. These internals contain suitable solids or liquids which evaporate or melt above a certain temperature, thereby consuming heat, and, when the temperature falls below this value, condense again and thereby release heat.

A heterogeneously catalyzed propane dehydrogenation can of course also be realized as described in DE-A 102 11 275 (as a "loop variant"), which forms an integral part of this patent application.

In other words, it is advantageous for the process according to the invention that a process for the continuous heterogeneously catalyzed partial dehydrogenation of propane in the gas phase can function as the propylene source, in which a starting reaction gas mixture 1 which comprises the propane which is to be dehydrogenated is fed continuously to a dehydrogenation zone, starting reaction gas mixture 1 is conducted in the dehydrogenation zone through at least one fixed catalyst bed, over which molecular hydrogen and (partially) propylene are formed by catalytic dehydrogenation, at least one gas comprising molecular oxygen is added to starting reaction gas mixture 1 before and/or after entry into the dehydrogenation zone, the molecular oxygen oxidizes the molecular hydrogen present in reaction gas mixture 1 partly to steam in the dehydrogenation zone and a product gas which comprises molecular hydrogen, steam, propylene and unconverted propane is removed from the dehydrogenation zone, and wherein the product gas withdrawn from the dehydrogenation zone is divided into two portions of identical composition and one of the two portions is recycled into the dehydrogenation zone as dehydrogenation cycle gas (preferably as a constituent of starting reaction gas mixture 1), as also recommended by WO 03/076370.

In this case, oxidation cycle gas may be a constituent of starting reaction gas mixture 1 and/or, according to the teaching of the German patent application DE-A 10 2004 032 129, not added to reaction gas mixture 1 until dehydrogenation has proceeded at least partly.

When oxidation cycle gas is a constituent of starting reaction gas mixture 1, it appropriately comprises only the molecular oxygen stemming from the oxidation cycle gas.

For the process according to the invention, it is favorable in the context of the loop mode described when the amount of dehydrogenation cycle gas, based on the product gas formed in the dehydrogenation, is from 30 to 70% by volume, advantageously from 40 to 60% by volume, preferably 50% by volume.

With regard to the inventive partial oxidation, starting reaction gas mixture 1 comprises, in the case of a loop mode carried out as described, for example, in a tray reactor (tray loop reactor then=dehydrogenation zone), in the steady state appropriately:

| | |
|---|---|
| from 15 to 25% by volume | of propane, |
| from 2 to 6% by volume | of propylene, |
| from 5 to 20% by volume | of steam, |
| from 2 to 10% by volume | of molecular hydrogen, |
| from 40 to 75% by volume | of molecular nitrogen, and |
| from >0 to 3% by volume | of molecular oxygen. |

The conversion of propane (based on single pass of the aforementioned starting reaction gas mixture 1 through the tray reactor operated in loop mode) and the loop cycle gas ratio (amount of dehydrogenation cycle gas based on the total amount of product gas obtained in the dehydrogenation zone) are selected with a view to the heterogeneously catalyzed gas phase partial oxidation of propylene which follows in accordance with the invention advantageously (for example in a tray loop reactor as the dehydrogenation zone) in such a way that the product gas formed in the dehydrogenation zone comprises unconverted propane and desired propylene in a molar propene to propane ratio of from 0.25 or 0.3 to 0.5 (in some cases to 0.66). At a loop cycle gas ratio of 0.5, this corresponds to a conversion of the propane present in starting reaction gas mixture 1 based on single pass thereof through the dehydrogenation zone of from 15 to 25 mol %.

Typical hourly space velocities on the dehydrogenation catalyst beds of reaction gas mixture 1 are from 250 to 5000 $h^{-1}$ (in high-load mode even up to 40000 $h^{-1}$), preferably from 10 000 to 25 000 l (STP)/l·h, more preferably from 15 000 to 20 000 l (STP)/l·h. The corresponding hourly space velocities of propane are typically from 50 to 1000 $h^{-1}$ (in high-load mode even up to 40 000 $h^{-1}$), preferably from 2000 to 5000 l (STP)/l·h, more preferably from 3000 to 4000 l (STP)/l·h.

The dehydrogenation product gas withdrawn as a propylene source from the dehydrogenation zone (the dehydrogenation reactor), according to the reaction conditions selected for the heterogeneously catalyzed propane dehydrogenation, is at a pressure of from 0.3 to 10 bar, preferably from 1 to 3 bar, and frequently has a temperature of from 450 to 650° C., in many cases a temperature of from 500 to 600° C.

In general, it comprises propane, propene, $H_2$, $N_2$, $H_2O$, methane, ethane (the latter two usually as a consequence of thermal decomposition of a small amount of propane), ethylene, butene-1, other butenes such as isobutene, other $C_4$-hydrocarbons such as n-butane, isobutane, butadiene, etc., CO and $CO_2$, but generally also oxygenates such as alcohols, aldehydes and carboxylic acids (normally having $\leq 9$ carbon atoms). In addition, constituents arising from the oxidation cycle gas may also be present in small amounts.

While EP-A 117 146, DE-A 33 13 573 and U.S. Pat. No. 3,161,670 recommend the use of the product gas formed in the propane dehydrogenation as such to charge the inventive partial oxidation, it is advantageous for an inventive partial oxidation to remove at least a portion of the constituents other than propane and propylene present therein from the propylene-containing product gas of the propane dehydrogenation before it is used as the propene source for the inventive propylene partial oxidation. In this context, the requirements of DE-A 102 11 275 should be observed.

Advantageously in accordance with the invention, at least 50% by volume, preferably at least 75% by volume, more preferably at least 90% by volume and most preferably at least 95% by volume, of the constituents other than propane and propylene which are present in the product gas of the propane dehydrogenation will be removed before it is used as the propylene source for the inventive partial oxidation.

One means to this end which is appropriate for the inventive requirements consists, for example, in contacting (for example by simply passing it through) the preferably cooled (preferably to temperatures of from 10 to 100 or 70° C.) product gas mixture of the propane dehydrogenation, for example at a pressure of from 0.1 to 50 bar, preferably from 5 to 15 bar and a temperature of, for example, from 0 to 100° C., preferably from 20 to 40° C., with a (preferably high-boiling) organic (preferably hydrophobic) solvent in which propane and propylene are absorbed (appropriately preferentially over the other constituents of the product gas mixtures of the propane dehydrogenation). Subsequent desorption, rectification and/or stripping with a gas which behaves inertly with regard to the inventive partial oxidation and/or is required as a reactant in this partial oxidation (for example air or another mixture of molecular oxygen and inert gas) allows the propane and propylene to be recovered in purified form in a mixture and this mixture to be used as the propylene source for the partial oxidation (preference is given to proceeding as described in comparative example 1 of the German application DE-A 10 2004 032 129). The off gas of such an absorption which may comprise molecular hydrogen can, for example, be subjected again to a pressure swing adsorption and/or membrane separation (for example according to DE-A 10235419) and then, if required, the hydrogen removed can also be used.

However, the C3 hydrocarbons/C4 hydrocarbons separation factor in the aforementioned separation process is comparatively limited and frequently insufficient for the requirements described in DE-A 10245585.

As an alternative to the separation step via absorption described, preference is therefore frequently given to a pressure swing adsorption or a pressure rectification for the inventive purposes.

Suitable absorbents for the above-described absorptive removal are in principle all absorbents which are capable of absorbing propane and propylene. The absorbent is preferably an organic solvent which is preferably hydrophobic and/or high-boiling. Advantageously, this solvent has a boiling point (at a standard pressure of 1 atm) of at least 120° C., preferably of at least 180° C., preferentially of from 200 to 350° C., in particular of from 250 to 300° C., more preferably of from 260 to 290° C. Appropriately, the flashpoint (at a standard pressure of 1 bar) is above 110° C. Generally suitable as absorbents are relatively nonpolar organic solvents, for example aliphatic hydrocarbons which preferably do not contain any externally active polar group, but also aromatic hydrocarbons. Generally, it is desired that the absorbent has a very high boiling point with simultaneously very high solubility for propane and propylene. Examples of absorbents include aliphatic hydrocarbons, for example $C_8$-$C_{20}$-alkanes or alkenes, or aromatic hydrocarbons, for example middle oil fractions from paraffin distillation or ethers having bulky (sterically demanding) groups on the oxygen atom, or mixtures thereof, to which a polar solvent, for example the dimethyl 1,2-phthalate disclosed in DE-A 43 08 087 may be added. Also suitable are esters of benzoic acid and phthalic acid with straight-chain alkanols containing from 1 to 8 carbon atoms, such as n-butyl benzoate, methyl benzoate, ethyl benzoate, dimethyl phthalate, diethyl phthalate, and also what are known as heat carrier oils such as diphenyl, diphenyl ether and mixtures of diphenyl and diphenyl ether or the chlorine derivatives thereof and triarylalkenes, for example 4-methyl-4'-benzyldiphenylmethane and its isomers 2-methyl-2'-benzyldiphenylmethane, 2-methyl-4-benzyldiphenylmethane and 4-methyl-2-benzyldiphenylmethane, and mixtures of such isomers. A suitable absorbent is a solvent mixture of diphenyl and diphenyl ether, preferably in the azeotropic composition, especially of about 25% by weight of diphenyl (biphenyl) and about 75% by weight of diphenyl ether, for example the Diphyl® obtainable commercially (for example purchased from Bayer Aktiengesellschaft). Frequently, this solvent mixture comprises a solvent such as dimethyl phthalate added in an amount of from 0.1 to 25% by weight based on the entire solvent mixture. Particularly suitable absorbents are also octanes, nonanes, decanes, undecanes, dodecanes, tridecanes, tetradecanes, pentadecanes, hexadecanes, heptadecanes and octadecanes, of which tetradecanes in particular have been found to be particularly suitable. It is favorable when the absorbent used firstly fulfills the abovementioned boiling point but secondly at the same time does not have too high a molecular weight. Advantageously, the molecular weight of the absorbent is $\leq 300$ g/mol. Also suitable are the paraffin oils having from 8 to 16 carbon atoms described in DE-A 33 13 573. Examples of suitable commercial products are products sold by Haltermann, such as Halpasols i, such as Halpasol 250/340 i and Halpasol 250/275 i, and also printing ink oils under the names PKWF and Printosol. Preference is given to aromatics-free commercial products, for example those of the PKWFaf type. If they comprise a small residual aromatics content, it may advantageously be lowered by rectification and/or adsorption before the use described and suppressed to values significantly below 1000 ppm by weight.

The performance of the absorption is subject to no particular restrictions. It is possible to use all common processes and conditions known to those skilled in the art. Preference is given to contacting the gas mixture with the absorbent at a pressure of from 1 to 50 bar, preferably from 2 to 20 bar, more preferably from 5 to 15 bar, and a temperature of from 0 to 100° C., in particular from 20 to 50 or 40° C. The absorption may be undertaken either in columns or in quench apparatus. It is possible to work in cocurrent or (preferably) in countercurrent. Suitable absorption columns are, for example, tray columns (having bubble-cap and/or sieve trays), columns having structured packings (for example sheet metal packings having a specific surface area of from 100 to 1000, or to 750 $m^2/m^3$, for example Mellapak® 250 Y) and columns having random packing (for example filled with Raschig packings). However, it is also possible to use trickle and spray towers, graphite block absorbers, surface absorbers such as thick-film and thin-film absorbers, and also plate scrubbers, cross-spray scrubbers and rotary scrubbers. In addition, it may be favorable to allow the absorption to take place in a bubble column with and without internals.

The propane and the propylene may be removed from the absorbent by stripping, flash evaporation (flashing) and/or distillation.

The propane and propylene are removed from the absorbent preferably by stripping and/or desorption. The desorption may be carried out in a customary manner by a pressure and/or temperature change, preferably at a pressure of from 0.1 to 10 bar, in particular from 1 to 5 bar, more preferably from 1 to 3 bar, and a temperature of from 0 to 200° C., in particular from 20 to 100° C., more preferably from 30 to 70° C., particularly preferably from 30 to 50° C. An example of a gas suitable for the stripping is steam, but preference is given in particular to oxygen/nitrogen mixtures, for example air. When air or oxygen/nitrogen mixtures are used in which the oxygen content is above 10% by volume, it may be sensible, before and/or during the stripping process, to add a gas which reduces the explosion range. Particularly suitable for this purpose are gases having a specific heat capacity of $\geq 29$ J/mol·K at 20° C., for example methane, ethane, propane (preferred), propene, benzene, methanol, ethanol, and ammonia, carbon dioxide and water. However, preference is given in accordance with the invention to avoiding $C_4$ hydrocarbons as such additives. Particularly suitable for the stripping are also bubble columns with and without internals.

The propane and propylene may also be removed from the absorbent by a distillation or rectification, in which case the columns which are familiar to those skilled in the art and have structured packings, random packings or appropriate internals can be used. Preferred conditions in the distillation or rectification are a pressure of from 0.01 to 5 bar, in particular from 0.1 to 4 bar, more preferably from 1 to 3 bar, and a temperature (in the bottom) of from 50 to 300° C., in particular from 150 to 250° C.

Before it is used to charge the partial oxidation, a propylene source which has been obtained from the absorbent by stripping and is suitable for the subsequent partial oxidation stages may be fed to a further process stage, in order, for example, to reduce the losses of entrained absorbent (for example separation in demisters and/or depth filters) and to thus simultaneously protect the partial oxidation stages from absorbent or in order to further improve the separating action between C3/C4 hydrocarbons. Such a removal of the absorbent may be effected by all process steps known to those skilled in the art. In the context of the process according to the invention, an example of a preferred embodiment of such a removal is the quenching of the outlet stream from the stripping apparatus with water. In this case, the absorbent is scrubbed out of this laden outlet stream with water and the outlet stream is simultaneously laden with water (small amounts of water have a beneficial effect on the activity of the catalysts for the partial oxidation which follows in accordance with the invention). This scrubbing or the quenching may be effected, for example, at the top of a desorption column using a liquid collecting tray by counterspraying of water or in a dedicated apparatus.

To support the separating effect, it is possible to install internals which increase the quench surface area in the quench chamber, as are known to those skilled in the art from rectifications, absorptions and desorptions.

Water is a preferred scrubbing medium in that it normally does not interfere in the downstream at least one partial zone. After the water has scrubbed the absorbent out of the outlet stream laden with propane and propylene, the water/absorbent mixture may be fed to a phase separation and the treated, low-volume outlet stream fed directly to the partial oxidation which follows in accordance with the invention.

In a manner advantageous for the process according to the invention, it is generally possible, especially when the propylene/propane mixture has been stripped free from the absorbate by means of air, to directly obtain starting reaction gas mixtures 2 as per the claims. In the case that their propane content should not yet be satisfactory in accordance with the invention, it is possible also to add fresh propane to them before they are used for the inventive partial oxidation of the propylene present. This is then recycled in accordance with the invention via the oxidation cycle gas into the heterogeneously catalyzed dehydrogenation (as a constituent of starting reaction gas mixture 1). Around the appropriate amount of propane, the feed of fresh propane into starting reaction gas mixture 1 may then be reduced. In the extreme case, the required feed of fresh propane in the heterogeneously catalyzed propane dehydrogenation may be dispensed with fully when this feed of fresh propane is effected, before the inventive partial oxidation of propylene is carried out, fully into starting reaction gas mixture 2, whence it is then added to starting reaction gas mixture 1 for the heterogeneously catalyzed propane dehydrogenation as a remaining constituent in the oxidation cycle gas only after it has passed through the inventive partial oxidation. If appropriate, there may also be a fresh propane feed (for example as stripping gas) into a $C_3$ removal which is disposed if appropriate between heterogeneously catalyzed dehydrogenation and propylene partial oxidation When the process is a two-stage partial oxidation of propylene to acrylic acid, fresh propane may also be fed partly or fully into starting reaction gas mixture 3 (however, starting reaction gas mixture 3 is sometimes already not explosive when this qualification was actually true for starting reaction gas mixture 2). This is advantageous in particular because an undesired side reaction of propane to propionaldehyde and/or propionic acid starts in particular from the first reaction stage under its conditions. It is also advantageous to divide a fresh propane feed substantially uniformly between the second and the third reaction stage.

As a result of this possibility of feeding fresh propane into starting reaction gas mixture 2 and/or 3, the composition of starting reaction gas mixture 2 and 3 can reliably be made nonexplosive. If appropriate, a portion of oxidation cycle gas may, for this purpose, also be recycled directly into the propylene and/or acrolein partial oxidation. If required, a mixture of fresh propane and oxidation cycle gas may also be used for this purpose. A decisive factor in answering the question of whether starting reaction gas mixture 2 or 3 is explosive or not is whether combustion (ignition, explosion) initiated by a local ignition source (for example glowing platinum wire) spreads in the starting reaction gas mixture 2 or 3 under certain starting conditions (pressure, temperature) or not (cf. DIN51649 and the investigation description in WO 04/007405). When there is spread, the mixture shall be referred to here as explosive. When there is no spread, the mixture is classified as nonexplosive in this document. When starting reaction gas mixture 2 or 3 is nonexplosive, this also applies to the reaction gas mixtures 2 and 3 formed in the course of the inventive partial oxidation of propylene (cf. WO 04/007405).

In other words, the process according to the invention comprises in particular a process according to the invention for preparing acrolein or acrylic acid or a mixture thereof by heterogeneously catalyzed partial gas phase oxidation of propylene, which comprises in a preceding first stage, subjecting propane as a constituent of a starting reaction gas mixture 1 to a partial heterogeneously catalyzed dehydrogenation in the gas phase to form a product gas mixture 1 which comprises propylene and unconverted propane;

if appropriate removing a portion (advantageously at least 50% by volume, with advantage at least 75% by volume, more preferably at least 90% by volume and even more preferably at least 95% by volume and at best 100% by volume) of the constituents other than propane and propylene present in the product gas mixture 1, comprising propylene and unconverted propane, of the preceding stage and then using it as a constituent of starting reaction gas mixture 2 of a preparation of acrolein or acrylic acid or a mixture thereof as the target product by the heterogeneously catalyzed partial gas phase oxidation (one-stage or two-stage) of the propylene present in starting reaction gas mixture 2;

removing target product (acrolein or acrylic acid or a mixture thereof) in a removal stage from the product gas mixture 2 or 3 obtained in the partial oxidation of propylene and recycling at least unconverted propane which remains into the preceding first stage of the partial heterogeneously catalyzed propane dehydrogenation (preference is given to recycling the entire amount of residual gas remaining in the target product removal as oxidation cycle gas into the preceding first stage).

In particular, the present invention relates to an advantageous embodiment of the above process, in which the propane required for the process (fresh propane) is supplied fully to starting reaction gas mixture 1.

The present invention further relates to an advantageous embodiment of the above process, in which the propane required for the process (fresh propane) is supplied at most partly (for example only to an extent of 75%, or only to an extent of 50%, or only to an extent of 25%) to starting reaction gas mixture 1 and at least partly (generally the remaining amount, if appropriate the entire amount) is supplied to starting reaction gas mixture 2 (and/or to starting reaction gas mixture 3). Otherwise, the procedure may be as described in WO 01/96170, which forms an integral part of this application.

In a manner known per se, the heterogeneously catalyzed gas phase partial oxidation of propylene to acrylic acid with molecular oxygen proceeds in principle in two steps successive along the reaction coordinate, of which the first leads to acrolein, and the second from acrolein to acrylic acid.

This reaction sequence in two steps successive in time opens up the possibility in a manner known per se of terminating the process according to the invention at the stage of acrolein (the stage of predominant acrolein formation) and undertaking the target product removal at this stage, or continuing the process according to the invention up to predominant acrylic acid formation and only then undertaking the target product removal.

When the process according to the invention is carried out up to predominant acrylic acid formation, it is advantageous in accordance with the invention to perform the process in two stages, i.e. in two oxidation stages arranged in series, in which case the fixed catalyst bed to be used and preferably also the other reaction conditions, for example the temperature of the fixed catalyst bed, are appropriately adjusted in an optimizing manner in each of the two oxidation stages.

Although the multimetal oxides comprising the elements Mo, Fe, Bi which are particularly suitable as active compositions for the catalysts of the first oxidation stage (propylene→acrolein) are also suitable to a certain extent for catalyzing the second oxidation stage (acrolein→acrylic acid), preference is normally given for the second oxidation stage to catalysts whose active composition is at least one multimetal oxide comprising the elements Mo and V.

The process according to the invention for the heterogeneously catalyzed partial oxidation of propylene over fixed catalyst beds whose catalysts have, as an active composition, at least one multimetal oxide comprising the elements Mo, Fe and Bi is thus suitable in particular as a one-stage process for preparing acrolein (and acrylic acid if appropriate) or as the first reaction stage for the two-stage preparation of acrylic acid.

The realization of the one-stage heterogeneously catalyzed partial oxidation of propylene to acrolein and acrylic acid if appropriate or the two-stage heterogeneously catalyzed partial oxidation of propylene to acrylic acid using an inventive starting reaction gas mixture 2 may specifically be carried out as described in the documents EP-A 70 07 14 (first reaction stage; as described there, but also in corresponding countercurrent mode of salt bath and starting reaction gas mixture over the tube bundle reactor), EP-A 70 08 93 (second reaction stage; as described there, but also in corresponding countercurrent mode), WO 04/085369 (especially this document is regarded as being an integral part of this document) (as a two-stage process), WO 04/85363, DE-A 103 13 212 (first reaction stage), EP-A 11 59 248 (as a two-stage process), EP-A 11 59 246 (second reaction stage), EP-A 11 59 247 (as a two-stage process), DE-A 199 48 248 (as a two-stage process), DE-A 101 01 695 (one-stage or two-stage), WO 04/085368 (as a two-stage process), DE 10 2004 021 764 (two-stage), WO 04/085362 (first reaction stage), WO 04/085370 (second reaction stage), WO 04/085365 (second reaction stage), WO 04/085367 (two-stage), EP-A 99 06 36, EP-A 10 07 007 and EP-A 11 06 598.

This is especially true of all working examples contained in these documents. They may be carried out as described in these documents, but with the difference that the starting reaction gas mixture used for the first reaction stage (propylene to acrolein) is an inventive starting reaction gas mixture 2. Regarding the remaining parameters, the procedure is as in the working examples of the documents mentioned (especially regarding the fixed catalyst beds and reactant hourly space velocity on the fixed catalyst beds). When the procedure in the aforementioned working examples of the prior art are in two stages and there is secondary oxygen (secondary air) feeding between the two reaction stages, the feeding is undertaken in an appropriate manner, but is adjusted in its amount to the effect that the molar ratio of molecular oxygen to acrolein in the charge gas mixture of the second reaction stage corresponds to that in the working examples of the documents mentioned.

Multimetal oxide catalysts particularly suitable for the particular reaction stage have been described many times before and are well known to those skilled in the art. For example, EP-A 25 34 09 refers on page 5 to corresponding U.S. patents.

Favorable catalysts for the particular oxidation stage are also disclosed by DE-A 4 431 957, DE-A 10 2004 025 445 and DE-A 4 431 949. This is especially true of those of the general formula I in the two aforementioned documents. Particularly advantageous catalysts for the particular oxidation stage are disclosed by the documents DE-A 103 25 488, DE-A 103 25 487, DE-A 103 53 954, DE-A 103 44 149, DE-A 103 51 269, DE-A 103 50 812, DE-A 103 50 822.

For the inventive reaction stage for the heterogeneously catalyzed gas phase partial oxidation of propylene to acrolein or acrylic acid, useful multimetal oxide compositions are in principle all multimetal oxide compositions comprising Mo, Bi and Fe as the active composition.

These are in particular the multimetal oxide active compositions of the general formula I of DE-A 199 55 176, the multimetal oxide active compositions of the general formula I of DE-A 199 48 523, the multimetal oxide active compositions of the general formulae I, II and III of DE-A 101 01 695, the multimetal oxide active compositions of the general formulae I, II and III of DE-A 199 48 248 and the multimetal oxide active compositions of the general formulae I, II and III of DE-A 199 55 168 and also the multimetal oxide active compositions specified in EP-A 70 07 14.

Also suitable for this oxidation step are the multimetal oxide catalysts comprising Mo, Bi and Fe which are disclosed in the documents DE-A 100 46 957, DE-A 100 63 162, DE-C 3 338 380, DE-A 199 02 562, EP-A 15 565, DE-C 2 380 765, EP-A 8 074 65, EP-A 27 93 74, DE-A 330 00 44, EP-A 575897, U.S. Pat. No. 4,438,217, DE-A 19855913, WO 98/24746, DE-A 197 46 210 (those of the general formula II), JP-A 91/294239, EP-A 293 224 and EP-A 700 714. This applies in particular to the exemplary embodiments in these documents, and among these particular preference is given to those of EP-A 15565, EP-A 575897, DE-A 197 46 210 and DE-A 198 55 913. Particular emphasis is given in this context to a catalyst according to example 1c from EP-A 15 565 and also to a catalyst to be prepared in a corresponding manner but whose active composition has the composition $Mo_{12}Ni_{6.5}Zn_2Fe_2Bi_1P_{0.0065}K_{0.06}O_x \cdot 10SiO_2$. Emphasis is also given to the example having the serial number 3 from DE-A 198 55 913 (stoichiometry: $Mo_{12}CO_7Fe_3Bi_{0.6}K_{0.08}Si_{1.6}O_x$) as an unsupported hollow cylinder catalyst of geometry 5 mm×3 mm×2 mm (external diameter×height×internal diameter) and also to the unsupported multimetal oxide II catalyst according to example 1 of DE-A 197 46 210. Mention should also be made of the multimetal oxide catalysts of U.S. Pat. No. 4,438,217. The latter is especially true when these hollow cylinders have a geometry of 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Further possible catalyst geometries in this context are extrudates (for example length 7.7 mm and diameter 7 mm; or length 6.4 mm and diameter 5.7 mm).

A multitude of the multimetal oxide active compositions suitable for the step from propylene to acrolein and, if appropriate, acrylic acid can be encompassed by the general formula IV

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in IV other than oxygen.

They are obtainable in a manner known per se (see, for example, DE-A 4 023 239) and are customarily shaped in substance to give spheres, rings or cylinders or else used in the form of coated catalysts, i.e. preshaped inert support bodies coated with the active composition. They may of course also be used as catalysts in powder form.

In principle, active compositions of the general formula IV can be prepared in a simple manner by obtaining a very intimate, preferably finely divided dry mixture having a composition corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature. Useful sources for the elemental constituents of the multimetal oxide active compositions IV are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture).

The starting compounds for preparing multimetal oxide active compositions IV can be intimately mixed in dry or in wet form. When they are mixed in dry form, the starting compounds are appropriately used as finely divided powders and subjected to calcination after mixing and optional compacting. However, preference is given to intimate mixing in wet form. Typically, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The multimetal oxide active compositions of the general formula IV may be used for the "propylene→acrolein (and acrylic acid if appropriate)" step either in powder form or shaped to certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of suitable unsupported catalyst geometries include solid cylinders or hollow cylinders having an external diameter and a length of from 2 to 10 mm. In the case of the hollow cylinder, a wall thickness of from 1 to 3 mm is advantageous. The unsupported catalyst can of course also have spherical geometry, and the spherical diameter can be from 2 to 10 mm.

A particularly favorable hollow cylinder geometry is 5 mm×3 mm×2 mm (external diameter×length×internal diameter), especially in the case of unsupported catalysts.

The pulverulent active composition or its pulverulent precursor composition which is yet to be calcined and/or partially calcined may of course also be shaped by applying to preshaped inert catalyst supports. The coating of the support bodies to produce the coated catalysts is generally performed in a suitable rotatable vessel, as disclosed, for example, by DE-A 2 909 671, EP-A 293 859 or EP-A 714 700. To coat the support bodies, the powder composition to be applied is appropriately moistened and dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are the customary porous or nonporous aluminum oxides, silicon dioxide, thorium dioxide, zirconium dioxide, silicon carbide or silicates such as magnesium silicate or aluminum silicate. They generally behave substantially inertly with regard to the target reaction on which the process according to the invention is based. The support bodies can have a regular or irregular shape, although preference is given to regularly shaped support bodies having distinct surface roughness, for example spheres or hollow cylinders. Suitable support bodies are substantially nonporous, surface-roughened spherical supports made of steatite whose diameter is from 1 to 10 mm or to 8 mm, preferably from 4 to 5 mm. However, suitable support bodies are also cylinders whose length is from 2 to 10 mm and whose external diameter is from 4 to 10 mm. In the case of rings suitable in accordance with the invention as support bodies, the wall thickness is also typically from 1 to 4 mm. Annular support bodies to be used with preference in accordance with the invention have a length of from 2 to 6 mm, an external diameter of from 4 to 8 mm and a wall thickness of from 1 to 2 mm. Support bodies suitable in accordance with the invention are in particular also rings of geometry 7 mm×3 mm×4 mm (external diameter×length×internal diameter). The fineness of the catalytically active oxide compositions to be applied to the surface of the support body is of course adjusted to the desired coating thickness (cf. EP-A 714 700).

Multimetal oxide active compositions to be used for the step from propylene to acrolein are also compositions of the general formula V $$[Y^1_{a'}Y^2_{b'}O_{x'}]_p[Y^3_{c'}Y^4_{d'}Y^5_{e'}Y^6_{f'}Y^7_{g'}Y^2_{h'}O_{y'}]_q \qquad (V)$$

in which the variables are each defined as follows:
$Y^1$=only bismuth or bismuth and at least one of the elements tellurium, antimony, tin and copper,
$Y^2$=molybdenum or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from >0 to 20,
f'=from 0 to 6,
g'=from 0 to 15,
h'=from 8 to 16,
x',y'=numbers which are determined by the valency and frequency of the elements in V other than oxygen and
p,q=numbers whose p/q ratio is from 0.1 to 10, comprising three-dimensional regions of the chemical composition $Y^1_{a'}Y^2_{b'}O_{x'}$ which are delimited from their local environment owing to their different composition from their local environment, and whose maximum diameter (longest direct line passing through the center of the region and connecting two points on the surface (interface) of the region) is from 1 nm to 100 μm, frequently from 10 nm to 500 nm or from 1 μm to 50 or 25 μm.

Particularly advantageous inventive multimetal oxide compositions V are those in which $Y^1$ is only bismuth.

Among these, preference is given in turn to those of the general formula VI $$[Bi_{a''}Z^2_{b''}O_{x''}]_{p''}[Z^2_{12}Z^3_{c''}Z^4_{d''}Fe_{e''}Z^5_{f''}Z^6_{g''}Z^7_{h''}O_{y''}]_{q''} \qquad (VI)$$

in which the variables are each defined as follows:
$Z^2$=molybdenum or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a''=from 0.1 to 1,
b''=from 0.2 to 2,
c''=from 3 to 10,
d''=from 0.02 to 2,
e''=from 0.01 to 5, preferably from 0.1 to 3,
f''=from 0 to 5,
g''=from 0 to 10,
h'' from 0 to 1,
x'',y''=numbers which are determined by the valency and frequency of the elements in VI other than oxygen,
p'',q''=numbers whose p''/q'' ratio is from 0.1 to 5, preferably from 0.5 to 2, and very particular preference is given to those compositions VI in which $Z^2_{b''}$=(tungsten)$_{b''}$ and $Z^2_{12}$=(molybdenum)$_{12}$.

It is also advantageous when at least 25 mol % (preferably at least 50 mol % and more preferably 100 mol %) of the total proportion of $[Y^1_{a'}Y^2_{b'}O_{x'}]_{p'}$ ($[Bi_{a''}Z^2_{b''}O_{x''}]_{p''}$) of the multimetal oxide compositions V (multimetal oxide compositions VI) suitable in accordance with the invention in the multimetal oxide compositions V (multimetal oxide compositions VI) suitable in accordance with the invention is in the form of three-dimensional regions of the chemical composition $Y^1_{a'}Y^2_{b'}O_{x'}$ [$Bi_{a''}Z^2_{b''}O_{x''}$] which are delimited from their local environment owing to their different chemical composition from their local environment, and whose maximum diameter is in the range from 1 nm to 100 μm.

With regard to the shaping, the statements made for the multimetal oxide composition IV catalysts apply to multimetal oxide composition V catalysts.

The preparation of multimetal oxide active compositions V is described, for example, in EP-A 575 897 and also in DE-A 198 55 913.

The inert support materials recommended above are also useful, inter alia, as inert materials for the dilution and/or delimitation of the appropriate fixed catalyst beds, or as a preliminary bed which protects them and/or heats the gas mixture.

It should be mentioned at this point that all catalysts and multimetal oxide compositions which have been recommended as suitable for the step from propylene to acrolein are in principle also suitable for the partial ammoxidation of propylene to acrylonitrile.

For the second step (the second reaction stage), the heterogeneously catalyzed gas phase partial oxidation of acrolein to acrylic acid, useful active compositions are, as already stated, in principle all multimetal oxide compositions containing Mo and V, for example those of DE-A 100 46 928.

A multitude thereof, for example those of DE-A 198 15 281, can be encompassed by the general formula VII $$Mo_{12}V_aX^1_bX^2_cX^3_dX^4_eX^5_fX^6_gO_n \qquad (VII)$$

in which the variables are each defined as follows:
$X^1$=W, Nb, Ta, Cr and/or Ce,
$X^2$=Cu, Ni, Co, Fe, Mn and/or Zn,
$X^3$=Sb and/or Bi
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in VII other than oxygen.

Embodiments which are preferred in accordance with the invention among the active multimetal oxides VII are those which are encompassed by the following definitions of the variables of the general formula VII:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5, b=from 0.5 to 2,
c=from 0.5 to 3,
d=from 0 to 2,
e=from 0 to 0.2,
f=from 0 to 1 and
n=a number which is determined by the valency and frequency of the elements in VII other than oxygen.

However, multimetal oxides VII which are very particularly preferred in accordance with the invention are those of the general formula VIII $$Mo_{12}V_{a'}Y^1_{b'}Y^2_{c'}Y^5_{f'}Y^6_{g'}O_{n'} \qquad (VIII)$$

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements in VIII other than oxygen.

The multimetal oxide active compositions (VII) which are suitable in accordance with the invention are obtainable in a manner known per se, for example disclosed in DE-A 43 35 973 or in EP-A 714 700.

In principle, multimetal oxide active compositions suitable for the "acrolein→acrylic acid" step, especially those of the general formula VII, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions VII include those compounds which are already oxides and/or those compounds which can be converted to oxides by heating, at least in the presence of oxygen.

The starting compounds for the preparation of multimetal oxide compositions VII can be intimately mixed in dry or in wet form. When they are mixed in dry form, the starting compounds are appropriately used in the form of finely divided powder and subjected to calcining after mixing and, if appropriate, compaction. However, preference is given to intimate mixing in wet form.

This is typically done by mixing the starting compounds with one another in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, especially those of the general formula VII, may be used for the acrolein oxidation either in powder form or shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinders, a wall thickness of from 1 to 3 mm is appropriate. The unsupported catalyst may of course also have spherical geometry, in which case the spherical diameter may be from 2 to 10 mm (e.g. 8.2 mm or 5.1 mm).

The pulverulent active composition or its pulverulent precursor composition which is yet to be calcined can of course also be shaped by applying to preshaped inert catalyst supports. The coating of the support bodies to prepare the coated catalysts is generally performed in a suitable rotatable vessel, as disclosed, for example, by DE-A 2 909 671, EP-A 293 859 or by EP-A 714 700.

To coat the support bodies, the powder composition to be applied is appropriately moistened and is dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders with grit layer. Suitable support bodies include substantially nonporous, surface-roughened, spherical supports made of steatite, whose diameter is from 1 to 10 mm or to 8 mm, preferably from 4 to 5 mm. In other words, suitable spherical geometries may have diameters of 8.2 mm or 5.1 mm. However, suitable support bodies also include cylinders whose length is from 2 to 10 mm and whose external diameter is from 4 to 10 mm. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Suitable support bodies are also in particular rings of geometry 7 mm×3 mm×4 mm (external diameter×length×internal diameter). The fineness of the catalytically active oxide compositions to be applied to the surface of the support body is of course adapted to the desired coating thickness (cf. EP-A 714 700).

Favorable multimetal oxide active compositions to be used for the "acrolein→acrylic acid" step are also compositions of the general formula IX $$[D]_p[E]_q \qquad (IX)$$

in which the variables are each defined as follows:
$D=Mo_{12}V_{a''}Z^1_{b''}Z^2_{c''}Z^3_{d''}Z^4_{e''}Z^5_{f''}Z^6_{g''}O_{x''}$,
$E=Z^7_{12}Cu_{h''}H_{i''}O_{y''}$,
$Z^1$=W, Nb, Ta, Cr and/or Ce,
$Z^2$=Cu, Ni, Co, Fe, Mn and/or Zn,
$Z^3$=Sb and/or Bi,
$Z^4$=Li, Na, K, Rb, Cs and/or H, $Z^5$=Mg, Ca, Sr and/or Ba,
$Z^6$=Si, Al, Ti and/or Zr,
$Z^7$=Mo, W, V, Nb and/or Ta, preferably Mo and/or W,
a"=from 1 to 8,
b"=from 0.2 to 5,
c"=from 0 to 23,
d"=from 0 to 50,
e"=from 0 to 2,
f"=from 0 to 5,
g"=from 0 to 50,
h"=from 4 to 30,
i"=from 0 to 20 and
x",y"=numbers which are determined by the valency and frequency of the elements in IX other than oxygen and
p,q=numbers other than zero whose p/q ratio is from 160:1 to 1:1, and which are obtainable by separately preforming a multimetal oxide composition E

  (E)

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the abovementioned elements in the stoichiometry D

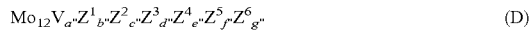  (D)

(starting composition 2) in the desired p:q ratio, drying the aqueous mixture which may result, and calcining the resulting dry precursor composition before or after drying at temperatures of from 250 to 600° C. to give the desired catalyst geometry.

Preference is given to the multimetal oxide compositions IX in which the preformed solid starting composition 1 is incorporated into an aqueous starting composition 2 at a temperature of <70° C. A detailed description of the preparation of multimetal oxide composition VI catalysts is contained, for example, in EP-A 668 104, DE-A 197 36 105, DE-A 100 46 928, DE-A 197 40 493 and DE-A 195 28 646.

With regard to the shaping, the statements made for the multimetal oxide composition VII catalysts apply to multimetal oxide composition IX catalysts.

Multimetal oxide catalysts which are outstandingly suitable for the "acrolein→acrylic acid" step are also those of DE-A 198 15 281, especially having multimetal oxide active compositions of the general formula I of this document.

Advantageously, unsupported catalyst rings are used for the step from propylene to acrolein and coated catalyst rings for the step from acrolein to acrylic acid.

The performance of the process according to the invention, from propylene to acrolein (and acrylic acid if appropriate), may be carried out with the catalysts described, for example, in a single-zone multiple catalyst tube fixed bed reactor, as described by DE-A 4 431 957. In this case, starting reaction gas mixture 2 and heat carrier (heat exchange medium) may be conducted in cocurrent or in countercurrent viewed over the reactor.

The reaction pressure is typically in the range from 1 to 3 bar and the overall space velocity on the fixed catalyst bed of (starting) reaction gas mixture is preferably from 1500 to 4000 or 6000 l (STP)/l·h or more. The propylene loading (the propylene hourly space velocity on the fixed catalyst bed) is typically from 90 to 200 l (STP)/l·h or to 300 l (STP)/l·h or more. Propylene loadings above 135 l (STP)/l·h or ≧140 l (STP)/l·h, or ≦150 l (STP)/l·h, or ≧160 l (STP)/l·h are particularly preferred in accordance with the invention, since the inventive starting reaction gas mixture 2 causes favorable hotspot behavior (all of the aforementioned applies irrespective of the specific selection of the fixed bed reactor).

The flow to the single-zone multiple catalyst tube fixed bed reactor of the charge gas mixture is preferably from above. The heat exchange medium used is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$).

Viewed over the reactor, salt melt and reaction gas mixture may be conducted either in cocurrent or in countercurrent. The salt melt itself is preferably conducted in a meandering manner around the catalyst tubes.

When the flow to the catalyst tubes is from top to bottom, it is appropriate to charge the catalyst tubes with catalyst from bottom to top as follows (for the flow from bottom to top, the charge sequence is appropriately reversed):

first, to a length of from 40 to 80 or to 60% of the catalyst tube length, either only catalyst or a mixture of catalyst and inert material, the latter, based on the mixture, making up a proportion by weight of up to 20% by weight (section C);

following this, to a length of from 20 to 50 or to 40% of the total tube length, either only catalyst or a mixture of catalyst and inert material, the latter, based on the mixture, making up a proportion by weight of up to 40% by weight (section B); and finally, to a length of from 10 to 20% of the total tube length, a bed of inert material (section A) which is preferably selected such that it causes a very small pressure drop.

Section C is preferably undiluted.

The aforementioned charge variant is especially appropriate when the catalysts used are those according to Example 1 of DE-A 100 46 957 or according to Example 3 of DE-A 100 46 957 and the inert material used is steatite rings having the geometry 7 mm×7 mm×4 mm (external diameter×height× internal diameter). With regard to the salt bath temperature, the statements of DE-A 4431957 apply.

However, the performance of the first step of the partial oxidation, from propylene to acrolein (and acrylic acid if appropriate), may also be carried out with the catalysts described, for example, in a two-zone multiple catalyst tube fixed bed reactor, as described by DE-A 199 10 506. In both of the above-described cases (and quite generally in the process according to the invention), the propene conversion achieved in single pass is normally at values of ≧90 mol %, or ≧95 mol %, and the selectivity of acrolein formation at values of ≧90 mol %. Advantageously in accordance with the invention, the inventive partial oxidation of propylene to acrolein, or acrylic acid or mixtures thereof, is effected advantageously as described in EP-A 1 159244 und most preferably as described in WO 04/085363 and in WO 04/085362, but with the difference that the starting reaction gas mixture used is an inventive starting reaction gas mixture 2. In particular, all working examples of the aforementioned documents may be carried out as described in these documents, but employing a starting reaction gas mixture 2 as the charge gas mixture, especially with the starting reaction gas mixtures 2 listed as particularly preferred and as exemplary.

The documents EP-A 1159244, WO 04/085363 and WO 04/085362 are regarded as being an integral part of this document.

In other words, the inventive partial oxidation of propylene to acrolein can be carried out particularly advantageously over a fixed catalyst bed having increased propylene hourly space velocity and at least two temperature zones.

In other words, an advantageous embodiment of the inventive partial oxidation of propylene to acrolein, or acrylic acid or a mixture thereof, is a process according to the invention in which starting reaction gas mixture 2 is conducted over (through) a fixed catalyst bed 2 whose active composition is at least one multimetal oxide comprising the elements Mo, Fe and Bi, with the proviso that the propylene conversion on single pass is ≧90 mol % and the associated selectivity of acrolein formation and of acrylic acid by-product formation taken together is ≧90 mol % and wherein a) the hourly space velocity on the fixed catalyst bed of propene present in starting reaction gas mixture 2 is ≧160 l (STP) of propene/l of fixed catalyst bed ·h
b) the fixed catalyst bed consists of one fixed catalyst bed arranged in two spatially successive reaction zones A*, B*, the temperature of reaction zone A* being from 300 to 390° C. and the temperature of reaction zone B* being from 305 to 420° C. and at the same time at least 5° C. above the temperature of reaction zone A*,
c) starting reaction gas mixture 2 flows through reaction zones A*, B* in the time sequence "first A*", "then B*" and
d) reaction zone A* extends up to a conversion of propene of from 40 to 80 mol %.

Otherwise, reference is made to EP-A 1159244.

This also means that a very particularly preferred embodiment of the inventive partial oxidation of propylene to acrolein, or acrylic acid or a mixture thereof, is a process according to the invention in which starting reaction gas mixture 2 is conducted over a fixed catalyst bed whose active composition is at least one multimetal oxide comprising the elements Mo, Fe and Bi, with the proviso that the fixed catalyst bed is arranged in two spatially successive temperature zones A, B,
both the temperature of temperature zone A and the temperature of temperature zone B are a temperature in the range from 290 to 380° C.,
the fixed catalyst bed consists of at least two spatially successive fixed catalyst bed zones, the volume-specific activity within a fixed catalyst bed zone being substantially constant and increasing in flow direction of reaction gas mixture 2 at the transition from one fixed catalyst bed zone into another fixed catalyst bed zone, and said increase preferably being sharp (step increase),
temperature zone A extends up to a conversion of propene of from 40 to 80 mol %,
the propene conversion in single pass of starting reaction gas mixture 2 through the entire fixed catalyst bed is ≧90 mol % and the selectivity of acrolein formation based on converted propene is ≧90 mol %,
the time sequence in which reaction gas mixture 2 flows through temperature zones A, B corresponds to the alphabetic sequence of the temperature zones,
the hourly space velocity on the fixed catalyst bed of propene present in starting reaction gas mixture 2 is ≧90 l (STP) of propene/l of fixed catalyst bed ·h, and
the difference $T^{maxA}-T^{maxB}$, formed from the highest temperature $T^{maxA}$ that reaction gas mixture 2 has within temperature zone A and the highest temperature $T^{maxB}$ that reaction gas mixture 2 has within temperature zone B is ≧0° C.,
and, optionally more preferred, in the process, the transition from temperature zone A into temperature zone B in the fixed catalyst bed does not coincide with a transition from one fixed catalyst bed zone into another fixed catalyst bed zone.

Further details of this procedure can be found in WO 04/085362 which is an integral part of this document, and also in the further course of this document in the description of the particularly preferred two-stage partial oxidation of propylene to acrylic acid.

The performance of the second step in the case of a two-stage partial oxidation of propylene to acrolein, i.e. the partial oxidation of acrolein to acrylic acid, may be carried out with the catalysts described, for example, in a one-zone multiple catalyst tube fixed bed reactor as described in DE-A 44 31 949. In this reaction stage, reaction gas mixture 3 and heat carrier can be conducted in cocurrent viewed over the reactor. In general, the product gas mixture of the preceding inventive propylene partial oxidation to acrolein may in principle be conducted as such (if appropriate after intermediate cooling (this may be effected indirectly or directly by, for example, secondary air addition) thereof), i.e. without secondary component removal, into the second reaction stage, i.e. into the acrolein partial oxidation.

The molecular oxygen required for the second step, the acrolein partial oxidation, may already be present in the starting reaction gas mixture 2 for the inventive propylene partial oxidation to acrolein. However, it may also be added partly or fully directly to the product gas mixture of the first reaction stage (this is preferably effected in the form of (secondary) air, but may also be effected in the form of pure oxygen or of mixtures of inert gas or oxygen). Irrespective of the procedure, the charge gas mixture (starting reaction gas mixture 3) of such an inventive partial oxidation of acrolein to acrylic acid advantageously has, in principle for the same reasons as the inventive partial oxidation of propylene to acrolein, or acrylic acid or a mixture thereof, the following contents:

| | |
|---|---|
| from 4.5 to 8% by volume of | acrolein, |
| from 2.25 or 4.5 to 9% by volume of | molecular oxygen, |
| from 6 to 30% by volume of | propane, |
| from 32 to 72% by volume of | molecular nitrogen, |
| from 5 to 15% by volume of | steam. |

Starting reaction gas mixture 3 preferably has the following contents:

| | |
|---|---|
| from 5.5 to 8% by volume of | acrolein, |
| from 2.75 or 5.5 to 9% by volume of | molecular oxygen, |
| from 10 to 25% by volume of | propane, |
| from 40 to 70% by volume of | molecular nitrogen, |
| from 5 to 15% by volume of | steam. |

Starting reaction gas mixture 3 most preferably has the following contents:

| | |
|---|---|
| from 6 to 8% by volume of | acrolein (preferably from 6 to 7% by volume) |
| from 3 or 6 to 9% by volume of | molecular oxygen, |
| from 10 to 20% by volume of | propane (preferably from 10 to 16% by volume) |
| from 50 to 65% by volume of | molecular nitrogen, |
| from 7 to 13% by volume of | steam, | the preferred ranges applying independently of one another, but advantageously being realized simultaneously.

Quite generally, it is favorable for all inventive starting reaction gas mixtures 3 mentioned when their total content of components other than the above-specified constituents is $\leq 10\%$ by volume, preferably $\leq 8\%$ by volume, more preferably $\leq 6$ or $\leq 5\%$ by volume and most preferably $\leq 4\%$ by volume. Particularly advantageously, the total content in starting reaction gas mixture 3 of carbon oxides is $\leq 5\%$ by volume and most advantageously $\leq 3\%$ by volume or $\leq 2\%$ by volume.

The content in starting reaction gas mixture 3 of propylene is preferably $\leq 2\%$ by volume and more advantageously $\leq 1\%$ by volume.

It is also advantageous for starting reaction gas mixture 3 when the molar ratio of molecular oxygen present in the starting reaction gas mixture 3 to acrolein present in starting reaction gas mixture 3 is $\geq 0.5$ and $\leq 2$, advantageously $\geq 1$ and $\leq 1.75$, more advantageously $\geq 1$ and $\leq 1.5$ and most advantageously $\geq 1$ and $\leq 1.25$.

It is also advantageous for starting reaction gas mixture 3 when the molar ratio of propane present therein to acrolein present therein is from 1 to 4, with preference from 1.5 to 3.5, more preferably from 1.5 to 3 and most preferably from 1.5 or 2 to 2.5.

The content in starting reaction gas mixture 3 of methane and/or ethane will generally be $\leq 8\%$ by volume, usually $\leq 5\%$ by volume and typically $\leq 3\%$ by volume or $\leq 2\%$ by volume. However, it will frequently advantageously be $\geq 0.5\%$ by volume.

As in the first reaction stage, the reaction pressure in the second reaction stage too is typically in the range from 1 to 3 bar and the total space velocity on the fixed catalyst bed of (starting) reaction gas mixture 3 is preferably from 1500 to 4000 or 6000 l (STP)/l·h or more. The acrolein loading (the acrolein hourly space velocity on the fixed catalyst bed) is typically from 90 to 190 l (STP)/l·h, or to 290 l (STP)/l·h or more. Acrolein loadings above 135 l (STP)/l·h, or $\geq 140$ l (STP)/l·h, or $\geq 150$ l (STP)/l·h, or $\geq 160$ l (STP)/l·h are particularly preferred, since the inventive starting reaction gas mixture 3 likewise causes favorable hotspot behavior.

The acrolein conversion based on single pass of starting reaction gas mixture 3 through the fixed catalyst bed is appropriately normally $\geq 90$ mol % and the accompanying selectivity of acrylic acid formation $\geq 90$ mol %.

The flow to the single-zone multiple catalyst tube fixed bed reactor of the charge gas mixture is likewise preferably from above. The heat exchange medium used in the second stage too is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$). Viewed over the reactor, as already stated, salt melt and reaction gas mixture 3 may be conducted either in cocurrent or in countercurrent. The salt melt itself is preferably conducted in a meandering manner around the catalyst tubes.

When the flow to the catalyst tubes is from top to bottom, it is appropriate to charge the catalyst tubes with catalyst from bottom to top as follows:
first, to a length of from 50 to 80 or to 70% of the catalyst tube length, either only catalyst or a mixture of catalyst and inert material, the latter, based on the mixture, making up a proportion by weight of up to 20% by weight (section C);
following this, to a length of from 20 to 40% of the total tube length, either only catalyst or a mixture of catalyst and inert material, the latter, based on the mixture, making up a proportion by weight of up to 50 or up to 40% by weight (section B); and
finally, to a length of from 5 to 20% of the total tube length, a bed of inert material (section A) which is preferably selected such that it causes a very small pressure drop.

Section C is preferably undiluted. As is quite generally the case for the heterogeneously catalyzed gas phase partial oxidation of acrolein to acrylic acid (especially at high acrolein loadings on the fixed catalyst bed and high steam contents of the charge gas mixture), section B may also consist of two successive catalyst dilutions (for the purpose of minimizing hotspot temperature and hotspot temperature sensitivity). From bottom to top, first with up to 20% by weight of inert material and subsequently with from >20% by weight to 50 or to 40% by weight of inert material. Section C is then preferably undiluted.

For flow to the catalyst tubes from bottom to top, the catalyst tube charge is appropriately reversed.

The aforementioned charge variant is especially appropriate when the catalysts used are those according to preparation example 5 of DE-A 100 46 928 or those according to DE-A 198 15 281 and the inert material used is steatite rings having the geometry 7 mm×7 mm×4 mm or 7 mm×7 mm×3 mm (in each case external diameter×height×internal diameter). With regard to the salt bath temperature, the statements of DE-A 443 19 49 apply. It is generally selected in such a way that the acrolein conversion achieved in single pass is normally $\geq 90$ mol %, or $\geq 95$ mol % or $\geq 99$ mol %.

However, the performance of the partial oxidation of acrolein to acrylic acid may also be carried out with the catalysts described, for example, in a two-zone multiple catalyst tube fixed bed reactor as described in DE-199 10 508. For the acrolein conversion, the above statements apply. Also in the case in which an acrolein partial oxidation as described above is carried out as the second stage of a two-stage propylene oxidation to acrylic acid in a two-zone multiple catalyst tube fixed bed reactor, the charge gas mixture (starting reaction gas mixture 3) will appropriately be obtained directly by using the product gas mixture of the partial oxidation directed to the first step (if appropriate after indirect or direct (for example by supplying secondary air) intermediate cooling thereof) (as has already been described above). The oxygen required for the acrolein partial oxidation is preferably added in the form of air (if appropriate also in the form of pure molecular oxygen or in the form of a mixture of molecular oxygen and an inert gas) and, for example, added directly to the product gas mixture of the first step of the two-stage partial oxidation (propylene→acrolein). However, it may also, as already described, already be present in the starting reaction gas mixture 2 for the first reaction stage.

In a two-stage partial oxidation of propylene to acrylic acid with direct further use of the product gas mixture of the first step of the partial oxidation to charge the second step of the partial oxidation, two one-zone multiple catalyst tube fixed bed reactors (at high reactant hourly space velocity on the catalyst bed, as is quite generally the case, preference is given to countercurrent mode between reaction gas and salt bath (heat carrier) viewed over the tube bundle reactor) or two two-zone multiple catalyst tube fixed bed reactors will generally be connected in series. A mixed series connection (one-zone/two-zone or vice versa) is also possible.

Between the reactors may be disposed an intermediate cooler which may if appropriate comprise inert beds which can perform a filter function. The salt bath temperature of multiple catalyst tube reactors for the first step of the two-stage partial oxidation of propylene to acrylic acid is generally from 300 to 400° C. The salt bath temperature of multiple catalyst tube reactors for the second step of the partial oxidation of propylene to acrylic acid, the partial oxidation of acrolein to acrylic acid, is usually from 200 to 350° C. In addition, the heat exchange media (preferably salt melts) are normally conducted through the relevant multiple catalyst tube fixed bed reactors in such amounts that the difference between their input and their output temperature is generally $\leq 5°$ C. As already mentioned, both steps of the partial oxidation of propylene to acrylic acid may also be implemented in one reactor over one charge, as described in DE-A 101 21 592.

It should also be mentioned once again that a portion of the starting reaction gas mixture 2 for the first step ("propylene→acrolein") may be oxidation cycle gas (residual gas) coming from the partial oxidation.

This is, as already stated, a gas which comprises molecular oxygen and remains after the target product removal (acrolein and/or acrylic acid removal) from the product gas mixture of the partial oxidation and may be recycled partly as inert diluent gas into the charge for the first and/or if appropriate second step of the partial oxidation of propylene to acrolein and/or acrylic acid.

However, preference is given to recycling such oxidation cycle gas comprising propane, molecular oxygen and unconverted propylene exclusively into the heterogeneously catalyzed propane dehydrogenation which, if appropriate, functions as the propylene source.

Overall, a tube bundle reactor within which the catalyst charge changes appropriately along the individual catalyst tubes with completion of the first reaction step (such two-stage propylene partial oxidations in a single reactor are taught, for example, by EP-A 91 13 13, EP-A 97 98 13, EP-A 99 06 36 and DE-A 28 30 765) forms the simplest implementation form of the two oxidation stages for the two steps of the partial oxidation from propylene to acrylic acid. If appropriate, the charge of the catalyst tubes with catalyst is interrupted by an inert material bed.

However, preference is given to implementing the two oxidation stages in the form of two tube bundle systems connected in series. These may be disposed in one reactor, in which case the transition from one tube bundle to the other tube bundle is formed by a bed of inert material which is not accommodated in the catalyst tube (and is appropriately accessible on foot). While the catalyst tubes are generally flowed around by a heat carrier, this does not reach an inert bed accommodated as described above. Advantageously, the two catalyst tube bundles are therefore accommodated in spatially separate reactors. In general, an intermediate cooler is disposed between the two tube bundle reactors in order to reduce any acrolein postcombustion proceeding in the product gas mixture which leaves the first reaction stage. The reaction temperature in the first reaction stage (propylene→acrolein) is generally from 300 to 450° C., preferably from 320 to 390° C. The reaction temperature in the first reaction stage (acrolein→acrylic acid) is generally from 200 to 370° C., frequently from 220 to 330° C. The reaction pressure in both oxidation stages is appropriately from 0.5 to 5 bar, advantageously from 1 to 3 bar. The hourly space velocity (l (STP)/l·h) on the oxidation catalysts of reaction gas in both reaction stages is frequently from 1500 to 2500 l (STP)/l·h or to 4000 l (STP)/l·h. The hourly space velocity of propylene may be from 100 to 200 or 300 and more l (STP)/l·h.

In principle, the two oxidation stages in the process according to the invention may be configured as described, for example, in DE-A 198 37 517, DE-A 199 10 506, DE-A 199 10 508 and DE-A 198 37 519.

In both reaction stages, an excess of molecular oxygen relative to the amount required in accordance with the reaction stoichiometry generally has an advantageous effect on the kinetics of the particular gas phase partial oxidation.

In principle, it is also possible to realize the inventive heterogeneously catalyzed gas phase partial oxidation of propylene to acrylic acid in a single tube bundle reactor as follows. Both reaction steps proceed in an oxidation reactor which is charged with one or more catalysts whose active composition is a multimetal oxide which comprises the elements Mo, Fe and Bi and is capable of catalyzing the reaction of both reaction steps. This catalyst charge can of course change continuously or abruptly along the reaction coordinate. Of course, it is possible in one embodiment of an inventive two-stage partial oxidation of propylene to acrylic acid in the form of two oxidation stages connected in series to partly or fully remove carbon dioxide and steam which have formed as a by-product in the first oxidation stage and are present in the product gas mixture leaving the first oxidation stage from this product gas mixture, if required, before it is passed on into the second oxidation stage. Preference is given in accordance with the invention to selecting a procedure which does not provide for such a removal.

Useful sources for intermediate oxygen feeding carried out between the two oxidation stages are, as already stated, in addition to air (preferred), either pure molecular oxygen or molecular oxygen diluted with inert gas such as $CO_2$, CO, noble gases, $N_2$ and/or saturated hydrocarbons.

In the process according to the invention, metering of, for example, cold air to hot product gas mixture 2 can also bring about cooling thereof by a direct route before it is used further as a constituent of a starting reaction gas mixture 3.

Advantageously in accordance with the invention, the partial oxidation of acrolein to acrylic acid is effected as described in EP-A 11 59 246 and most preferably as described in WO 04/085365 and in WO 04/085370. However, preference is given in accordance with the invention to using, as the acrolein-containing starting reaction gas mixture, a starting reaction gas mixture 3 (this may in particular be the product gas mixture of an inventive first-stage partial oxidation of propylene to acrolein, which has if appropriate been supplemented with sufficient secondary air that the ratio of molecular oxygen to acrolein in the resulting starting reaction gas mixture 3 is in each case from 0.5 to 1.5). In particular, all working examples of the aforementioned documents may be carried out as described in these documents, but employing a starting reaction gas mixture 3 as the charge gas mixture, especially with the starting reaction gas mixtures 3 listed in this document as particularly preferred and as exemplary. The documents EP-A 1159246, WO 04/08536 and WO 04/085370 are regarded as an integral part of this document.

In other words, the inventive partial oxidation of acrolein to acrylic acid can be carried out with increased acrolein hourly space velocity advantageously over a fixed catalyst bed 3 which has at least two temperature zones.

In other words, an advantageous embodiment of the inventive partial oxidation of acrolein to acrylic acid is a process in which starting reaction gas mixture 3 is conducted over (through) a fixed catalyst bed whose active composition is at least one multimetal oxide comprising the elements Mo and V, with the proviso that the acrolein conversion in single pass is $\geq 90$ mol % and the accompanying selectivity of acrylic acid formation is $\geq 90$ mol % and wherein a) the hourly space velocity on the fixed catalyst bed of acrolein present in starting reaction gas mixture 3 is ≧150 l (STP) of acrolein/l of fixed catalyst bed ·h,
b) the fixed catalyst bed consists of one fixed catalyst bed arranged in two spatially successive reaction zones C*, D*, the temperature of reaction zone C* being from 230 to 270° C. and the temperature of reaction zone D* being from 250 to 300° C. and at the same time at least 5° C. above the temperature of reaction zone C*,
c) starting reaction gas mixture 3 flows through reaction zones C*, D* in the time sequence "first C*", "then D*" and
d) reaction zone C* extends up to a conversion of acrolein of from 55 to 85 mol %.

Otherwise, reference is made to EP-A 1159246.

In other words, a particularly preferred embodiment of the inventive partial oxidation of acrolein to acrylic acid is also a process according to the invention in which starting reaction gas mixture 3 is conducted over a fixed catalyst bed whose active composition is at least one multimetal oxide comprising the elements Mo and V, with the proviso that the fixed catalyst bed is arranged in two spatially successive temperature zones C, D,
both the temperature of temperature zone C and the temperature of temperature zone D are a temperature in the range from 230 to 320° C.,
the fixed catalyst bed consists of at least two spatially successive fixed catalyst bed zones, the volume-specific activity within a fixed catalyst bed zone being substantially constant and increasing in flow direction of reaction gas mixture 3 at the transition from one fixed catalyst bed zone into another fixed catalyst bed zone, and said increase preferably being sharp (step increase),
temperature zone C extends up to a conversion of acrolein of from 45 to 85 mol %,
the acrolein conversion in single pass of starting reaction gas mixture 3 through the entire fixed catalyst bed is ≧90 mol % and the selectivity of acrylic acid formation based on converted acrolein is ≧90 mol %,
the time sequence in which reaction gas mixture 3 flows through temperature zones C, D corresponds to the alphabetic sequence of the temperature zones,
the hourly space velocity on fixed catalyst bed of acrolein present in starting reaction gas mixture 3 is ≧70 l (STP) of acrolein/l of fixed catalyst bed ·h, and
the difference $T^{maxC}-T^{maxD}$ formed from the highest temperature $T^{maxC}$ that reaction gas mixture 3 has within temperature zone C and the highest temperature $T^{maxD}$ that reaction gas mixture 3 has within temperature zone D, is ≧0° C., and, optionally more preferred, in the process, the transition from temperature zone C into temperature zone D in the fixed catalyst bed does not coincide with a transition from one fixed catalyst bed zone into another fixed catalyst bed zone.

Further details of this procedure can be found in WO 04/085370 which is an integral part of this document, and also in the further course of this document in the description of the particularly preferred two-stage partial oxidation of propylene to acrylic acid.

Such a particularly preferred two-stage partial oxidation of propylene to acrylic acid may advantageously be carried out as described in EP-A 1159248 and in WO 04/085367, but with the difference that the starting reaction gas mixture used for the first oxidation stage (propylene to acrolein) is an inventive starting reaction gas mixture 2 (in particular also in the working examples of EP-A 1159248 and of WO 04/085367; both documents form an integral part of this document).

In other words, an inventive starting reaction gas mixture 2 will initially be conducted in a first reaction stage over (through) a fixed catalyst bed 1 whose active composition is at least one multimetal oxide comprising the elements Mo, Fe and Bi, with the proviso that the propylene conversion in single pass is ≧90 mol % and the accompanying selectivity of acrolein formation and of acrylic acid by-product formation taken together is ≧90 mol %, the temperature of the product gas mixture 2 leaving the first reaction stage will if appropriate be reduced by indirect and/or direct cooling and molecular oxygen and/or inert gas will be added if appropriate to product gas mixture 2, and will then be conducted, as a starting reaction gas mixture 3 which comprises acrolein, molecular oxygen and at least one inert gas and comprises the molecular oxygen and the acrolein in a molar $O_2:C_3H_4O$ ratio of ≧0.5, in a second reaction stage over (through) a fixed catalyst bed 2 whose active composition is at least one multimetal oxide comprising molybdenum and vanadium, with the proviso that the acrolein conversion in single pass is ≧90 mol % and the selectivity of acrylic acid formation assessed over both reaction stages, based on propylene converted, is ≧80 mol %, and the further procedure will be such that a) the hourly space velocity on fixed catalyst bed 1 of propene present in starting reaction gas mixture 2 is ≧160 l (STP) of propene/l of fixed catalyst bed 1·h,
b) the first fixed catalyst bed consists of one fixed catalyst bed arranged in two spatially successive reaction zones A*, B*, the temperature of reaction zone A* being from 300 to 390° C. and the temperature of reaction zone B* being from 305 to 420° C. and at the same time at least 5° C. above the temperature of reaction zone A*,
c) starting reaction gas mixture 2 flows through reaction zones A*, B* in the time sequence "first A*", "then B*",
d) reaction zone A* extends up to a conversion of propene of from 40 to 80 mol %,
e) the hourly space velocity on fixed catalyst bed 2 of acrolein present in starting reaction gas mixture 3 is ≧140 l (STP) of acrolein/l of fixed catalyst bed 2·h,
f) fixed catalyst bed 2 consists of one fixed catalyst bed 2 arranged in two spatially successive reaction zones C*, D*, the temperature of reaction zone C* being from 230 to 270° C. and the temperature of reaction zone D* being from 250 to 300° C. and at the same time at least 10° C. above reaction zone C*,
g) starting reaction gas mixture 3 flows through reaction zones C*, D* in the time sequence "first C*", "then D*" and
h) reaction zone C* extends up to a conversion of propene of from 55 to 85 mol %.

Otherwise, reference is made to EP-A 11 59 248.

However, it will more preferably be carried out according to WO 04/085369 which is an integral part of this document, but with the difference that the starting reaction gas mixture used for the first oxidation stage (propylene to acrolein) is an inventive starting reaction gas mixture 2 (in particular also in the working examples of WO 04/085369).

In other words, an inventive starting reaction gas mixture 2 will first be conducted in a first reaction stage over a fixed catalyst bed 1 whose active composition is at least one multimetal oxide comprising the elements Mo, Fe and Bi, with the proviso that fixed catalyst bed 1 is arranged in two spatially successive temperature zones A, B, both the temperature of temperature zone A and the temperature of temperature zone B are a temperature in the range from 290 to 380° C., fixed catalyst bed 1 consists of at least two spatially successive fixed catalyst bed zones, the volume-specific activity within a fixed catalyst bed zone being substantially constant and increasing in flow direction of reaction gas mixture 2 at the transition from one fixed catalyst bed zone into another fixed catalyst bed zone, and said increase preferably being sharp (step increase), temperature zone A extends up to a conversion of propene of from 40 to 80 mol %, the propene conversion in single pass of starting reaction gas mixture 2 through the entire fixed catalyst bed 1 is $\geq 90$ mol % and the selectivity of acrolein formation and of acrylic acid by-product formation taken together and based on converted propene is $\geq 90$ mol %, the time sequence in which reaction gas mixture 2 flows through temperature zones A, B corresponds to the alphabetic sequence of temperature zones A, B, the hourly space velocity on fixed catalyst bed 1 of propene present in starting reaction gas mixture 2 is $\geq 90$ l (STP) of propene/l of fixed catalyst bed 1·h, and the difference $T^{maxA}-T^{maxB}$, formed from the highest temperature $T^{maxA}$ that reaction gas mixture 2 has within temperature zone A and the highest temperature $T^{maxB}$ that reaction gas mixture 2 has within temperature zone B, is $\geq 0°$ C., then the temperature of the product gas mixture 2 leaving the first reaction stage will be reduced if appropriate by cooling and molecular oxygen and/or inert gas if appropriate, preferably air if appropriate, will be added to product gas mixture 2, and it will subsequently be conducted, as a starting reaction gas mixture 3 which comprises acrolein, molecular oxygen and at least one inert gas and comprises the molecular oxygen and the acrolein in a molar $O_2:C_3H_4O$ ratio of $\geq 0.5$, in a second reaction stage over a fixed catalyst bed 2 whose active composition is at least one multimetal oxide comprising the elements Mo and V, with the proviso that fixed catalyst bed 2 is arranged in two spatially successive temperature zones C, D, both the temperature of temperature zone C and the temperature of temperature zone D are a temperature in the range from 230 to 320° C., fixed catalyst bed 2 consists of at least two spatially successive fixed catalyst bed zones, the volume-specific activity within a fixed catalyst bed zone being substantially constant and increasing in flow direction of reaction gas mixture 3 at the transition from one fixed catalyst bed zone into another fixed catalyst bed zone, and said increase preferably being sharp (step increase), temperature zone C extends up to a conversion of acrolein of from 45 to 85 mol %, the acrolein conversion in single pass of starting reaction gas mixture 3 through the entire fixed catalyst bed 2 is $\geq 90$ mol % and the selectivity of acrylic acid formation based on propene converted over both reaction stages is $\geq 80$ mol %, the time sequence in which reaction gas mixture 3 flows through temperature zones C, D corresponds to the alphabetic sequence of the temperature zones C,D, the hourly space velocity on fixed catalyst bed 2 of acrolein present in starting reaction gas mixture 3 is $\geq 70$ l (STP) of acrolein/l of fixed catalyst bed 2·h, and the difference $T^{maxC}-T^{maxD}$, formed from the highest temperature $T^{maxC}$ that reaction gas mixture 3 has within temperature zone C and the highest temperature $T^{maxD}$ that reaction gas mixture 3 has within temperature zone D, is $\geq 0°$ C., and, optionally more preferred, in the process, neither the transition from temperature zone A into temperature zone B in fixed catalyst bed 1 nor the transition from temperature zone C into temperature zone D in fixed catalyst bed 2 coincides with a transition from one fixed catalyst bed zone into another fixed catalyst bed zone.

In this document, the temperature of a temperature zone refers to the temperature of the portion of the fixed catalyst bed disposed in the temperature zone when the process according to the invention is being performed, but in the absence of a chemical reaction. When this temperature is not constant within the temperature zone, the term temperature of a temperature zone refers to the (numerical) mean of the temperature of the fixed catalyst bed along the reaction zone. It is essential in this context that the individual temperature zones are heated substantially independent of one another.

Since both the heterogeneously catalyzed partial gas phase oxidation of propene to acrolein and the heterogeneously catalyzed partial gas phase oxidation of acrolein to acrylic acid are markedly exothermic reactions, both the temperature of reaction gas mixture 2 and the temperature of reaction gas mixture 3 in reactive pass through fixed catalyst bed 1 and fixed catalyst bed 2 respectively are generally different from the temperature of a temperature zone. They are normally above the temperature of the temperature zone and generally pass through a maximum (hotspot maximum) or fall starting from a maximum value within a temperature zone.

In general, the difference $T^{maxA}-T^{maxB}$ in the process according to the invention will not be more than 80° C. According to the invention, $T^{maxA}-T^{maxB}$ is preferably $\geq 3°$ C. and $\geq 70°$ C. With very particular preference, $T^{maxA}-T^{maxB}$ in the process according to the invention is $\geq 20°$ C. and $\leq 60°$ C.

When the process according to the invention is being performed in the case of relatively low ($\geq 90$ l (STP)/l·h and $\geq 160$ l (STP)/l·h) propene hourly space velocities on the fixed catalyst bed, the $T^{maxA}-T^{maxB}$ differences required according to the invention are normally attained when, firstly, both the temperature of reaction zone A and the temperature of reaction zone B are in the range from 290 to 380° C. and, secondly, the difference between the temperature of reaction zone B ($T_B$) and the temperature of reaction zone A ($T_A$), i.e., $T_B-T_A$, is $\leq 0°$ C. and $\geq -20°$ C. or $\geq -10°$ C. or $\leq 0°$ C. and $\geq -5°$ C., or frequently $\leq 0°$ C. and $\geq -3°$ C.

When the process according to the invention is being performed under increased (preferred in accordance with the invention) propene hourly space velocities ($\geq 160$ l (STP)/l·h and $\leq 300$ l (STP)/l·h, or $\leq 600$ l (STP)/l·h), the $T^{maxA}-T^{maxB}$ differences required according to the invention are normally attained when, firstly, both the temperature of reaction zone A and the temperature of reaction zone B are in the range from 290 to 380° C. and $T_B-T_A$ is $\geq 0°$ C. and $\leq 50°$ C., or $\geq 5°$ C. and $\leq 45°$ C., or $\geq 10°$ C. and $\leq 40°$ C., or $\geq 15°$ C. and $\leq 30°$ C. or $\leq 35°$ C. (e.g. 20° C. or 25° C.).

The above statement regarding the $T_B-T_A$ temperature differences regularly also applies when the temperature of reaction zone A is within the preferred range of from 305 to 365° C. or within the particularly preferred range of from 310 to 340° C.

The propene hourly space velocity on fixed catalyst bed 1 in the process described may therefore be, for example, $\geq 90$ l (STP)/l·h and $\leq 300$ l (STP)/l·h, or $\geq 110$ l (STP)/l·h and $\leq 280$ l (STP)/l·h or $\geq 130$ l (STP)/l·h and $\leq 260$ l (STP)/l·h, or ≧150 l (STP)/l·h and ≦240 l (STP)/l·h, or ≧170 l (STP)/l·h and ≦220 l (STP)/l·h, or ≧190 l (STP)/l·h and ≦200 l (STP)/l·h.

According to the invention, temperature zone A preferably extends up to a propene conversion of from 50 to 70 mol % or from 60 to 70 mol %.

In general, the difference $T^{maxC}-T^{maxD}$ in the process according to the invention will not be more than 75° C. According to the invention, $T^{maxC}-T^{maxD}$ is preferably ≧3° C. and ≦60° C. With very particular preference, $T^{maxC}-T^{maxD}$ in the process according to the invention is ≧5° C. and ≦40° C.

When the process according to the invention is being performed in the case of relatively low (≧70 l (STP)/l·h and ≦150 l (STP)/l·h) acrolein hourly space velocities on fixed catalyst bed 2, the $T^{maxC}-T^{maxD}$ differences required according to the invention are normally attained when, firstly, both the temperature of reaction zone C and the temperature of reaction zone D are in the range from 230 to 320° C. and, secondly, the difference between the temperature of reaction zone D ($T_D$) and the temperature of reaction zone C ($T_C$), i.e., $T_D-T_C$, is ≦0° C. and ≧-20° C. or ≧-10° C. or ≦0° C. and ≧-5° C., or frequently ≦0° C. and ≧-3° C.

When the process according to the invention is being performed under increased propene hourly space velocities and thus also increased acrolein hourly space velocities (≧150 l (STP)/l·h and ≦300 l (STP)/l·h, or ≦600 l (STP)/l·h), the $T^{maxC}-T^{maxD}$ differences required according to the invention are normally attained when, firstly, both the temperature of reaction zone C and the temperature of reaction zone D are in the range from 230 to 320° C. and $T_D-T_C$ is ≧0° C. and ≦40° C., or ≧5° C. and ≦35° C., or 30° C., or ≧10° C. and ≦25° C., or ≦20° C., or ≦15° C.

The above statement regarding the $T_D-T_C$ temperature differences regularly also applies when the temperature of reaction zone C is within the preferred range of from 250 to 300° C. or within the particularly preferred range of from 260 to 280° C.

The acrolein hourly space velocity on fixed catalyst bed 2 in the process according to the invention may therefore be, for example, ≧70 l (STP)/l·h or ≧90 l (STP)/l·h and ≦300 l (STP)/l·h, or ≧110 l (STP)/l·h and ≦280 l (STP)/l·h or ≧130 l (STP)/l·h and ≦260 l (STP)/l·h, or ≧150 l (STP)/l·h and ≦240 l (STP)/l·h, or ≧170 l (STP)/l·h and ≦220 l (STP)/l·h, or ≧190 l (STP)/l·h and ≦200 l (STP)/l·h.

According to the invention, temperature zone C preferably extends up to an acrolein conversion of from 50 to 85 mol % or from 60 to 85 mol %.

The working pressure in both reaction stages of the process according to the invention may be either below standard pressure (e.g. down to 0.5 bar) or above standard pressure. Typically, the working pressure in both reaction stages of the process according to the invention will be at values of from 1 to 5 bar, frequently from 1 to 3 bar.

Normally, the reaction pressure will not excess 100 bar in either of the two reaction stages.

In general, the propene conversion of fixed catalyst bed 1 based on single pass in the procedure described will be ≧92 mol % or ≧94 mol %. The selectivity of product-of-value formation (sum of acrolein formation and acrylic acid by-product formation) in the case of suitable selection (see catalysts recommended in this document) of fixed catalyst bed 1 in a manner known per se will regularly be ≧92 mol %, or ≧94 mol %, frequently ≧95 mol %, or ≧96 mol % or ≧97 mol %.

In general, the acrolein hourly space velocity on fixed catalyst bed 2 in the above-described process will additionally be about 10 l (STP)/l·h, frequently about 20 or 25 l (STP)/l·h, below the propene hourly space velocity on fixed catalyst bed 1. This can be attributed primarily to the fact that neither the conversion of propene nor the selectivity of acrolein formation generally reach 100%.

In general, the acrolein conversion of fixed catalyst bed 2 based on single pass in the above-described process will be ≧92 mol %, or ≧94 mol %, or ≧96 mol %, or ≧98 mol % and frequently even ≧99 mol % or more.

In the case of suitable selection of fixed catalyst beds 1 and 2 in a manner known per se (see catalyst recommendations given in this document), the selectivity of acrylic acid formation assessed over both reaction stages in the above-described procedure, based on converted propene, will be at values of ≧83 mol %, frequently at ≧85 mol %, or ≧88 mol %, often at ≧90 mol %, or ≧93 mol %.

It is essential for the procedure described that fixed catalyst bed 1 consists of at least two spatially successive fixed catalyst bed zones, the volume-specific activity within one fixed catalyst bed zone being substantially constant and increasing sharply at the transition from one fixed catalyst bed zone into another fixed catalyst bed zone in flow direction of reaction gas mixture 1.

The volume-specific (i.e. normalized to the unit of the particular bed volume) activity of a fixed catalyst bed zone can then be adjusted over the fixed catalyst bed zone in a substantially constant manner by starting from a basic amount of shaped catalyst bodies prepared in a uniform manner (their bed corresponds to the maximum achievable volume-specific activity) and homogeneously diluting it in the particular fixed catalyst bed zone with shaped bodies (shaped diluent bodies) which behave substantially inertly with regard to the heterogeneously catalyzed partial gas phase oxidation. The higher the proportion of shaped diluent bodies selected, the less the amount of active composition and catalyst activity is present in a certain volume of the bed. Useful materials for such inert shaped diluent bodies are in principle all of those which are suitable as support material for coated catalysts suitable in accordance with the invention.

Useful such materials include, for example, porous or non-porous aluminum oxides, silicon dioxide, thorium dioxide, zirconium dioxide, silicon carbide, silicates such as magnesium silicate or aluminum silicate or the steatite already mentioned (e.g. Steatite C-220 from CeramTec).

The geometry of such inert shaped diluent bodies may in principle be as desired. In other words, they may, for example, be spheres, polygons, solid cylinders or else rings. According to the invention, the inert shaped diluent bodies selected will preferably be those whose geometry corresponds to that of the shaped catalyst bodies to be diluted with them.

According to the invention, it is favorable when the chemical composition of the active composition used does not vary over the entire fixed catalyst bed 1. In other words, although the active composition used for a single shaped catalyst body can be a mixture of different multimetal oxides comprising the elements Mo, Fe and Bi, the same mixture then has to be used for all shaped catalyst bodies of fixed catalyst bed 1.

A volume-specific activity increasing zone by zone over the fixed catalyst bed in flow direction of reaction gas mixture 2 can therefore be achieved for the process according to the invention in a simple manner, for example, by beginning the bed in a first fixed catalyst bed zone with a high proportion of inert shaped diluent bodies based on one type of shaped catalyst bodies, and then reducing this proportion of shaped diluent bodies zone by zone in flow direction.

However, a zone by zone increase in the volume-specific activity is also possible, for example, by increasing the thickness of the active composition layer applied to the support zone by zone at constant geometry and active composition type of a coated shaped catalyst body or, in a mixture of coated catalysts having the same geometry but having different proportions by weight of the active composition by increasing the proportion of shaped catalyst bodies having higher active composition content zone by zone. Alternatively, the active compositions themselves can be diluted in the course of the active composition preparation by, for example, incorporating inert, diluting materials such as hard-fired silica into the dry mixture of starting compounds to be calcined. Different amounts of diluting material added lead automatically to different activities. The more diluting material is added, the lower the resulting activity will be. A similar effect can also be achieved, for example, in the case of mixtures of unsupported catalysts and of coated catalysts (having identical active composition) by varying the mixing ratio in an appropriate manner. A variation in the volume-specific activity can also be achieved by the use of catalyst geometries having different bulk density (for example, in the case of unsupported catalysts having identical active composition of the different geometries). It is of course also possible to use the variants described in combination.

It is of course also possible to use mixtures of catalysts having chemically different active compositions and, as a consequence of this different composition, having different activity for fixed catalyst bed 1. These mixtures may in turn, zone by zone, be varied in their composition and/or be diluted with different amounts of inert shaped diluent bodies.

Upstream and/or downstream of fixed catalyst bed 1 may be disposed beds consisting exclusively of inert material (for example only shaped diluent bodies) (in this document, they are not included for terminology purposes in fixed catalyst bed 1, since they do not comprise any shaped bodies which have multimetal oxide active composition). The shaped diluent bodies used for the inert bed may have the same geometry as the shaped catalyst bodies used in fixed catalyst bed 1. However, the geometry of the shaped diluent bodies used for the inert bed may also be different to the abovementioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having a diameter d=4-5 mm. Temperature zones A and B in the process according to the invention may also extend to the inert beds. According to the invention, it is advantageous when neither temperature zone A nor temperature zone B covers more than three fixed catalyst bed zones (according to the invention, at least one fixed catalyst bed zone is necessarily covered by both temperature zones).

According to the invention, it is particularly advantageous when the entire fixed catalyst bed comprises not more than five, appropriately not more than four or three, fixed catalyst bed zones.

According to the invention, at the transition from one fixed catalyst bed zone to another fixed catalyst bed zone (in flow direction of reaction gas mixture 2) of fixed catalyst bed 1, the volume-specific active composition (i.e. the weight of the multimetal oxide active composition present in a uniform bed volume) should (in the case of uniform active composition over the entire fixed catalyst bed 1) appropriately increase by at least 5% by weight, preferably by at least 10% by weight (this applies in particular in the case of uniform shaped catalyst bodies over the entire fixed catalyst bed 1). In general, this increase in the process according to the invention will not be more than 50% by weight, usually not more than 40% by weight. According to the invention, in the case of uniform active composition over the entire fixed catalyst bed 1, the difference in the volume-specific active composition of the fixed catalyst bed zone having the lowest volume-specific activity and the fixed catalyst bed zone having the highest volume-specific activity should also not be more than 50% by weight, preferably not more than 40% by weight, and generally not more than 30% by weight.

In the process according to the invention, fixed catalyst bed 1 will frequently consist of only two fixed catalyst bed zones.

According to the invention, preference is given to the last fixed catalyst bed zone of fixed catalyst bed 1 in flow direction of reaction gas mixture 2 being undiluted. In other words, it preferably consists exclusively of shaped catalyst bodies. If required, it may also consist of a bed of shaped catalyst bodies whose volume-specific activity is reduced, for example by dilution with inert material, for example by 10%.

When fixed catalyst bed 1 consists of only two fixed catalyst bed zones, it is generally advantageous in accordance with the invention (as is quite generally the case in the process according to the invention) when the fixed catalyst bed zone having the highest volume-specific activity does not project into temperature zone A (in particular when the heating in temperature zone A and temperature zone B is effected by means of a flowing heat carrier which in each case flows in countercurrent to the reaction gas mixture). In other words, the fixed catalyst bed zone having the lower volume-specific activity will favorably project into temperature zone B and the fixed catalyst bed zone having the higher volume-specific activity will begin and end in temperature zone B (i.e. have its beginning beyond the transition from temperature zone A to temperature zone B).

When fixed catalyst bed 1 consists of only three fixed catalyst bed zones, it is generally equally advantageous according to the invention when the fixed catalyst bed zone having the higher volume-specific activity does not project into temperature zone A but begins and ends in temperature zone B, i.e. has its beginning beyond the transition from temperature zone A to temperature zone B (in particular when the heating in temperature zone A and temperature zone B is effected by means of a flowing heat carrier which in each case flows in countercurrent to the reaction gas mixture). In other words, the fixed catalyst bed zone having the second highest volume-specific activity will normally project into both temperature zone A and temperature zone B.

When fixed catalyst bed 1 consists of four fixed catalyst bed zones, it is generally advantageous in accordance with the invention when the fixed catalyst bed zone having the third highest volume-specific activity projects into both temperature zone A and into temperature zone B (in particular when the heating in temperature zone A and temperature zone B is effected by means of a flowing heat carrier which in each case flows in countercurrent to reaction gas mixture 2).

In the case of cocurrent flow of reaction gas mixture and heat carriers in temperature zones A and B, it may be advantageous in the process according to the invention when the fixed catalyst bed zone having the highest volume-specific activity within fixed catalyst bed 1 projects into temperature zone A.

Generally, the volume-specific activity between two fixed catalyst bed zones of a fixed catalyst bed 1 can be differentiated experimentally in a simple manner by passing the same reaction gas mixture comprising propene, under identical boundary conditions (preferably the conditions of the contemplated process), over fixed catalyst beds of the same length, but in each case each according to the composition of the particular fixed catalyst bed zone. The higher amount of propene converted indicates the higher volume-specific activity.

When the total length of fixed catalyst bed 1 is $L^1$, it is advantageous in accordance with the invention if there is no transition from one fixed catalyst bed zone to another fixed catalyst bed zone within the region of $$X^1 \pm L^1 \frac{4}{100}$$

or within the region of $$X^1 \pm L^1 \frac{3}{100}$$

or within the region of $$X^1 \pm L^1 \frac{2}{100},$$

where X is the location (the position) within fixed catalyst bed 1 of the transition from temperature zone A to temperature zone B.

Preference is given to fixed catalyst bed 1 in the above-described process being structured as follows in flow direction of reaction gas mixture 2.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of fixed catalyst bed 1, a homogeneous mixture of shaped catalyst bodies and shaped diluent bodies (both preferably having substantially the same geometry), in which the proportion by weight of the shaped diluent bodies (the densities of shaped catalyst bodies and of shaped diluent bodies generally differ only slightly) is normally from 5 to 40% by weight, or from 10 to 40% by weight, or from 20 to 40% by weight, or from 25 to 35% by weight. This first zone of the fixed catalyst bed is advantageously followed up to the end of the length of the fixed catalyst bed (i.e., for example, to a length of from 2.00 to 3.00 m, preferably from 2.50 to 3.00 m) either by a bed of shaped catalyst bodies diluted only to a slighter extent (than in the first zone), or, most preferably, an unaccompanied (undiluted) bed of the same shaped catalyst bodies which have also been used in the first zone. The aforesaid applies in particular when the shaped catalyst bodies used in the fixed catalyst bed are unsupported catalyst rings or coated catalyst rings (in particular those which are specified as preferred in this document). For the purposes of the above-mentioned structuring, both the shaped catalyst bodies and the shaped diluent bodies in the process according to the invention advantageously have substantially the ring geometry 5 mm×3 mm×2 mm (external diameter×length×internal diameter).

The aforesaid also applies when, instead of inert shaped diluent bodies, shaped coated catalyst bodies are used whose active composition content is from 2 to 15% by weight lower than the active composition content of any shaped coated catalyst bodies used at the end of fixed catalyst bed 1.

A pure inert material bed whose length, based on the length of fixed catalyst bed 1, is advantageously from 5 to 20% generally precedes fixed catalyst bed 1 in flow direction of reaction gas mixture 2. It is normally utilized as a heating zone for reaction gas mixture 2. Instead of the inert material bed, it is also possible to use catalyst bed diluted with inert material as a heating zone.

According to the invention, the fixed catalyst bed zone having the lower volume-specific activity in the aforementioned fixed catalyst beds 1 then advantageously extends into temperature zone B for from 5 to 20%, frequently from 5 to 15%, of its length.

Appropriately, temperature zone A also extends to a preliminary bed of inert material which is used if appropriate for fixed catalyst bed 1.

For the advantageousness of the procedure described, it is also essential that fixed catalyst bed 2 consists of at least two spatially successive fixed catalyst bed zones, and the volume-specific activity within one fixed catalyst bed zone is substantially constant and increases sharply in flow direction of reaction gas mixture 3 at the transition from one fixed catalyst bed zone to another fixed catalyst bed zone.

The volume-specific (i.e. normalized to the unit of the particular bed volume) activity of a fixed bed catalyst zone can then be adjusted over the fixed catalyst bed zone in a substantially constant manner by starting from a basic amount of shaped catalyst bodies prepared in a uniform manner (their bed corresponds to the maximum achievable volume-specific activity) and homogeneously diluting it in the particular fixed catalyst bed zone with shaped bodies (shaped diluent bodies) which behave substantially inertly with regard to the heterogeneously catalyzed partial gas phase oxidation. The higher the proportion of shaped diluent bodies selected, the less active composition, i.e. catalyst activity, is present in a certain volume of the bed. Useful materials for such inert shaped diluent bodies are in principle all of those which are suitable as support material for coated catalysts suitable according to the invention.

Useful such materials include, for example, porous or nonporous aluminum oxides, silicon dioxide, thorium dioxide, zirconium dioxide, silicon carbide, silicates such as magnesium silicate or aluminum silicate or the steatite already mentioned (e.g. Steatite C-220 from CeramTec).

The geometry of such inert shaped diluent bodies may in principle be as desired. In other words, they may, for example, be spheres, polygons, solid cylinders or else rings. According to the invention, the inert shaped diluent bodies selected will preferably be those whose geometry corresponds to that of the shaped catalyst bodies to be diluted with them.

According to the invention, it is favorable when the chemical composition of the active composition used does not vary over the entire fixed catalyst bed 2. In other words, although the active composition used for a single shaped catalyst body can be a mixture of different multimetal oxides comprising the elements Mo and V, the same mixture then has to be used for all shaped catalyst bodies of fixed catalyst bed 2.

A volume-specific activity increasing zone by zone over fixed catalyst bed 2 in flow direction of reaction gas mixture 3 can therefore be achieved for the process described in a simple manner, for example, by beginning the bed in a first fixed catalyst bed zone with a high proportion of inert shaped diluent bodies based on one type of shaped catalyst bodies, and then reducing this proportion of shaped diluent bodies zone by zone in flow direction.

However, a zone by zone increase in the volume-specific activity is also possible, for example, by increasing the thickness of the active composition layer applied to the support zone by zone at constant geometry and active composition type of a coated shaped catalyst body or, in a mixture of coated catalysts having the same geometry but having different proportions by weight of the active composition by increasing the proportion of shaped catalyst bodies having higher proportion by weight of active composition content zone by zone. Alternatively, the active compositions themselves can be diluted in the course of the active composition preparation by, for example, incorporating inert, diluting materials such as hard-fired silica into the dry mixture of starting compounds to be calcined. Different amounts of diluting material added lead automatically to different activities. The more diluting material is added, the lower the resulting activity will be. A similar effect can also be achieved, for example, in the case of mixtures of unsupported catalysts and of coated catalysts (having identical active composition) by varying the mixing ratio in an appropriate manner. A variation in the volume-specific activity can also be achieved by the use of catalyst geometries having different bed densities (for example, in the case of unsupported catalysts having identical active compositions of the different geometries). It is of course also possible to use the variants described in combination.

It is of course also possible to use mixtures of catalysts having chemically different active composition and, as a consequence of this different composition, having different activity for fixed catalyst bed 2. These mixtures may in turn, zone by zone, be varied in their composition and/or be diluted with different amounts of inert shaped diluent bodies.

Upstream and/or downstream of fixed catalyst bed 2 may be disposed beds consisting exclusively of inert material (for example only shaped diluent bodies) (in this document, they are not included for terminology purposes in fixed catalyst bed 2, since they do not comprise any shaped bodies which have multimetal oxide active composition). The shaped diluent bodies used for the inert bed may have the same geometry as the shaped catalyst bodies used in the fixed catalyst bed. However, the geometry of the shaped diluent bodies used for the inert bed may also be different to the abovementioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having a diameter d=4-5 mm. Temperature zones C and D in the process according to the invention may also extend to the inert beds. According to the invention, it is advantageous when neither temperature zone C nor temperature zone D covers more than three fixed catalyst bed zones (according to the invention, at least one fixed catalyst bed zone is necessarily covered by both temperature zones). According to the invention, it is particularly advantageous when the entire fixed catalyst bed 2 comprises not more than five, advantageously not more than four or three, fixed catalyst bed zones.

According to the invention, at the transition from one fixed catalyst bed zone to another fixed catalyst bed zone (in flow direction of reaction gas mixture 3), the volume-specific active composition (i.e. the weight of the multimetal oxide active composition present in a uniform bed volume) should (in the case of uniform active composition over the entire fixed catalyst bed 2) advantageously increase by at least 5% by weight, preferably by at least 10% by weight (this applies in particular in the case of uniform shaped catalyst bodies over the entire fixed catalyst bed 2). In general, this increase in the process according to the invention will not be more than 50% by weight, usually not more than 40% by weight. According to the invention, in the case of uniform active composition over the entire fixed catalyst bed 2, the difference in the volume-specific active composition of the fixed catalyst bed zone having the lowest volume-specific activity and the fixed catalyst bed zone having the highest volume-specific activity should also not be more than 50% by weight, preferably not more than 40% by weight, and generally not more than 30% by weight.

In the process according to the invention, fixed catalyst bed 2 will frequently consist of only two fixed catalyst bed zones.

According to the invention, preference is given to the last fixed catalyst bed zone of fixed catalyst bed 2 in flow direction of reaction gas mixture 3 being undiluted. In other words, it preferably consists exclusively of shaped catalyst bodies. If required, it may also consist of a bed of shaped catalyst bodies whose volume-specific activity is reduced, for example by dilution with inert material, for example by 10%. When fixed catalyst bed 2 consists of only two fixed catalyst bed zones, it is generally advantageous according to the invention (as is quite generally the case in the process according to the invention) when the fixed catalyst bed zone having the highest volume-specific activity projects into temperature zone C (in particular when the heating in temperature zone C and temperature zone D is effected by means of a flowing heat carrier which in each case flows in countercurrent to reaction gas mixture 3).

When fixed catalyst bed 2 consists of only three fixed catalyst bed zones, it is generally equally advantageous according to the invention when the fixed catalyst bed zone having the highest volume-specific activity projects into temperature zone C (in particular when the heating in temperature zone C and temperature zone D is effected by means of a flowing heat carrier which in each case flows in countercurrent to reaction gas mixture 3).

When fixed catalyst bed 2 consists of four fixed catalyst bed zones, it is generally advantageous in accordance with the invention when the fixed catalyst bed zone having the second highest volume-specific activity projects both into temperature zone C and into temperature zone D (in particular when the heating in temperature zone C and temperature zone D is effected by means of a flowing heat carrier which in each case flows in countercurrent to reaction gas mixture 3).

In the case of cocurrent flow of reaction gas mixture 3 and heat carriers in temperature zones C and D, it may be advantageous in accordance with the invention if the fixed catalyst bed zone within fixed catalyst bed 2 having the highest volume-specific activity does not project into temperature zone C, but rather only has its beginning beyond the transition from temperature zone C to temperature zone D.

The volume-specific activity between two fixed catalyst bed zones within fixed catalyst bed 2 can be differentiated experimentally in a simple manner by passing the same starting reaction gas mixture comprising acrolein over fixed catalyst beds of the same length but each corresponding to the composition of the particular fixed catalyst bed zone under identical boundary conditions (preferably the conditions of the contemplated process). The higher amount of acrolein converted indicates the higher volume-specific activity.

When the total length of fixed catalyst bed 2 is $L^2$, it is advantageous in accordance with the invention if there is no transition from one fixed catalyst bed zone to another fixed catalyst bed zone within the region of $$X^2 \pm L^2 \frac{4}{100}$$

or within the region of $$X^2 \pm L^2 \frac{3}{100}$$

or within the region of $$X^2 \pm L^2 \frac{2}{100},$$

where X is the location within fixed catalyst bed 2 of the transition from temperature zone C to temperature zone D.

Preference is given to fixed catalyst bed 2 in the above-described process being structured as follows in flow direction of reaction gas mixture 3.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of fixed catalyst bed 2, a homogeneous mixture or two (having decreasing dilution) successive homogeneous mixtures of shaped catalyst bodies and shaped diluent bodies (both preferably having substantially the same geometry), in which the proportion of shaped diluent bodies is such that the volume-specific active composition, based on a bed consisting only of shaped catalyst bodies, has been reduced by from 10 to 50% by weight, preferably from 20 to 45% by weight and more preferably from 25 to 35% by weight. According to the invention, this first or these first two zones are then advantageously followed to the end of the length of fixed catalyst bed 2 (i.e., for example, to a length of from 2.00 to 3.00 m, preferably from 2.50 to 3.00 m) by either a bed of the shaped catalyst bodies diluted only to a slighter extent (than in the first or in the first two zones) or, most preferably, an unaccompanied bed of the same shaped catalyst bodies which have also been used in the first zones.

The aforementioned applies in particular when the shaped catalyst bodies used in fixed catalyst bed 2 are coated catalyst rings or coated catalyst spheres (in particular those which are listed in this document as preferred). It is advantageous when, for the purposes of the aforementioned structuring, both the shaped catalyst bodies or their support rings and the shaped diluent bodies in the process according to the invention substantially have the ring geometry 7 mm×3 mm×4 mm (external diameter×length ×internal diameter).

The abovementioned also applies when, instead of inert shaped diluent bodies, shaped coated catalyst bodies are used whose active composition content is from 2 to 15% by weight lower than the active composition content of the shaped coated catalyst bodies at the end of the fixed catalyst bed.

A pure inert material bed whose length, based on the length of fixed catalyst bed 2, is advantageously from 5 to 20% generally precedes fixed catalyst bed 2 in flow direction of reaction gas mixture 3. It normally serves the purpose of heating reaction gas mixture 3. Instead of the inert material bed, it is also possible to use a catalyst bed diluted with inert material as a heating zone.

It is advantageous in accordance with the invention when temperature zone C (which also advantageously extends in accordance with the invention to the preliminary bed of inert material) in the aforementioned fixed catalyst beds 2 extends for from 5 to 20%, frequently from 5 to 15%, of its length to the last (volume-specifically most active) fixed catalyst bed zone of fixed catalyst bed 2 in flow direction of reaction gas mixture 3.

In an advantageous manner from an application point of view, the first reaction stage of the above-described process is carried out in a two-zone tube bundle reactor, as described, for example, in DE-A 199 10 508, 199 48 523, 199 10 506 and 199 48 241. A preferred variant of a two-zone tube bundle reactor which can be used in accordance with the invention is disclosed by DE-C 28 30 765. However, the two-zone tube bundle reactors disclosed in DE-C 25 13 405, U.S. Pat. No. 3,147,084, DE-A 22 01 528, EP-A 38 32 24 and DE-A 29 03 218 are also suitable for carrying out the first reaction stage of the above-described process.

In other words, in the simplest manner, the fixed catalyst bed 1 to be used (possibly with downstream and/or upstream inert beds) is disposed in the metal tubes of a tube bundle reactor and two substantially spatially separated heating media, generally salt melts, are conducted around the metal tubes. The tube section over which the particular salt bath extends represents a temperature zone in accordance with the invention. In other words, in the simplest manner, for example, a salt bath A flows around that section of the tubes (temperature zone A) in which the oxidative conversion of propene (in single pass) proceeds until a conversion in the range from 40 to 80 mol % is achieved, and a salt bath B flows around the section of the tubes (reaction zone B) in which the subsequent oxidative conversion of propene (in single pass) proceeds until a conversion value of at least 90 mol % is achieved (if required, the temperature zones A, B to be used in accordance with the invention may be followed by further reaction zones which are maintained at individual temperatures).

It is appropriate from an application point of view for the first reaction stage of the process described not to include any further temperature zones. In other words, salt bath B appropriately flows around the section of the tubes in which the subsequent oxidative conversion of propene (in single pass) proceeds up a conversion value of $\geqq$90 mol %, or $\geqq$92 mol % or $\geqq$94 mol % or more.

Typically, the beginning of temperature zone B lies beyond the hotspot maximum of temperature zone A.

According to the invention, both salt baths A, B can be conducted in cocurrent or in countercurrent through the space surrounding the reaction tubes relative to the flow direction of the reaction gas mixture flowing through the reaction tubes. It is of course also possible in accordance with the invention to employ cocurrent flow in temperature zone A and countercurrent flow in temperature zone B (or vice versa).

In all of the aforementioned cases, it is of course possible to superimpose a transverse flow on the parallel flow of the salt melt, relative to the reaction tubes, taking place within the particular temperature zone, so that the individual reaction zone corresponds to a tube bundle reactor as described in EP-A 700 714 or in EP-A 700 893, which results overall in a meandering flow profile of the heat exchange medium in a longitudinal section through the catalyst tube bundle.

Appropriately, starting reaction gas mixture 2 in the process according to the invention is fed preheated to the reaction temperature to fixed catalyst bed 1.

Typically, the catalyst tubes in the two-zone tube bundle reactors are manufactured from ferritic steel and typically have a wall thickness of from 1 to 3 mm. Their internal diameter is generally from 20 to 30 mm, frequently from 21 to 26 mm. Their length is advantageously from 2 to 4 m, preferably from 2.5 to 3.5 m. In each temperature zone, the fixed bed catalyst charge 1 occupies at least 60%, or at least 75%, or at least 90%, of the length of the zone. Any remaining length is optionally occupied by an inert bed. It is advantageous from an application point of view for the number of catalyst tubes accommodated in the tube bundle vessel to be at least 5000, preferably at least 10 000. Frequently, the number of catalyst tubes accommodated in the reaction vessel is from 15 000 to 30 000. Tube bundle reactors having a number of catalyst tubes above 40 000 are usually exceptional. Within the vessel, the catalyst tubes are normally homogeneously distributed (preferably 6 equidistant adjacent tubes per catalyst tube), and the distribution is advantageously selected in such a way that the separation of the central internal axes of immediately adjacent catalyst tubes (known as the catalyst tube pitch) is from 35 to 45 mm (cf., for example, EP-B 468 290).

Suitable heat exchange media for the two-zone method are also in particular fluid heating media. It is particularly favorable to use melts of salts such as potassium nitrate, potassium nitrite, sodium nitrite and/or sodium nitrate, or of low-melting metals such as sodium, mercury and also alloys of different metals.

In general, in all of the aforementioned flow arrangements in the two-zone tube bundle reactors, the flow rate within the two heat exchange medium circuits required is selected in such a way that the temperature of the heat exchange medium rises from the entrance into the temperature zone to the exit from the temperature zone (as a result of the exothermicity of the reaction) by from 0 to 15° C. In other words, the aforementioned $\Delta T$ may, in accordance with the invention, be from 1 to 10° C., or from 2 to 8° C., or from 3 to 6° C.

According to the invention, the entrance temperature of the heat exchange medium into temperature zone A is normally in the range from 290 to 380° C., preferably in the range from 305 to 365° C. and more preferably in the range from 310 to 340° C. or is 330° C. According to the invention, in the case of propene hourly space velocities on fixed catalyst bed 1 of $\geq 90$ l (STP)/l·h and $\leq 160$ l (STP)/l·h, the entrance temperature of the heat exchange medium into temperature zone B is likewise in the range from 290 to 380° C., but at the same time normally, appropriately in accordance with the invention, from $\geq 0°$ C. to $\leq 20°$ C., or $\leq 10°$ C., or $\geq 0°$ C. and $\leq 5°$ C., or frequently $\geq 0°$ C. and $\leq 3°$ C., below the entrance temperature of the heat exchange medium entering temperature zone A. According to the invention, in the case of propene hourly space velocities on fixed catalyst bed 1 of $\geq 160$ l (STP)/l·h and (generally) $\leq 300$ l (STP)/l·h (or 600 l (STP)/l·h), the entrance temperature of the heat exchange medium into temperature zone B will likewise be in the range from 290 to 380° C., but normally, appropriately in accordance with the invention, from $\geq 0°$ C. to $\leq 50°$ C., or $\geq 5°$ C. and $\leq 45°$ C., or $\geq 10°$ C. and $\leq 40°$ C., or $\geq 15°$ C. and $\leq 30°$ C. or $\leq 35°$ C. (for example 20° C. or 25° C.), above the entrance temperature of the heat exchange medium entering temperature zone A.

It should be pointed out once again here that, for an implementation of reaction stage 1 of the process according to the invention, it is also possible in particular to use the two-zone tube bundle reactor type which is described in DE-B 22 01 528 and includes the possibility of removing a portion of the hotter heat exchange medium of temperature zone B to temperature zone A, in order if appropriate to heat a cold starting reaction gas mixture or a cold cycle gas. The tube bundle characteristics within an individual temperature zone may also be configured as described in EP-A 382 098.

Otherwise, it has been found to be appropriate to cool the product gas mixture leaving the first reaction stage in a direct and/or indirect manner before it enters the second reaction stage, in order thus to suppress subsequent complete combustion of portions of the acrolein formed in the first reaction stage. To this end, an aftercooler is typically connected between the two reaction stages. In the simplest case, this may be an indirect tube bundle heat transferrer. In this case, the product gas mixture is generally conducted through the tubes and a heat exchange medium is conducted around the tubes and may be of the type corresponding to the heat exchange media recommended for the tube bundle reactors. Advantageously, the tube interior is filled with inert random packings (for example spirals of stainless steel, rings of steatite, spheres of steatite, etc.). These improve the heat exchange and capture any molybdenum trioxide subliming from the fixed catalyst bed of the first reaction stage before it enters the second reaction stage. It is advantageous for the aftercooler to be manufactured from stainless steel coated with zinc silicate primer.

In general, the propene conversion based on single pass in the process according to the invention in the first reaction stage will be $\geq 92$ mol % or $\geq 94$ mol %. According to the invention, the resulting selectivity of acrolein formation and also of acrylic acid by-product formation together in single pass in the first reaction stage will regularly be $\geq 92$ mol % or $\geq 94$ mol %, frequently $\geq 95$ mol % or $\geq 96$ mol % or $\geq 97$ mol %.

It is appropriate from an application point of view to cool the product gas mixture of the first reaction stage in the aftercooler already mentioned to a temperature of from 210 to 290° C., frequently from 230 to 280° C. or from 250 to 270° C. The product gas mixture of the first reaction stage can quite possibly be cooled to temperatures which are below the temperature of the second reaction stage. However, the aftercooling described is no way obligatory and can generally be dispensed with, especially when the path of the product gas mixture from the first reaction stage to the second reaction stage is kept short. Advantageously, the two-stage partial oxidation process described is also realized in such a way that the oxygen requirement in the second reaction stage is not already covered by an appropriately high oxygen content of starting reaction gas mixture 2, but rather that the required oxygen is added in the region between the first and second reaction stages ("secondary oxygen addition"). This may be effected before, during, after and/or for aftercooling. Useful sources for the molecular oxygen required in the second reaction stage include both pure oxygen and mixtures of oxygen and inert gas, for example air (preferred in accordance with the invention) or air depleted in molecular nitrogen (for example, $\geq 90$% by volume of $O_2$, $\leq 10$% by volume of $N_2$). The oxygen source is regularly added compressed to the reaction pressure. The oxygen requirement in the second reaction stage of the process according to the invention can of course already be covered by an appropriately high oxygen requirement in the first reaction stage. If required, an inert diluent gas can of course also be added as a secondary gas.

Like the performance of the first reaction stage, the second reaction stage of the process according to the invention is also performed in an appropriate manner from an application point of view in a two-zone tube bundle reactor, as has already been described for the first reaction stage. The remarks regarding the two-zone tube bundle reactor for the first reaction stage therefore also apply to the two-zone tube bundle reactor for the second reaction stage.

In other words, in a simple manner, the fixed catalyst bed 2 (including any inert beds) to be used in accordance with the invention is disposed in the metal tubes of a tube bundle reactor and two substantially spatially separated heating media, generally salt melts, are conducted around the metal tubes. According to the invention, the tube section over which the respective salt bath extends represents a temperature zone.

In other words, in a simple manner, for example, a salt bath C flows around those sections of the tubes (temperature zone C) in which the oxidative conversion of acrolein (in single pass) proceeds until a conversion value in the range from 45 to 85 mol % (preferably from 50 to 85 mol %, more preferably from 60 to 85 mol %) is achieved, and a salt bath D flows around the section of the tubes (temperature zone D) in which the subsequent oxidative conversion of acrolein (in single pass) proceeds until a conversion value of 90 mol % is achieved (if required, the temperature zones C, D to be used in accordance with the invention may be followed by further temperature zones which are maintained at individual temperatures).

It is appropriate from an application point of view for reaction stage 2 of the process according to the invention not to include any further temperature zones. In other words, salt bath D advantageously flows around the section of the tubes in which the subsequent oxidative conversion of acrolein (in single pass) proceeds up to a conversion value of $\geq 92$ mol %, or $\geq 94$ mol % or $\geq 96$ mol % or $\geq 98$ mol % and frequently even $\geq 99$ mol % or more.

Typically, the beginning of temperature zone D lies beyond the hotspot maximum of temperature zone C.

According to the invention, both salt baths C, D can be conducted in cocurrent or in countercurrent through the space surrounding the reaction tubes relative to the flow direction of the reaction gas mixture flowing through the reaction tubes. It is of course also possible in accordance with the invention to employ cocurrent flow in temperature zone C and countercurrent flow in temperature zone D (or vice versa).

In all of the aforementioned cases, it is of course possible to superimpose a transverse flow on the parallel flow of the salt melt, relative to the reaction tubes, taking place within the particular temperature zone, so that the individual reaction zone corresponds to a tube bundle reactor as described in EP-A 700 714 or in EP-A 700 893, which results overall in a meandering flow profile of the heat exchange medium in a longitudinal section through the catalyst tube bundle.

Typically, the catalyst tubes in the aforementioned two-zone tube bundle reactors for the second reaction stage are manufactured from ferritic steel and typically have a wall thickness of from 1 to 3 mm. Their internal diameter is generally from 20 to 30 mm, frequently from 21 to 26 mm. Their length is advantageously from 3 to 4 m, preferably 3.5 m. In each temperature zone, fixed catalyst bed 2 occupies at least 60%, or at least 75%, or at least 90%, of the length of the zone. Any remaining length is optionally occupied by an inert bed. It is advantageous from an application point of view for the number of catalyst tubes accommodated in the tube bundle vessel to be at least 5000, preferably at least 10 000. Frequently, the number of catalyst tubes accommodated in the reaction vessel is from 15 000 to 30 000. Tube bundle reactors having a number of catalyst tubes above 40 000 are usually exceptional. Within the vessel, the catalyst tubes are normally homogeneously distributed (preferably 6 equidistant adjacent tubes per catalyst tube), and the distribution is advantageously selected in such a way that the separation of the central internal axes of immediately adjacent catalyst tubes (known as the catalyst tube pitch) is from 35 to 45 mm (cf. EP-B 468 290).

Suitable heat exchange media are in particular fluid heating media. It is particularly favorable to use melts of salts such as potassium nitrate, potassium nitrite, sodium nitrite and/or sodium nitrate, or of low-melting metals such as sodium, mercury and also alloys of different metals.

In general, in all of the abovementioned flow arrangements in the two-zone tube bundle reactors of the second reaction stage, the flow rate within the two heat exchange medium circuits required is selected in such a way that the temperature of the heat exchange medium rises from the entrance into the temperature zone to the exit from the temperature zone by from 0 to 15° C. In other words, the aforementioned $\Delta T$ may, in accordance with the invention, be from 1 to 10° C., or from 2 to 8° C., or from 3 to 6° C.

According to the invention, the entrance temperature of the heat exchange medium into temperature zone C is normally in the range from 230 to 320° C., preferably in the range from 250 to 300° C. and more preferably in the range from 260 to 280° C. According to the invention, in the case of acrolein hourly space velocities on fixed catalyst bed 2 of $\geq 70$ l (STP)/l·h and $\leq 150$ l (STP)/l·h, the entrance temperature of the heat exchange medium into temperature zone D is likewise in the range from 230 to 320° C., but at the same time normally, advantageously in accordance with the invention, from $\geq 0$° C. to $\leq 20$° C. or $\leq 10$° C., or $\geq 0$° C. and $\leq 5$° C., or frequently $\geq 0$° C. and $\leq 3$° C., below the entrance temperature of the heat exchange medium entering temperature zone C. According to the invention, in the case of acrolein hourly space velocities on the fixed catalyst bed of $\geq 150$ l (STP)/l·h and (generally) $\leq 300$ l (STP)/l·h (or 600 l (STP)/l·h), the entrance temperature of the heat exchange medium into temperature zone D will likewise be in the range from 230 to 320° C., but at the same time normally, advantageously in accordance with the invention, from $\geq 0$° C. to $\leq 40$° C., or $\geq 5$° C. and $\leq 35$° C., or 30° C., or $\geq 10$° C. and $\leq 25$° C., or 20° C., or 15° C., above the entrance temperature of the heat exchange medium entering temperature zone C.

It should be pointed out once again here that, for a performance of the second reaction stage of the process described, it is also possible in particular to use the two-zone tube bundle reactor type which is described in DE-B 22 01 528 and includes the possibility of removing a portion of the hotter heat exchange medium of temperature zone D to temperature zone C, in order if appropriate to heat a starting reaction gas mixture 3 which is too cold. The tube bundle characteristics within an individual reaction zone may also be configured as described in EP-A 382 098.

It is of course also possible to carry out the process described by combining two two-zone tube bundle reactors to give a four-zone tube bundle reactor, as described in WO 01/36364. In these cases, there is normally an inert bed between fixed catalyst bed 1 and fixed catalyst bed 2. However, such an intermediate inert bed may also be dispensed with. The length of the reaction tubes in the event of combination corresponds in many cases to the sum of the lengths of the uncombined tube bundle reactors.

It should be emphasized here that the multimetal oxide compositions of DE-A 102 61 186 are also favorable as active compositions both for fixed catalyst bed 1 and for fixed catalyst bed 2.

Favorable designs of a two-zone tube bundle reactor for the first reaction stage may have the following construction (the detailed configuration of the construction can be as described in the utility model applications 202 19 277.6, 2002 19 278.4 and 202 19 279.2 or in the PCT applications PCT/EP02/14187, PCT/EP02/14188 or PCT/EP02/14189):

| Catalyst tubes: | |
| --- | --- |
| material of the catalyst tubes: | ferritic steel; |
| dimensions of the catalyst tubes: | length, for example, 3500 mm; |
| | external diameter, for example, 30 mm; |
| | wall thickness, for example, 2 mm; | number of catalyst tubes in the tube bundle: for example, 30 000, or 28 000, or 32 000, or 34 000; in addition up to 10 thermal tubes (as described in EP-A 873 783 and EP-A 12 70 065) which are charged in the same way as the catalyst tubes (in a spiral manner rotating from the very outside inward), for example of the same length and wall thickness but having an external diameter of, for example, 33.4 mm and a centered thermowell of external diameter, for example, 10 mm and wall thickness of, for example, 1 mm;

reactor (same material as the catalyst tubes):

cylindrical vessel of internal diameter 6000-8000 mm;

reactor hoods plated with type 1.4541 stainless steel; plating thickness: a few mm;

annularly arranged tube bundle, for example with a free central space:

diameter of the free central space: for example, 1000-2500 mm (for example 1200 mm, or 1400 mm, or 1600 mm, or 1800 mm, or 2000 mm, or 2200 mm, or 2400 mm);

normally homogeneous catalyst tube pitch in the tube bundle (6 equidistant adjacent tubes per catalyst tube), arrangement in an equilateral triangle, catalyst tube pitch (separation of the central internal axes of immediately adjacent catalyst tubes): 35-45 mm, for example 36 mm, or 38 mm, or 40 mm, or 42 mm, or 44 mm;

the catalyst tubes are secured and sealed by their ends in catalyst tube plates (upper plate and lower plate each having a thickness, for example, of 100-200 mm) and open at their upper ends into a hood joined to the vessel which has an inlet for starting reaction gas mixture 2; a separating plate of thickness 20-100 mm disposed, for example, at half the catalyst tube length, divides the reactor space symmetrically into two temperature zones A (upper zone) and B (lower zone); each temperature zone is divided into 2 equidistant longitudinal sections by a deflecting plate;

the deflecting plate preferably has annular geometry; the catalyst tubes are advantageously secured and sealed at the separating plate; they are not secured and sealed at the deflecting plates, so that the transverse flow rate of the salt melt within one zone is substantially constant;

each zone is provided with salt melt as a heat carrier by a dedicated salt pump; the feed of the salt melt is, for example, below the deflecting plate and the withdrawal is, for example, above the deflecting plate;

a substream is, for example, removed from both salt melt circuits and cooled, for example, in one common or two separate indirect heat exchangers (steam-raising);

in the first case, the cooled salt melt stream is divided, combined with the particular residual stream and pressurized into the reactor by the particular pump into the appropriate annular channel which divides the salt melt over the circumference of the vessel;

the salt melt reaches the tube bundle through the window disposed in the reactor jacket; the flow is, for example, in a radial direction to the tube bundle;

in each zone, the salt melt flows around the catalyst tubes as dictated by the deflection plate, for example in the sequence from the outside inward, from the inside outward, through windows mounted around the circumference of the vessel, the salt melt collects at the end of each zone in an annular channel disposed around the reactor jacket, in order to be pumped in a circuit including substream cooling;

the salt melt is conducted from bottom to top through each temperature zone.

The reaction gas mixture leaves the reactor of the first stage at a temperature a few degrees higher than the salt bath entrance temperature of the reactor. For further processing, the reaction gas mixture is advantageously cooled to from 220° C. to 280° C., preferably from 240° C. to 260° C., in a separate aftercooler which is connected downstream of the reactor of the 1st stage.

The aftercooler is generally flanged on below the lower tube plate and normally consists of tubes of ferritic steel. Stainless steel sheet metal spirals which may be partly or fully wound are advantageously introduced into the interior of the tubes of the aftercooler, in order to improve the heat transfer.

Salt Melt:

The salt melt used may be a mixture of 53% by weight of potassium nitrate, 40% by weight of sodium nitrite and 7% by weight of sodium nitrate; both reaction zones and the aftercooler advantageously employ a salt melt of the same composition; the amount of salt pumped by circulation in the reaction zones may be approx. 10 000 m³/h per zone.

Flow Control:

The starting reaction gas mixture 2 advantageously flows from top to bottom through the first stage reactor, while the salt melts having different temperatures of the individual zones are advantageously conveyed from bottom to top;

Catalyst tube and thermal tube charge (from top to bottom), for example:

Section 1: length 50 cm
steatite rings of geometry 7 mm × 7 mm × 4 mm (external diameter × length × internal diameter) as a preliminary bed.
Section 2: length 140 cm
catalyst charge of a homogeneous mixture of 30% by weight of steatite rings of geometry 5 mm × 3 mm × 2 mm (external diameter × length × internal diameter) and 70% by weight of unsupported catalyst from section 3.
Section 3: length 160 cm
catalyst charge of annular (5 mm × 3 mm × 2 mm = external diameter × length × internal diameter) unsupported catalyst according to example 1 of DE-A 10046957 (stoichiometry: $[Bi_2W_2O_9 \cdot 3WO_3]_{0.5} [Mo_{12}Co_{5.5}Fe_{2.94}Si_{1.59}K_{0.08}O_x]_1$).

Favorable configurations of a two-zone tube bundle reactor for the second reaction stage can be designed as follows:

Everything as in the two-zone tube bundle reactor for the first reaction stage. However, the thickness of the upper and lower catalyst tube plates is frequently 100-200 mm, for example 110 mm, or 130 mm, or 150 mm, or 170 mm, or 190 mm.

The aftercooler is dispensed with; instead, the lower openings of the catalyst tubes open into a hood which is connected to the vessel at the lower end and has an outlet for the product gas mixture; the upper temperature zone is zone C and the lower temperature zone is temperature zone D. Between the "aftercooler" outlet and the "reactor for the second reaction stage" inlet there is advantageously a means for feeding compressed air.

The catalyst tube and thermal tube charge (from top to bottom) may, for example, be as follows:

Section 1: length 20 cm
steatite rings of geometry 7 mm × 7 mm × 4 mm (external diameter × length × internal diameter) as a preliminary bed.
Section 2: length 90 cm
catalyst charge of a homogeneous mixture of 30% by weight of steatite rings of geometry 7 mm × 3 mm × 4 mm (external diameter × length × internal diameter) and 70% by weight of coated catalyst from section 4.
Section 3: length 50 cm
catalyst charge of a homogeneous mixture of 20% by weight -continued Section 4: length 190 cm
catalyst charge of annular (7 mm × 3 mm × 4 mm = external diameter × length × internal diameter) coated catalyst according to preparative example 5 of DE-A 100 46 928 (stoichiometry: $Mo_{12}V_3W_{1.2}Cu_{2.4}O_x$).

of steatite rings of geometry 7 mm × 3 mm × 4 mm (external diameter × length × internal diameter) and 80% by weight of coated catalyst from section 4.

The second stage catalyst tube and thermal tube charge may also have the following appearance (from top to bottom):

Section 1: length 20 cm
steatite rings of geometry 7 mm × 7 mm × 4 mm (external diameter × length × internal diameter) as a preliminary bed.
Section 2: length 140 cm
catalyst charge of a homogeneous mixture of 25% by weight of steatite rings of geometry 7 mm × 3 mm × 4 mm (external diameter × length × internal diameter) and 75% by weight of coated catalyst from section 3.
Section 3: length 190 cm
catalyst charge of annular (7 mm × 3 mm × 4 mm = external diameter × length × internal diameter) coated catalyst according to preparative example 5 of DE-A 100 46 928 (stoichiometry: $Mo_{12}V_3W_{1.2}Cu_{2.4}O_x$).

In the first stage charge mentioned, the unsupported catalyst from example 1 of DE-A 100 46 957 may also be replaced by:
a) a catalyst according to example 1 c of EP-A 15 565 or a catalyst to be prepared in accordance with this example, except having the active composition $Mo_{12}Ni_{6.5}Zn_2Fe_2Bi_1P_{0.0065}K_{0.06}O_x \cdot 10\ SiO_2$;
b) example no. 3 of DE-A 198 55 913 as an unsupported hollow cylinder catalyst of geometry 5 mm×3 mm×2 mm or 5 mm×2 mm×2 mm;
c) unsupported multimetal oxide II catalyst according to example 1 of DE-A 197 46 210;
d) one of the coated catalysts 1, 2 and 3 of DE-A 100 63 162, except applied in the same coating thickness to support rings of geometry 5 mm×3 mm×1.5 mm or 7 mm×3 mm×1.5 mm;
e) the catalysts, especially the working examples, of DE-A 10344149 and DE-A 10353954.

In all of the abovementioned second stage charges, the coated catalyst may be replaced in accordance with preparative example 5 of DE-A 100 46 928 by:
a) coated catalyst S1 or S7 from DE-A 4442346 having an active composition content of 27% by weight and a coating thickness of 230 μm;
b) a coated catalyst according to examples 1 to 5 of DE 198 15 281, except applied to support rings of geometry 7 mm×3 mm×4 mm having an active composition content of 20% by weight;
c) coated catalyst having biphasic active composition of stoichiometry $(Mo_{10.4}V_3W_{1.2}O_x)\ (CuMo_{0.5}W_{0.5}O_4)_{1.6}$, prepared according to DE-A 197 36 105 and having an active composition content of 20% by weight, applied to the aforementioned 7 mm×3 mm×4 mm support.

According to the invention, fixed catalyst bed 1 and fixed catalyst bed 2 are appropriately otherwise selected in such a way (for example by dilution with, for example, inert material) that the temperature difference between the hotspot maximum of the reaction gas mixture in the individual reaction zones and the particular temperature of the reaction zone generally does not exceed 80° C. This temperature difference is usually ≦70° C., frequently from 20 to 70° C.; this temperature difference is preferably small. For safety reasons, fixed catalyst beds 1 and 2 are also selected in a manner known per se to those skilled in the art (for example by dilution with, for example, inert material) in such a way that the peak-to-salt-temperature sensitivity as defined in EP-A 1106598 is ≦9° C., or ≦7° C., or ≦5° C., or ≦3° C.

Aftercooler and reactor for the second stage are connected by a connecting tube whose length is less than 25 m.

In the examples with a two-zone design contained in this document and in the reactor arrangement above, the annular shaped diluent bodies and the annular shaped catalyst bodies in the second reaction stage may also be replaced by spherical shaped diluent bodies and spherical shaped catalyst bodies (each having a radius from 2 to 5 mm and having an active composition content of from 10 to 30% by weight, frequently from 10 to 20% by weight).

The product gas mixture (referred to here as product gas mixture 2 (after the first reaction stage) or 3 (after the second reaction stage)) which leaves the inventive partial oxidation (after the first and/or the second reaction stage) is, in the case of a preparation of acrolein and/or acrylic acid, composed substantially of the target product acrolein or acrylic acid or a mixture thereof with acrolein, unconverted molecular oxygen (with a view to the lifetime of the catalysts used, it is favorable when the oxygen content both in product gas mixture 2 and in product gas mixture 3 is still from at least 1.5 to 4% by volume), propane, unconverted propylene, molecular nitrogen, steam which has formed as a by-product and/or has been used as a diluent gas, carbon oxides which have been used as a diluent gas or result as a by-product, and small amounts of other lower aldehydes, lower alkanecarboxylic acids (e.g. acetic acid, formic acid and propionic acid) and maleic anhydride, benzaldehyde, aromatic carboxylic acids and aromatic carboxylic anhydrides (e.g. phthalic anhydride and benzoic acid), in some cases further hydrocarbons, for example C4 hydrocarbons (e.g. butene-1 and possible other butenes), and other inert diluent gases.

The target product may be removed from product gas mixture 3 or 2 in a manner known per se in a separating zone (for example by partial or full and, if appropriate, fractional condensation of acrylic acid, or by absorption of acrylic acid in water or in a high-boiling hydrophobic organic solvent, or by absorption of acrolein in water or in aqueous solutions of lower carboxylic acids and subsequent workup of the condensates and/or absorbates; according to the invention, product gas mixture 3 or 2 will preferably be fractionally condensed; cf., for example, EP-A 13 88 533, EP-A 13 88 532, DE-A 102 35 847, EP-A 79 28 67, WO 98/01415, EP-A 10 15 411, EP-A 10 15 410, WO 99/50219, WO 00/53560, WO 02/09839, DE-A 102 35 847, WO 03/041833, DE-A 102 23 058, DE-A 102 43 625, DE-A 103 36 386, EP-A 85 41 29, U.S. Pat. No. 4,317,926, DE-A 198 37 520, DE-A 196 06 877, DE-A 190 50 1325, DE-A 102 47 240, DE-A 197 40 253, EP-A 69 57 36, EP-A 98 22 87, EP-A 10 41 062, EP-A 11 71 46, DE-A 43 08 087, DE-A 43 35 172, DE-A 44 36 243, DE-A 19 924 532, DE-A 103 32 758 and DE-A 19 924 533). An acrylic acid removal may also be undertaken as in EP-A 98 22 87, EP-A 98 22 89, DE-A 103 36 386, DE-A 101 15 277, DE-A 196 06 877, DE-A 197 40 252, DE-A 196 27 847, EP-A 92 04 08, EP-A 10 68 174, EP-A 10 66 239, EP-A 10 66 240, WO 00/53560, WO 00/53561, DE-A 100 53 086 and EP-A 98 22 88. Preference is given to removing as described in FIG. 7 of WO/0196271 or as described in DE-A 10 2004 032 129 and its equivalent patents. Favorable removal methods are also the processes described in the documents WO 2004/063138, WO 2004/035514, DE-A 102 43 625 and DE-A 102 35 847. Crude acrylic acid obtained in this way may be further processed, for example, as described in the documents WO 01/77056, WO 03/041832, WO 02/055469, WO 03/078378 and WO 03/041833.

A common feature of the above separating processes is (as already mentioned at the outset) that a residual gas stream which comprises substantially those constituents of product gas mixture 2 or 3 whose boiling point at standard pressure (1 bar) is $\leq -30°$ C. (i.e. the constituents which are difficult to condense or else volatile) normally remains at the top of the particular separating column which comprises separating internals and in whose lower section product gas mixture 3 or 2 is fed, normally after preceding direct and/or indirect cooling thereof.

In the lower section of the separating column, the less volatile constituents of product gas mixture 3 or 2, including the particular target product, are normally obtained in the condensed phase.

The residual gas constituents are primarily propane, any propylene which has not been converted in the partial oxidation, molecular oxygen and other inert diluent gases which are frequently also used in the partial oxidation, for example nitrogen and carbon dioxide. Depending on the separation process employed, steam may be present in the residual gas only in traces or in amounts of up to 20% by volume or more.

According to the invention, at least a portion (preferably the entire amount, if appropriate however only half, or two thirds, or three quarters, of this entire amount), (preferably having residual gas composition) comprising propane, molecular oxygen and any unconverted propylene, of this main gas residue is recycled as a comprising feed stream propane into the heterogeneously catalyzed propane dehydrogenation and/or propane oxydehydrogenation which, if appropriate, serves as a propene source (oxidation cycle gas). However, portions of residual gas may also be recycled into one or into both stages of the partial oxidation and/or be incinerated for the purpose of energy generation.

In the workup of the condensed phase (for the purpose of removing the target product), further residual gases may occur, since it will normally be attempted to recycle the total amount of unconverted propane and propylene present in product gas mixture 3 or 2 into the heterogeneously catalyzed propane dehydrogenation and/or propane oxydehydrogenation which, if appropriate, serves as a propylene source, and to recover them in the target removal. Although they generally still comprise propane and in some cases propylene, they frequently no longer comprise any molecular oxygen. Typically, they are recycled, combined with the main residual gas to give an overall residual gas, into the heterogeneously catalyzed propane dehydrogenation and/or propane oxydehydrogenation which, if appropriate, serves as a propylene source. However, it is also possible to separately utilize such further residual gases.

The preferably full recycling of the remaining overall residual gas thus allows continuous conversion of propane to acrylic acid and/or acrolein in continuous operation.

In this context, it is essential that the recycling described into the heterogeneously catalyzed propane dehydrogenation and/or propane oxydehydrogenation which, if appropriate, serves as a propylene source makes it possible to achieve therein a conversion over the entire process of propane to propylene with virtually one hundred percent selectivity.

The advantageousness of such a procedure exists both at lower ($\leq 30$ mol %) and at high ($\geq 30$ mol %) dehydrogenation conversions (based on single pass of fresh propane through the dehydrogenation). Generally, it is favorable in the case of such recycling of oxidation cycle gas when the hydrogen content in starting reaction gas mixture 1 is in an at least stoichiometric ratio (based on oxygen combustion to water) to the amount of oxygen recycled into starting reaction gas mixture 1 via oxidation cycle gas.

The aforementioned cycle gas method can be employed correspondingly when the partial oxidation is a partial ammoxidation of propene to acrylonitrile. It can even be employed correspondingly when propane is replaced by isobutane in the dehydrogenation and the resulting isobutene is partially oxidized in a corresponding manner in a partial oxidation to methacrolein and/or methacrylic acid.

It should also be emphasized once again here that acrylic acid is removed from a product gas mixture 3 obtained in accordance with the invention (in particular from one listed by way of example) preferably in such a way that the product gas mixture 3 which has been cooled beforehand if appropriate by direct and/or indirect cooling is fractionally condensed, ascending (for example into itself), in a column comprising separating internals with side draw removal of crude acrylic acid, and/or absorbed by means of water and/or aqueous solution, as described by way of example in WO 2004/035514 and DE-A 10243625. The crude acrylic acid withdrawn is subsequently preferably subjected to a suspension crystallization and the acrylic acid suspension crystals which are formed are preferably removed from remaining mother liquor by means of a wash column. Advantageously, the wash liquid used is the melt of acrylic acid crystals which have been removed beforehand in the wash column. Furthermore, the wash column is preferably one having forced transport of the crystal bed. It is more preferably a hydraulic or a mechanical wash column. For specific details, the description of WO 01/77056, WO 03/041832 and WO 03/041833 may be followed. In other words, preference is given to recycling mother liquor which remains into the fractional condensation (cf. also EP-A 10 15 410). The secondary component discharge is normally below the side draw of the crude acrylic acid as a purge stream.

Using only one crystallization stage, it is thus possible to obtain acrylic acid having a purity of $\geq 99.8\%$ by weight which is outstandingly suitable for producing superabsorbents based on poly-Na acrylate. It should also be emphasized that one advantage of the inventive procedure is in principle that, at all points in this document, including the working examples which follow, wherever catalyst charges diluted with inert material are described and/or required, the corresponding catalysts can also be used undiluted for the same bed length.

EXAMPLES

I. Heterogeneously Catalyzed Partial Propane Dehydrogenations as a Propylene Source General experimental construction and experimental design and results (the steady operating state is described in all cases)

The heterogeneously catalyzed partial propane dehydrogenations were carried out in a tray loop reactor according to FIG. 1, to which the numerical addresses below relate.

A vertical tubular reactor (11) (diameter: 80 mm) was encased in a support heater (9) provided with thermal insulation (10). The temperature of the support heater was 500° C. In the center of the tubular reactor was disposed a central tube (diameter: 20 mm) which contained a sleeve for a continuous thermoelement and a sleeve for a staged thermoelement. In addition, it contained lines leading into the tubular reactor, through which reaction gas samples could be withdrawn from the tubular reactor, and lines leading into the tubular reactor, through which air could be injected into the tubular reactor.

The tubular reactor contained three trays (5, 6, 7) which consisted of three identical beds of inert material and dehydrogenation catalyst placed on a stainless steel wire mesh. In flow direction of the reaction gas through the dehydrogenation reactor, the beds were constructed as follows:

First, to a bed length of 60 mm, a bed of steatite spheres (diameter: 4 to 5 mm) of Steatite C-220 from CeramTec. Then, to a bed length of 120 mm, dehydrogenation catalysts (Pt/Sn alloy which had been promoted with the elements Cs, K and La in oxidic form and which had been applied to the outer and inner surface of $ZrO_2 \cdot SiO_2$ mixed oxide support extrudates (average length (Gaussian distribution in the range from 3 mm to 12 mm with maximum at approx. 6 mm): 6 mm, diameter: 2 mm) in the elemental stoichiometry (mass ratios including support) $Pt_{0.3}Sn_{0.6}La_{3.0}Cs_{0.5}K_{0.2}(ZrO_2)_{88.3}(SiO_2)_{7.1}$ (catalyst precursor preparation and activation to the active catalyst as in example 4 of DE-A 10219879).

The product gas mixture 1 leaving the last tray was divided into two halves of identical composition. One half (2) was recycled into the dehydrogenation as a constituent of the starting reaction gas mixture (4). The other half (1) was conducted out of the dehydrogenation zone.

Absorption in technical-grade tetradecane from Haltermann, Germany of the PKWF 4/7 af type as an absorbent and subsequent stripping with air allows (as described in DE-A 10 2004 032 129) the constituents other than propylene and propane to be substantially removed and a charge gas mixture suitable directly for the partial oxidation of propylene to acrolein and/or acrylic acid to be obtained. The starting reaction gas mixture (4) consisted of dehydrogenation cycle gas (2) and steam, oxidation cycle gas (simulated for simplification by a mixture of oxygen and nitrogen) and fresh propane (all three symbolized here together by the address (3)).

The fresh propane had the following contents:

|  | % by vol. |
|---|---|
| methane | 0.005 |
| ethane | 0.005 |
| ethene | 0 |
| propane | 99.982 |
| propene (propylene) | 0.003 |
| isobutane | 0.005 |

The hourly space velocity on the first catalyst bed of propane was in all cases 305 l (STP)/l·h.

The entrance pressure of the starting reaction gas mixture was 2.3 bar. The pressure drop over the dehydrogenation reactor was approx. 200 mbar. Upstream of the second and upstream of the third catalyst charge (in flow direction), air (500° C., reaction pressure) was injected if appropriate to the reaction gas mixture. The tables 1 to 3 which follow show the results obtained in three experiments as a function of the different starting reaction gas mixtures (4) and of the different metered additions of air.

In the table, the following symbols apply:

L2=addition of air upstream of the second catalyst charge in l (STP)/h

L3=addition of air upstream of the third catalyst charge in l (STP)/h

RA=contents of the starting reaction gas mixture (4) (contained in all cases, based on the amount of propane present, approx. 70% by volume of steam)

R1=contents of the reaction gas after passage through the first catalyst charge

R2=contents of the reaction gas after passage through the second catalyst charge P=contents of the product gas, i.e. the reaction gas after passage through the third catalyst charge TE=entrance temperature of the starting reaction gas mixture into the first catalyst charge in ° C.

T1=highest temperature in the first catalyst charge in ° C.

T2=highest temperature in the second catalyst charge in ° C.

T3=highest temperature in the third catalyst charge in ° C.

TA=outlet temperature of the product gas

B=contents of the resulting charge gas mixture for an inventive partial oxidation (all charge gas mixtures were nonexplosive)

U=propane conversion based on fresh propane and single pass through the dehydrogenation reactor S=selectivity of propylene formation (all contents in % by volume based on the overall gas, calculated without water).

Example 1/Table 1

L2 = 50
L3 = 70

| | RA | R1 | R2 | P | TE | T1 | T2 | T3 | TA | U | S | B |
|---|---|---|---|---|---|---|---|---|---|---|---|---|
| Methane | 0.31 | 0.33 | 0.53 | 0.63 | 498 | 592 | 574 | 579 | 575 | 31 | 84 | |
| Ethane | 0.18 | 0.23 | 0.27 | 0.36 | | | | | | | | |
| Ethene | 0.21 | 0.20 | 0.39 | 0.43 | | | | | | | | |
| Propane | 17.6 | 16.15 | 15.22 | 14.09 | | | | | | | | 20.2 |
| Propylene | 2.67 | 4.54 | 4.72 | 5.35 | | | | | | | | 7.69 |
| $H_2$ | 6.17 | 5.40 | 4.83 | 5.30 | | | | | | | | |
| $O_2$ | 1.77 | — | — | — | | | | | | | | 14.6 |
| $N_2$ | 70.65 | 72.63 | 73.38 | 73.06 | | | | | | | | 54.5 |
| CO | 0.08 | 0.09 | 0.13 | 0.17 | | | | | | | | |
| $CO_2$ | 0.30 | 0.41 | 0.51 | 0.60 | | | | | | | | |

Example 2/Table 2

| | RA | R1 | R2 | P | TE | T1 | T2 | T3 | TA | U | S | B |
|---|---|---|---|---|---|---|---|---|---|---|---|---|
| | L2 = 40 | | | | | | | | | | | |
| | L3 = 50 | | | | | | | | | | | |
| Methane | 0.31 | 0.69 | 0.65 | 0.61 | 537 | 589 | 562 | 569 | 564 | 36 | 86 | |
| Ethane | 0.38 | 0.79 | 0.78 | 0.76 | | | | | | | | |
| Ethene | 0.04 | 0.11 | 0.08 | 0.07 | | | | | | | | |
| Propane | 17.36 | 14.88 | 12.80 | 13.55 | | | | | | | | 16.62 |
| Propylene | 3.28 | 5.79 | 6.33 | 6.56 | | | | | | | | 8.05 |
| $H_2$ | 7.12 | 7.61 | 7.17 | 7.19 | | | | | | | | |
| $O_2$ | 1.77 | — | — | — | | | | | | | | 15.29 |
| $N_2$ | 69.28 | 69.26 | 71.28 | 70.33 | | | | | | | | 57.0 |
| CO | 0.06 | 0.13 | 0.11 | 0.12 | | | | | | | | |
| $CO_2$ | 0.40 | 0.74 | 0.80 | 0.80 | | | | | | | | |

Example 3/Table 3

| | RA | R1 | R2 | P | TE | T1 | T2 | T3 | TA | U | S | B |
|---|---|---|---|---|---|---|---|---|---|---|---|---|
| | L2 = 0 | | | | | | | | | | | |
| | L3 = 70 | | | | | | | | | | | |
| Methane | 0.09 | 0.121 | 0.128 | 0.175 | 463 | 566 | 541 | 547 | 541 | 25 | 93 | |
| Ethane | 0.08 | 0.101 | 0.116 | 0.150 | | | | | | | | |
| Ethene | 0.05 | 0.073 | 0.070 | 0.103 | | | | | | | | |
| Propane | 18.60 | 15.58 | 17.12 | 16.02 | | | | | | | | 23.6 |
| Propylene | 2.50 | 3.94 | 4.30 | 5.00 | | | | | | | | 7.36 |
| $H_2$ | 5.90 | 4.54 | 4.47 | 4.76 | | | | | | | | |
| $O_2$ | 1.77 | — | — | — | | | | | | | | 14.0 |
| $N_2$ | 70.79 | 73.33 | 73.43 | 73.34 | | | | | | | | 52.1 |
| CO | 0.05 | 0.062 | 0.062 | 0.097 | | | | | | | | |
| $CO_2$ | 0.18 | 0.251 | 0.300 | 0.351 | | | | | | | | |

II. Inventive Heterogeneously Catalyzed Two-Stage Partial Oxidation of Propylene to Acrylic Acid (The Steady Operating State is Described)

Experimental Arrangement

First Reaction Stage:

A reaction tube (V2A steel; external diameter 30 mm, wall thickness 2 mm, internal diameter 26 mm, length: 350 cm, and also a thermal tube (external diameter 4 mm), centered in the middle of the reaction tube, to accommodate a thermoelement with which the temperature in the reaction tube can be determined for its entire length) is charged from top to bottom as follows:

Section 1: Length 50 cm
Steatite rings of geometry 7 mm × 7 mm × 4 mm (external diameter × length × internal diameter) as a preliminary bed.
Section 2: Length 140 cm
Catalyst charge of a homogeneous mixture of 30% by weight of steatite rings of geometry 5 mm × 3 mm × 2 mm (external diameter × length × internal diameter) and 80% by weight of unsupported catalyst from section 3.
Section 3: Length 160 cm
Catalyst charge of annular (5 mm × 3 mm × 2 mm = external diameter × length × internal diameter) unsupported catalyst according to example 1 of DE-A 10046957 (stoichiometry: $[Bi_2W_2O_9 \cdot 2WO_3]_{0.5} [Mo_{12}Co_{5.5}Fe_{2.94}Si_{1.59}K_{0.08}O_x]_1)$.

From top to bottom, the first 175 cm are thermostated by means of a salt bath A pumped in countercurrent. The second 175 cm are thermostated by means of a salt bath B pumped in countercurrent.

Second Reaction Stage:

A reaction tube (V2A steel; external diameter 30 mm, wall thickness 2 mm, internal diameter 26 mm, length: 350 cm, and also a thermal tube (external diameter 4 mm), centered in the middle of the reaction tube, to accommodate a thermoelement with which the temperature in the reaction tube can be determined for its entire length) is charged from top to bottom as follows:

Section 1: Length 20 cm
Steatite rings of geometry 7 mm × 7 mm × 4 mm (external diameter × length × internal diameter) as a preliminary bed.
Section 2: Length 90 cm
Catalyst charge of a homogeneous mixture of 30% by weight of steatite rings of geometry 7 mm × 3 mm × 4 mm (external diameter × length × internal diameter) and 75% by weight of coated catalyst from section 4.
Section 3: Length 50 cm
Catalyst charge of a homogeneous mixture of 20% by weight of steatite rings of geometry 7 mm × 3 mm × 4 mm (external diameter × length × internal diameter) and 85% by weight of coated catalyst from section 4.
Section 4: Length 190 cm
Catalyst charge of annular (7 mm × 3 mm × 4 mm = external diameter × length × internal diameter) coated catalyst according to preparation example 5 of DE-A 10046928 (stoichiometry: $Mo_{12}V_3W_{1.2}Cu_{2.4}O_x$).

From top to bottom, the first 175 cm are thermostated by means of a salt bath C pumped in countercurrent. The second 175 cm are thermostated by means of a salt bath D pumped in countercurrent.

Propylene Source and Two-Stage Partial Oxidation to Acrylic Acid

A tray reactor is first operated as in I. The composition of the starting reaction gas mixture for the heterogeneously catalyzed dehydrogenation is as follows (% by volume, based on overall gas):

|  | % by vol. |
|---|---|
| acrylic acid | 0.02 |
| acetic acid | 0.03 |
| water | 9.23 |
| 1-butene | 0.01 |
| isobutene | 0.02 |
| propane | 18.46 |
| propylene | 3.98 |
| ethane | 1.16 |
| ethylene | 0.22 |
| $CO_2$ | 2.34 |
| CO | 0.26 |
| $N_2$ | 59.7 |
| $O_2$ | 1.62 |
| $CH_4$ | 0.12 |
| $H_2$ | 2.83 |

It consists of:

41.9% by volume of oxidation cycle gas which has the following contents:

|  | % by vol. |
|---|---|
| acrylic acid | 0.02 |
| acetic acid | 0.04 |
| $H_2O$ | 2.73 |
| isobutene | 0.01 |
| acrolein | 0.05 |
| propane | 17.30 |
| propylene | 0.32 |
| ethane | 1.20 |
| ethylene | 0.22 |
| $CO_2$ | 2.41 |
| CO | 0.61 |
| $N_2$ | 71.21 |
| $O_2$ | 3.87 |

3.9% by volume of fresh propane which has the following contents:

|  | % by vol. |
|---|---|
| propane | 98.91 |
| isobutane | 0.05 |
| propylene | 0.1 |
| ethane | 0.92 |
| ethylene | 0.01 |

1.02% by volume of hydrogen
2.03% by volume of steam and
51.15% by volume of dehydrogenation cycle gas.

The remaining product gas mixture has the following composition:

|  | % by vol. |
|---|---|
| acrylic acid | 0.02 |
| acetic acid | 0.03 |
| $H_2O$ | 11.84 |
| isobutene | 0.01 |
| propane | 14.32 |
| propylene | 7.52 |
| ethane | 1.21 |
| ethylene | 0.26 |
| $CO_2$ | 2.61 |
| $N_2$ | 58.41 |
| $O_2$ | 0.23 |
| $H_2$ | 3.55 |

The propane and propylene present in the product gas mixture of the heterogeneously catalyzed propane dehydrogenation is removed absorptively as described in I and stripped free again by means of air to obtain the following charge gas for the partial oxidation, which has the following contents:

|  | % by vol. |
|---|---|
| $H_2O$ | 2.39 |
| tetradecane | 0.01 |
| isobutene | 0.01 |
| propane | 15.15 |
| propylene | 7.95 |
| ethane | 1.10 |
| ethylene | 0.20 |
| $CO_2$ | 1.05 |
| $N_2$ | 56.99 |
| $O_2$ | 15.16 |

This charge gas mixture (it lies outside the explosion range) is used to charge the first partial oxidation reaction stage described. The propylene hourly space velocity on the fixed bed catalyst charge is selected at 185 l (STP)/l·h. The pressure at the entrance of the first reaction stage is 3.1 bar. $T_A=322°$ C.; $T_B=328°$ C.

The product gas mixture leaving the first reaction stage had the following contents:

|  | % by vol. |
|---|---|
| acrylic acid | 0.46 |
| acetic acid | 0.14 |
| $H_2O$ | 10.65 |
| 1-butene | 0.01 |
| acrolein | 6.99 |
| propane | 15.16 |
| propylene | 0.17 |
| ethane | 1.10 |
| ethylene | 0.20 |
| $CO_2$ | 1.62 |
| CO | 0.23 |
| $N_2$ | 57.02 |
| $O_2$ | 6.25 |

$C^P_A$, the propene conversion at the end of reaction zone A, is 64.5 mol %.

$C^P_B$, the propene conversion at the end of reaction zone B, is 94.9 mol %.

Sufficient air (25° C.) is added to the product gas mixture of the first stage that the acrolein: $O_2$ ratio in the resulting mixture is 6.59 to 7.07.

This mixture is then used directly to charge the second reaction stage (T=231.7° C.). The acrolein hourly space velocity on the fixed catalyst bed is 152 l (STP)/l·h. $T_C$=263° C.; $T_D$=269° C. The pressure at the entrance of the second reaction stage is 2.1 bar.

The product gas mixture leaving the second reaction stage has the following contents:

|  | % by vol. |
|---|---|
| acrylic acid | 6.72 |
| acetic acid | 0.22 |
| $H_2O$ | 11.06 |
| formaldehyde | 0.14 |
| acrolein | 0.05 |
| formic acid | 0.03 |
| maleic anhydride | 0.06 |
| benzoic acid | 0.01 |
| propane | 14.62 |
| propylene | 0.28 |
| ethane | 1.02 |
| ethylene | 0.18 |
| $CO_2$ | 2.03 |
| CO | 0.52 |
| $N_2$ | 59.86 |
| $O_2$ | 3.20 |
| propionic acid | 0.0032 |

$C^A_C$, the acrolein conversion at the end of reaction zone C, is 68.1 mol %.

$C^A_D$, the acrolein conversion at the end of reaction zone D, is 98.8 mol %.

The propionic acid content based on the amount of acrylic acid present is significantly below those of the examples of WO 01/96270.

In both reaction stages, the reaction gas mixture flows through both catalyst tubes from top to bottom.

The contents are analyzed by means of gas chromatography analysis.

The acrylic acid is removed from the product gas mixture as in the exemplary embodiments of DE-A 10 2004 032 129 and the residual gas is recycled as oxidation cycle gas into the heterogeneously catalyzed dehydrogenation.

U.S. Provisional Patent Applications Nos. 60/584,469 (filed on Jul. 1, 2004), 60/656,874 (filed on Mar. 1, 2005) and 60/657,374 (filed on Mar. 2, 2005) are incorporated into the present application by literature reference. With regard to the above mentioned teachings, numerous alterations and deviations from the present invention are possible. It can therefore be assumed that the invention, within the scope of the appended claims, may be performed differently to the way specifically described herein.

What is claimed is:

1. A process for preparing acrolein or acrylic acid or a mixture thereof by heterogeneously catalyzed partial gas phase oxidation of propylene, in which a starting reaction gas mixture 2 which comprises the propylene and molecular oxygen reactants and inert molecular nitrogen and propane diluent gases and is conducted at elevated temperature through a fixed catalyst bed whose active composition is at least one multimetal oxide comprising the elements Mo, Fe and Bi, wherein starting reaction gas mixture 2, based on its total volume, has the following contents:

| from 7 to 9% by volume of | propylene, |
|---|---|
| from 9.8 to 15.5% by volume of | molecular oxygen, |
| from 10.5 to 15.5% by volume of | propane and |
| from 40 to 60% by volume of | molecular nitrogen, | with the proviso that the molar ratio $V_1$ of propane present in starting reaction gas mixture 2 to propylene present in starting reaction gas mixture 2 is from 1.5 to 2.2, the molar ratio $V_2$ of molecular nitrogen present in starting reaction gas mixture 2 to molecular oxygen present in starting reaction gas mixture 2 is from 3.5 to 4.5 and the molar ratio $V_3$ of molecular oxygen present in starting reaction gas mixture 2 to propylene present in starting reaction gas mixture 2 is from 1.5 to 2.14.

2. The process according to claim 1, wherein $V_2$ is from 3.5 to 4.

3. The process according to claim 1, wherein $V_3$ is from 1.5 to 2.0.

4. The process as claimed in claim 1, wherein starting reaction gas mixture 2 has the following contents:

| from 7 to 8% by volume of | propylene, |
|---|---|
| from 11.9 to 15.5% by volume of | molecular oxygen, |
| from 11.9 to 15.5% by volume of | propane and |
| from 50 to 60% by volume of | molecular nitrogen, | with the proviso that
$V_1$=from 1.7 to 2.1
$V_2$=from 3.5 to 4.5 and
$V_3$=from 1.7 to 2.1.

5. The process according to claim 4, wherein $V_2$ is from 3.5 to 4.

6. The process according to claim 4, wherein $V_3$ is from 1.8 to 2.0.

7. The process according to claim 1, wherein the total content in starting reaction gas mixture 2 of constituents other than propylene, molecular oxygen, propane and molecular nitrogen is $\leq$10% by volume.

8. The process according to claim 1, wherein starting reaction gas mixture 2 comprises from 0.5 to 8% by volume of at least one of the compounds methane and ethane.

9. The process according to claim 1, wherein starting reaction gas mixture 2 comprises from 0.5 to 5% by volume of at least one of the compounds methane and ethane.

10. The process according to claim 1, wherein starting reaction gas mixture 2 comprises from 0.5 to 3% by volume of at least one of the compounds methane and ethane.

11. The process according to claim 1, wherein starting reaction gas mixture 2 comprises $\leq$5% by volume of water and $\leq$5% by volume of carbon oxides.

12. The process according to claim 1, wherein starting reaction gas mixture 2 comprises $\leq$3% by volume of water and $\leq$3% by volume of carbon oxides.

13. The process according to claim 1, wherein starting reaction gas mixture 2 comprises $\leq$2% by volume of water and $\leq$2% by volume of carbon oxides.

14. The process according to claim 1, wherein starting reaction gas mixture 2 comprises $\geq$0.5% by volume of water.

15. The process according to claim 1, wherein the total content in starting reaction gas mixture 2 of constituents other than propylene, molecular oxygen, propane and molecular nitrogen is $\leq$5% by volume.

16. The process according to claim 1, wherein the total content in starting reaction gas mixture 2 of constituents other than propylene, molecular oxygen, propane and molecular nitrogen is $\leq$3% by volume.

17. The process according to claim 1, wherein the source used for the propylene present in starting reaction gas mixture 2 is propylene formed in processes for the continuous heterogeneously catalyzed partial dehydrogenation and/or oxydehydrogenation of propane in the gas phase, without propane unconverted in the heterogeneously catalyzed partial dehydrogenation and/or oxydehydrogenation being removed beforehand from this propylene.

18. The process according to claim 17, wherein the process of a heterogeneously catalyzed partial dehydrogenation of propane is an autothermal dehydrogenation.

19. The process according to claim 17, wherein the process for the heterogeneously catalyzed partial dehydrogenation of propane is one in which
a starting reaction gas mixture 1 comprising the propane to be dehydrogenated is fed continuously to a dehydrogenation zone,
in the dehydrogenation zone, starting reaction gas mixture 1 is conducted through at least one fixed catalyst bed over which molecular hydrogen and propylene are formed by catalytic dehydrogenation,
at least one molecular oxygen-containing gas is added to starting reaction gas mixture 1 before and/or after entry into the dehydrogenation zone,
the molecular oxygen is oxidized in the dehydrogenation zone partly to steam in the molecular hydrogen present in reaction gas mixture 1 and
a product gas which comprises molecular hydrogen, steam, propylene and unconverted propane is withdrawn from the dehydrogenation zone, with the proviso that the product gas withdrawn from the dehydrogenation zone is divided into two portions of identical composition and one of the two portions is recycled into the dehydrogenation zone as dehydrogenation cycle gas.

20. The process according to claim 19, wherein the dehydrogenation cycle gas is recycled into starting reaction gas mixture 1.

21. The process according to claim 20, wherein starting reaction gas mixture 1 comprises:

| | |
|---|---|
| from 15 to 25% by volume of | propane, |
| from 2 to 6% by volume of | propylene, |
| from 5 to 20% by volume of | steam, |
| from 2 to 10% by volume of | molecular hydrogen, |
| from 40 to 75% by volume of | molecular nitrogen and |
| from >0 to 3% by volume of | molecular oxygen. |

22. The process according to claim 20, wherein the product gas comprises propane and propylene in a molecular propene to propylene ratio of from 0.3 to 0.66.

23. The process according to claim 1, wherein the source used for the propylene present in starting reaction gas mixture 2 is the product gas mixture of a partial propane dehydrogenation in which at least 50% by volume of the constituents other than propane and propylene present in the product gas of the propane dehydrogenation have been removed.

24. The process according to claim 1, wherein the hourly space velocity on the fixed catalyst bed of propylene is from ≧135 l (STP)/l·h to 300 l (STP)/l·h.

25. The process according to claim 1, wherein the propylene conversion in single pass is ≧90 mol % and the associated selectivity of acrolein formation and of acrylic acid by-product formation taken together is ≧90 mol % and
a) the hourly space velocity on the fixed catalyst bed of propylene present in starting reaction gas mixture 2 is ≧160 l (STP) of propylene/l of fixed catalyst bed·h,
b) the fixed catalyst bed consists of one fixed catalyst bed arranged in two spatially successive reaction zones A*, B*, the temperature of reaction zone A* being from 300 to 390° C. and a temperature of reaction zone B* being from 305 to 420° C. and at the same time at least 5° C. above the temperature of reaction zone A*,
c) starting reaction gas mixture 2 flows through reaction zones A*, B* in the time sequence "first A*", "then B*" and
d) reaction zone A* extends up to a conversion of propylene of from 40 to 80 mol %.

26. The process according to claim 1, which is followed by a process for the heterogeneously catalyzed partial gas phase oxidation of acrolein formed in the process according to claim 1 to acrylic acid, in which a starting reaction gas mixture 3 comprising acrolein is conducted through a fixed catalyst bed whose active composition is at least one multimetal oxide comprising the elements Mo and V.

27. The process according to claim 26, wherein starting reaction gas mixture 3 has the following contents:

| | |
|---|---|
| from 4.5 to 8% by volume of | acrolein, |
| from 2.25 to 9% by volume of | molecular oxygen, |
| from 6 to 30% by volume of | propane, |
| from 32 to 72% by volume of | molecular nitrogen, |
| from 5 to 15% by volume of | steam. |

28. The process according to claim 27, wherein starting reaction gas mixture 3 comprises from 4.5 to 9% by volume of molecular oxygen.

29. The process according to claim 26, wherein starting reaction gas mixture 3 has the following contents:

| | |
|---|---|
| from 5.5 to 8% by volume of | acrolein, |
| from 2.75 to 9% by volume of | molecular oxygen, |
| from 10 to 25% by volume of | propane, |
| from 40 to 70% by volume of | molecular nitrogen, |
| from 5 to 15% by volume of | steam. |

30. The process according to claim 29, wherein starting reaction gas mixture 3 comprises from 5.5 to 9% by volume of molecular oxygen.

31. The process according to claim 26, wherein starting reaction gas mixture 3 has the following contents:

| | |
|---|---|
| from 6 to 8% by volume of | acrolein, |
| from 3 to 9% by volume of | molecular oxygen, |
| from 10 to 20% by volume of | propane, |
| from 50 to 65% by volume of | molecular nitrogen, |
| from 7 to 13% by volume of | steam. |

32. The process according to claim 31, wherein starting reaction gas mixture 3 comprises from 6 to 9% by volume of molecular oxygen.

33. The process according to claim 31, wherein starting reaction gas mixture 3 comprises from 6 to 7% by volume of acrolein.

34. The process according to claim 31, wherein starting reaction gas mixture 3 comprises from 10 to 16% by volume of propane.

35. The process according to claim 27, wherein starting reaction gas mixture 3 comprises from 0.5 to 8% by volume of methane and/or ethane.

36. The process according to claim 26, wherein the acrolein hourly space velocity on the fixed catalyst bed is from ≧135 l (STP)/l·h to 290 l (STP)/l·h.

37. The process according to claim 26, wherein the acrolein conversion in single pass is ≧90 mol % and the associated selectivity of acrylic acid formation is ≧90 mol %, and
   a) the hourly space velocity on the fixed catalyst bed of acrolein present in starting reaction gas mixture 3 is ≧150 l(STP) of acrolein/l of fixed catalyst bed·h,
   b) the fixed catalyst bed consists of one fixed catalyst bed arranged in two spatially successive reaction zones C*, D*, the temperature of reaction zone C* being from 230 to 270° C. and a temperature of reaction zone D* being from 205 to 300° C. and at the same time at least 5° C. above the temperature of reaction zone C*,
   c) starting reaction gas mixture 3 flows through reaction zones C*, D* in the time sequence "first C*", "then D*"and
   d) reaction zone C* extends up to a conversion of acrolein of from 55 to 85 mol %.

38. The process according to claim 1,
which is followed if appropriate by a process for the heterogeneously catalyzed partial gas phase oxidation of acrolein formed in the process according to claim 1, in which this acrolein is conducted as a constituent of a starting reaction gas mixture 3 through a fixed catalyst bed whose active composition is at least one multimetal oxide comprising the elements Mo and V, and,
in a first stage preceding the process according to claim 1, propane is subjected, as a constituent of a starting reaction gas mixture 1, to a partial heterogeneously catalyzed dehydrogenation in the gas phase to form a product gas mixture 1 which comprises propylene and unconverted propane,
a portion is removed if appropriate from the constituents other than propane and propylene present in the product gas mixture 1, comprising propylene and unconverted propane, of the preceding stage and it is then used as a constituent of starting reaction gas mixture 2,
acrolein, acrylic acid or a mixture thereof is removed as the target product from the product gas mixture resulting from the partial gas phase oxidation and at least unconverted propane remaining in this removal is recycled into the preceding first stage and
fresh propane is added to starting reaction gas mixture 2 and/or to starting reaction gas mixture 3.

39. The process according to claim 26, which is followed by a process in which the product gas mixture of the acrolein partial oxidation, after direct and/or indirect cooling if appropriate, is fractionally condensed ascending within a column comprising separating internals with side draw removal of crude acrylic acid and/or absorbed with water and/or aqueous solution.

40. The process according to claim 39, which is followed by a process in which the crude acrylic acid is subjected to a suspension crystallization to form acrylic acid suspension crystals and remaining mother liquor.

41. The process according to claim 40, which is followed by a process in which the acrylic acid suspension crystals are removed from remaining mother liquor by means of a wash column.

42. The process according to claim 41, wherein the wash column is one with forced transport of the crystal bed.

43. The process according to claim 41, wherein the wash column is a hydraulic wash column.

44. The process according to claim 41, wherein the wash liquid used is the melt of acrylic acid crystals which have been removed beforehand in the wash column.

45. The process according to claim 41, which is followed by a process in which the removed acrylic acid suspension crystals are melted and free-radically polymerized to polymers.

* * * * *